US012558486B2

(12) United States Patent
Zikry et al.

(10) Patent No.: US 12,558,486 B2
(45) Date of Patent: Feb. 24, 2026

(54) AUTOMATIC LOCKING AND UNLOCKING VACUUM SYRINGES, AND ASSOCIATED SYSTEMS AND METHODS

(71) Applicant: Inari Medical, Inc., Irvine, CA (US)

(72) Inventors: Christopher Andrew Zikry, Northridge, CA (US); Benjamin Edward Merritt, San Clemente, CA (US); Parker Ozenne, Aliso Viejo, CA (US); Steven McConnell, Anaheim, CA (US); Mikayla Ann Barkley, Irvine, CA (US)

(73) Assignee: Inari Medical, Inc., Irvine, CA (US)

( * ) Notice: Subject to any disclaimer, the term of this patent is extended or adjusted under 35 U.S.C. 154(b) by 0 days.

(21) Appl. No.: 18/949,343

(22) Filed: Nov. 15, 2024

(65) Prior Publication Data

US 2025/0161572 A1 May 22, 2025

Related U.S. Application Data

(60) Provisional application No. 63/599,648, filed on Nov. 16, 2023.

(51) Int. Cl.
*A61M 5/315* (2006.01)
*A61M 5/20* (2006.01)

(52) U.S. Cl.
CPC ...... *A61M 5/31501* (2013.01); *A61M 5/2033* (2013.01)

(58) Field of Classification Search
CPC .. A61B 17/22; A61B 17/22079; A61M 5/178; A61M 5/31501; A61M 5/2033;
(Continued)

(56) References Cited

U.S. PATENT DOCUMENTS

| | | | |
|---|---|---|---|
| 1,101,890 A | 6/1914 | Tunstead | |
| 2,434,835 A | 1/1948 | Colley | |

(Continued)

FOREIGN PATENT DOCUMENTS

| | | | |
|---|---|---|---|
| AU | 2015210338 | 8/2015 | |
| CN | 1501825 | 6/2004 | |

(Continued)

OTHER PUBLICATIONS

US 12,114,876 B2, 10/2024, Quick et al. (withdrawn)
(Continued)

*Primary Examiner* — Andrew J Mensh
*Assistant Examiner* — Nhu Q. Tran
(74) *Attorney, Agent, or Firm* — Perkins Coie LLP

(57) ABSTRACT

Disclosed herein are automatic-locking and automatic-unlocking syringes, and associated systems and methods. In some embodiments, a syringe can include a barrel, a plunger assembly slidably positioned within the barrel, and a locking assembly coupled to the barrel. The syringe is configured to (i) automatically lock the plunger assembly to the locking assembly when the plunger assembly is withdrawn through the barrel with a vacuum in the barrel, (ii) automatically unlock the plunger assembly from the locking assembly when the barrel no longer experiences vacuum and/or experiences negligible vacuum, and/or (iii) inhibit or even prevent automatic locking of the plunger assembly to the locking assembly when the plunger assembly is withdrawn through the barrel with no and/or negligible vacuum within the barrel.

15 Claims, 15 Drawing Sheets

(58) Field of Classification Search
CPC ............ A61M 5/3148; A61M 5/31505; A61M
2005/31508; A61M 1/67
See application file for complete search history.

(56) References Cited

U.S. PATENT DOCUMENTS

| | | | |
|---|---|---|---|
| 2,502,639 A | 4/1950 | Blake | |
| 2,695,023 A | 11/1954 | Brown | |
| 2,707,954 A | 5/1955 | Kas, Sr. | |
| 2,784,717 A | 3/1957 | Thompson | |
| 2,846,179 A | 8/1958 | Monckton | |
| 2,955,592 A | 10/1960 | Maclean | |
| 3,088,363 A | 5/1963 | Sparks | |
| 3,197,173 A | 7/1965 | Taubenheim | |
| 3,383,131 A | 5/1968 | Rosfelder | |
| 3,416,531 A | 12/1968 | Edwards | |
| 3,435,826 A | 4/1969 | Fogarty | |
| 3,438,607 A | 4/1969 | Williams et al. | |
| 3,515,137 A | 6/1970 | Santomieri | |
| 3,661,144 A | 5/1972 | Jensen et al. | |
| 3,675,657 A | 7/1972 | Gauthier | |
| 3,785,380 A | 1/1974 | Brumfield | |
| 3,860,006 A | 1/1975 | Patel | |
| 3,863,624 A | 2/1975 | Gram | |
| 3,892,161 A | 7/1975 | Sokol | |
| 3,923,065 A | 12/1975 | Nozick et al. | |
| 4,030,503 A | 6/1977 | Clark, III | |
| 4,034,642 A | 7/1977 | Iannucci et al. | |
| 4,036,232 A | 7/1977 | Genese | |
| 4,187,849 A | 2/1980 | Stim | |
| 4,222,380 A | 9/1980 | Terayama | |
| 4,243,040 A | 1/1981 | Beecher | |
| 4,287,808 A | 9/1981 | Leonard et al. | |
| 4,324,262 A | 4/1982 | Hall | |
| 4,393,872 A | 7/1983 | Reznik et al. | |
| 4,401,107 A | 8/1983 | Harber et al. | |
| 4,469,100 A | 9/1984 | Hardwick | |
| 4,523,738 A | 6/1985 | Raftis et al. | |
| 4,551,862 A | 11/1985 | Haber | |
| 4,604,094 A | 8/1986 | Shook | |
| 4,611,594 A | 9/1986 | Grayhack et al. | |
| 4,634,421 A | 1/1987 | Hegemann | |
| 4,643,184 A | 2/1987 | Mobin-Uddin | |
| 4,646,736 A | 3/1987 | Auth et al. | |
| 4,650,466 A | 3/1987 | Luther | |
| 4,693,257 A | 9/1987 | Markham | |
| 4,705,518 A | 11/1987 | Baker et al. | |
| 4,743,230 A | 5/1988 | Nordquest | |
| 4,776,337 A | 10/1988 | Palmaz | |
| 4,790,812 A | 12/1988 | Hawkins, Jr. et al. | |
| 4,826,483 A | 5/1989 | Molnar, IV | |
| 4,863,440 A | 9/1989 | Chin et al. | |
| 4,870,953 A | 10/1989 | DonMichael et al. | |
| 4,872,579 A | 10/1989 | Palmer | |
| 4,880,408 A | 11/1989 | Cumes et al. | |
| 4,883,458 A | 11/1989 | Shiber | |
| 4,886,062 A | 12/1989 | Wiktor | |
| 4,890,611 A | 1/1990 | Monfort et al. | |
| 4,898,575 A | 2/1990 | Fischell et al. | |
| 4,946,440 A | 8/1990 | Hall | |
| 4,960,259 A | 10/1990 | Sunnanvader et al. | |
| 4,978,341 A | 12/1990 | Niederhauser | |
| 4,981,478 A | 1/1991 | Evard et al. | |
| 5,030,201 A | 7/1991 | Palestrant | |
| 5,053,008 A | 10/1991 | Bajaj | |
| 5,059,178 A | 10/1991 | Ya | |
| 5,064,428 A | 11/1991 | Cope et al. | |
| 5,100,423 A | 3/1992 | Fearnot | |
| 5,127,626 A | 7/1992 | Hilal et al. | |
| 5,129,910 A | 7/1992 | Phan et al. | |
| 5,135,484 A | 8/1992 | Wright | |
| 5,154,724 A | 10/1992 | Andrews | |
| 5,158,533 A | 10/1992 | Strauss et al. | |
| 5,158,564 A | 10/1992 | Schnepp-Pesch et al. | |
| 5,192,274 A | 3/1993 | Bierman | |
| 5,192,286 A | 3/1993 | Phan et al. | |
| 5,192,290 A | 3/1993 | Hilal | |
| 5,197,485 A | 3/1993 | Grooters | |
| 5,215,536 A * | 6/1993 | Lampropoulos ...... | A61M 5/315 |
| | | | 604/218 |
| 5,234,403 A | 8/1993 | Yoda et al. | |
| 5,242,461 A | 9/1993 | Kortenbach et al. | |
| 5,244,619 A | 9/1993 | Burnham | |
| 5,246,011 A | 9/1993 | Caillouette | |
| 5,250,025 A | 10/1993 | Sosnowski et al. | |
| 5,279,546 A | 1/1994 | Mische et al. | |
| 5,323,514 A | 6/1994 | Masuda et al. | |
| 5,329,923 A | 7/1994 | Lundquist | |
| 5,337,780 A | 8/1994 | Kee | |
| 5,360,417 A | 11/1994 | Gravener et al. | |
| 5,364,345 A | 11/1994 | Lowery et al. | |
| 5,376,071 A | 12/1994 | Henderson | |
| 5,376,101 A | 12/1994 | Green et al. | |
| 5,378,230 A | 1/1995 | Mahurkar | |
| 5,383,887 A | 1/1995 | Nadal | |
| 5,389,100 A | 2/1995 | Bacich et al. | |
| 5,391,152 A | 2/1995 | Patterson et al. | |
| 5,419,774 A | 5/1995 | Willard et al. | |
| 5,421,824 A | 6/1995 | Clement et al. | |
| 5,429,610 A | 7/1995 | Vaillancourt | |
| 5,443,443 A | 8/1995 | Shiber | |
| 5,456,667 A | 10/1995 | Ham et al. | |
| 5,476,450 A | 12/1995 | Ruggio | |
| 5,484,418 A | 1/1996 | Quiachon et al. | |
| 5,490,859 A | 2/1996 | Mische et al. | |
| 5,496,365 A | 3/1996 | Sgro | |
| 5,527,326 A | 6/1996 | Hermann et al. | |
| 5,549,626 A | 8/1996 | Miller et al. | |
| 5,591,137 A | 1/1997 | Stevens | |
| 5,639,276 A | 6/1997 | Weinstock et al. | |
| 5,653,684 A | 8/1997 | Laptewicz et al. | |
| 5,662,703 A | 9/1997 | Yurek et al. | |
| 5,746,758 A | 5/1998 | Nordgren et al. | |
| 5,749,858 A | 5/1998 | Cramer | |
| 5,769,816 A | 6/1998 | Barbut et al. | |
| 5,782,817 A | 7/1998 | Franzel et al. | |
| 5,800,457 A | 9/1998 | Gelbfish | |
| 5,827,229 A | 10/1998 | Auth et al. | |
| 5,846,251 A | 12/1998 | Hart | |
| 5,860,938 A | 1/1999 | Lafontaine et al. | |
| 5,867,385 A | 2/1999 | Brown et al. | |
| 5,873,866 A | 2/1999 | Kondo et al. | |
| 5,873,882 A | 2/1999 | Straub et al. | |
| 5,876,414 A | 3/1999 | Straub | |
| 5,895,406 A | 4/1999 | Gray et al. | |
| 5,908,435 A | 6/1999 | Samuels | |
| 5,911,710 A | 6/1999 | Barry et al. | |
| 5,911,728 A | 6/1999 | Sepetka et al. | |
| 5,911,733 A | 6/1999 | Parodi | |
| 5,911,754 A | 6/1999 | Kanesaka et al. | |
| 5,941,869 A | 8/1999 | Patterson et al. | |
| 5,947,985 A | 9/1999 | Imram | |
| 5,951,539 A | 9/1999 | Nita et al. | |
| 5,954,737 A | 9/1999 | Lee | |
| 5,971,938 A | 10/1999 | Hart et al. | |
| 5,971,958 A | 10/1999 | Zhang | |
| 5,972,019 A | 10/1999 | Engelson et al. | |
| 5,974,938 A | 11/1999 | Lloyd | |
| 5,989,233 A | 11/1999 | Yoon | |
| 5,993,483 A | 11/1999 | Gianotti | |
| 6,017,335 A | 1/2000 | Burnham | |
| 6,030,397 A | 2/2000 | Moneti et al. | |
| 6,059,745 A | 5/2000 | Gelbfish | |
| 6,059,814 A | 5/2000 | Ladd | |
| 6,066,158 A | 5/2000 | Engelson et al. | |
| 6,068,645 A | 5/2000 | Tu | |
| 6,126,635 A | 10/2000 | Simpson et al. | |
| 6,142,987 A | 11/2000 | Tsugita | |
| 6,146,396 A | 11/2000 | Konya et al. | |
| 6,146,403 A | 11/2000 | St. Germain | |
| 6,152,144 A | 11/2000 | Lesh et al. | |
| 6,152,909 A | 11/2000 | Bagaoisan et al. | |
| 6,152,946 A | 11/2000 | Broome et al. | |
| 6,156,055 A | 12/2000 | Ravenscroft | |

(56) References Cited

U.S. PATENT DOCUMENTS

| | | | |
|---|---|---|---|
| 6,159,230 A | 12/2000 | Samuels | |
| 6,165,196 A | 12/2000 | Stack et al. | |
| 6,168,579 B1 | 1/2001 | Tsugita | |
| 6,179,859 B1 | 1/2001 | Bates et al. | |
| 6,221,006 B1 | 4/2001 | Dubrul et al. | |
| 6,228,060 B1 | 5/2001 | Howell | |
| 6,238,412 B1 | 5/2001 | Dubrul et al. | |
| 6,245,078 B1 | 6/2001 | Ouchi | |
| 6,245,089 B1 | 6/2001 | Daniel et al. | |
| 6,254,571 B1 | 7/2001 | Hart | |
| 6,258,115 B1 | 7/2001 | Dubrul | |
| 6,264,663 B1 | 7/2001 | Cano | |
| 6,306,163 B1 | 10/2001 | Fitz | |
| 6,322,572 B1 | 11/2001 | Lee | |
| 6,350,271 B1 | 2/2002 | Kurz et al. | |
| 6,361,545 B1 | 3/2002 | Macoviak et al. | |
| 6,364,895 B1 | 4/2002 | Greenhalgh | |
| 6,368,339 B1 | 4/2002 | Amplatz | |
| 6,383,205 B1 | 5/2002 | Samson et al. | |
| 6,402,771 B1 | 6/2002 | Palmer et al. | |
| 6,413,235 B1 | 7/2002 | Parodi | |
| 6,423,032 B2 | 7/2002 | Parodi | |
| 6,432,122 B1 | 8/2002 | Gilson et al. | |
| 6,436,085 B1 | 8/2002 | Lauer | |
| 6,451,036 B1 | 9/2002 | Heitzmann et al. | |
| 6,458,103 B1 | 10/2002 | Albert et al. | |
| 6,475,236 B1 | 11/2002 | Roubin et al. | |
| 6,485,502 B2 | 11/2002 | Don Michael | |
| 6,508,782 B1 | 1/2003 | Evans et al. | |
| 6,511,492 B1 | 1/2003 | Rosenbluth et al. | |
| 6,514,273 B1 | 2/2003 | Voss et al. | |
| 6,530,923 B1 | 3/2003 | Dubrul et al. | |
| 6,530,935 B2 | 3/2003 | Wensel et al. | |
| 6,540,722 B1 | 4/2003 | Boyle et al. | |
| 6,544,276 B1 | 4/2003 | Azizi | |
| 6,544,278 B1 | 4/2003 | Vrba et al. | |
| 6,544,279 B1 | 4/2003 | Hopkins et al. | |
| 6,551,342 B1 | 4/2003 | Shen et al. | |
| 6,564,828 B1 | 5/2003 | Ishida | |
| 6,569,181 B1 | 5/2003 | Burns | |
| 6,575,995 B1 | 6/2003 | Huter et al. | |
| 6,589,263 B1 | 7/2003 | Hopkins et al. | |
| 6,589,264 B1 | 7/2003 | Barbut et al. | |
| 6,596,011 B2 | 7/2003 | Johnson et al. | |
| 6,602,271 B2 | 8/2003 | Adams et al. | |
| 6,605,074 B2 | 8/2003 | Zadno-azizi et al. | |
| 6,605,102 B1 | 8/2003 | Mazzocchi et al. | |
| 6,610,077 B1 | 8/2003 | Hancock et al. | |
| 6,620,148 B1 | 9/2003 | Tsugita | |
| 6,620,179 B2 | 9/2003 | Brook et al. | |
| 6,620,182 B1 | 9/2003 | Khosravi et al. | |
| 6,623,460 B1 | 9/2003 | Heck | |
| 6,635,068 B1 | 10/2003 | Dubrul et al. | |
| 6,645,222 B1 | 11/2003 | Parodi et al. | |
| 6,660,013 B2 | 12/2003 | Rabiner et al. | |
| 6,660,014 B2 | 12/2003 | Demarais et al. | |
| 6,663,650 B2 | 12/2003 | Sepetka et al. | |
| 6,679,893 B1 | 1/2004 | Tran | |
| 6,692,504 B2 | 2/2004 | Kurz et al. | |
| 6,699,260 B2 | 3/2004 | Dubrul et al. | |
| 6,702,830 B1 | 3/2004 | Demarais et al. | |
| 6,719,717 B1 | 4/2004 | Johnson et al. | |
| 6,755,847 B2 | 6/2004 | Eskuri | |
| 6,767,353 B1 | 7/2004 | Shiber | |
| 6,790,204 B2 | 9/2004 | Zadno-azizi et al. | |
| 6,800,080 B1 | 10/2004 | Bates | |
| 6,818,006 B2 | 11/2004 | Douk et al. | |
| 6,824,545 B2 | 11/2004 | Sepetka et al. | |
| 6,824,550 B1 | 11/2004 | Noriega et al. | |
| 6,824,553 B1 | 11/2004 | Gene et al. | |
| 6,830,561 B2 | 12/2004 | Jansen et al. | |
| 6,846,029 B1 | 1/2005 | Ragner et al. | |
| 6,902,540 B2 | 6/2005 | Dorros et al. | |
| 6,908,455 B2 | 6/2005 | Hajianpour | |
| 6,939,361 B1 | 9/2005 | Kleshinski | |
| 6,942,682 B2 | 9/2005 | Vrba et al. | |
| 6,945,977 B2 | 9/2005 | Demarais et al. | |
| 6,960,189 B2 | 11/2005 | Bates et al. | |
| 6,960,222 B2 | 11/2005 | Vo et al. | |
| 7,004,931 B2 | 2/2006 | Hogendijk | |
| 7,004,954 B1 | 2/2006 | Voss et al. | |
| 7,036,707 B2 | 5/2006 | Aota et al. | |
| 7,041,084 B2 | 5/2006 | Fotjik | |
| 7,052,500 B2 | 5/2006 | Bashiri et al. | |
| 7,056,328 B2 | 6/2006 | Arnott | |
| 7,063,707 B2 | 6/2006 | Bose et al. | |
| 7,069,835 B2 | 7/2006 | Nishri et al. | |
| 7,094,249 B1 | 8/2006 | Thomas et al. | |
| 7,122,034 B2 | 10/2006 | Belhe et al. | |
| 7,128,073 B1 | 10/2006 | van der Burg et al. | |
| 7,152,605 B2 | 12/2006 | Khairkhahan et al. | |
| 7,179,273 B1 | 2/2007 | Palmer et al. | |
| 7,223,253 B2 | 5/2007 | Hogendijk | |
| 7,232,432 B2 | 6/2007 | Fulton, III et al. | |
| 7,244,243 B2 | 7/2007 | Lary | |
| 7,285,126 B2 | 10/2007 | Sepetka et al. | |
| 7,300,458 B2 | 11/2007 | Henkes et al. | |
| 7,306,618 B2 | 12/2007 | Demond et al. | |
| 7,320,698 B2 | 1/2008 | Eskuri | |
| 7,323,002 B2 | 1/2008 | Johnson et al. | |
| 7,331,980 B2 | 2/2008 | Dubrul et al. | |
| 7,481,805 B2 | 1/2009 | Magnusson | |
| 7,534,234 B2 | 5/2009 | Fotjik | |
| 7,578,830 B2 | 8/2009 | Kusleika et al. | |
| 7,621,870 B2 | 11/2009 | Berrada et al. | |
| 7,674,247 B2 | 3/2010 | Fotjik | |
| 7,678,131 B2 | 3/2010 | Muller | |
| 7,691,121 B2 | 4/2010 | Rosenbluth et al. | |
| 7,695,458 B2 | 4/2010 | Belley et al. | |
| 7,713,282 B2 | 5/2010 | Frazier et al. | |
| 7,722,641 B2 | 5/2010 | van der Burg et al. | |
| 7,763,010 B2 | 7/2010 | Evans et al. | |
| 7,766,934 B2 | 8/2010 | Pal et al. | |
| 7,775,501 B2 | 8/2010 | Kees | |
| 7,780,696 B2 | 8/2010 | Daniel et al. | |
| 7,815,608 B2 | 10/2010 | Schafersman et al. | |
| 7,905,877 B1 | 3/2011 | Oscar et al. | |
| 7,905,896 B2 | 3/2011 | Straub | |
| 7,938,809 B2 | 5/2011 | Lampropoulos et al. | |
| 7,938,820 B2 | 5/2011 | Webster et al. | |
| 7,967,790 B2 | 6/2011 | Whiting et al. | |
| 7,976,511 B2 | 7/2011 | Fotjik | |
| 7,993,302 B2 | 8/2011 | Hebert et al. | |
| 7,993,363 B2 | 8/2011 | Demond et al. | |
| 8,021,351 B2 | 9/2011 | Boldenow et al. | |
| 8,043,313 B2 | 10/2011 | Krolik et al. | |
| 8,052,640 B2 | 11/2011 | Fiorella et al. | |
| 8,057,496 B2 | 11/2011 | Fischer, Jr. | |
| 8,057,497 B1 | 11/2011 | Raju et al. | |
| 8,066,757 B2 | 11/2011 | Ferrera et al. | |
| 8,070,694 B2 | 12/2011 | Galdonik et al. | |
| 8,070,769 B2 | 12/2011 | Broome | |
| 8,070,791 B2 | 12/2011 | Ferrera et al. | |
| 8,075,510 B2 | 12/2011 | Aklog et al. | |
| 8,080,032 B2 | 12/2011 | van der Burg et al. | |
| 8,088,140 B2 | 1/2012 | Ferrera et al. | |
| 8,092,486 B2 | 1/2012 | Berrada et al. | |
| 8,100,935 B2 | 1/2012 | Rosenbluth et al. | |
| 8,109,962 B2 | 2/2012 | Pal | |
| 8,118,275 B2 | 2/2012 | Mialhe | |
| 8,118,829 B2 | 2/2012 | Carrison et al. | |
| 8,187,465 B2 | 5/2012 | Nierich | |
| 8,191,457 B2 | 6/2012 | Kanner et al. | |
| 8,197,493 B2 | 6/2012 | Ferrera et al. | |
| 8,246,641 B2 | 8/2012 | Osborne et al. | |
| 8,261,648 B1 | 9/2012 | Marchand et al. | |
| 8,267,897 B2 | 9/2012 | Wells | |
| 8,298,257 B2 | 10/2012 | Sepetka et al. | |
| 8,317,748 B2 | 11/2012 | Fiorella et al. | |
| 8,337,450 B2 | 12/2012 | Fotjik | |
| RE43,902 E | 1/2013 | Hopkins et al. | |
| 8,343,167 B2 | 1/2013 | Henson | |
| 8,357,178 B2 | 1/2013 | Grandfield et al. | |
| 8,361,104 B2 | 1/2013 | Jones et al. | |

(56) References Cited

U.S. PATENT DOCUMENTS

| | | | |
|---|---|---|---|
| 8,409,215 B2 | 4/2013 | Sepetka et al. |
| 8,439,858 B2 | 5/2013 | Huang et al. |
| 8,480,708 B2 | 7/2013 | Kassab et al. |
| 8,486,105 B2 | 7/2013 | Demond et al. |
| 8,491,539 B2 | 7/2013 | Fotjik |
| 8,512,352 B2 | 8/2013 | Martin |
| 8,523,897 B2 | 9/2013 | van der Burg et al. |
| 8,529,596 B2 | 9/2013 | Grandfield et al. |
| 8,535,283 B2 | 9/2013 | Heaton et al. |
| 8,535,334 B2 | 9/2013 | Martin |
| 8,535,343 B2 | 9/2013 | van der Burg et al. |
| 8,545,526 B2 | 10/2013 | Martin et al. |
| 8,568,432 B2 | 10/2013 | Straub |
| 8,568,465 B2 | 10/2013 | Freudenthal et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,754 B2 | 12/2013 | Wensel et al. |
| 8,613,717 B2 | 12/2013 | Aklog et al. |
| 8,632,584 B2 | 1/2014 | Henkes et al. |
| 8,647,367 B2 | 2/2014 | Kassab et al. |
| 8,657,867 B2 | 2/2014 | Dorn et al. |
| 8,696,622 B2 | 4/2014 | Fiorella et al. |
| 8,715,314 B1 | 5/2014 | Janardhan et al. |
| 8,721,714 B2 | 5/2014 | Kelley |
| 8,753,322 B2 | 6/2014 | Hu et al. |
| 8,764,730 B2 | 7/2014 | Taber |
| 8,771,289 B2 | 7/2014 | Mohiuddin et al. |
| 8,777,893 B2 | 7/2014 | Malewicz |
| 8,784,441 B2 | 7/2014 | Rosenbluth et al. |
| 8,784,442 B2 | 7/2014 | Jones et al. |
| 8,784,469 B2 | 7/2014 | Kassab |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,801,748 B2 | 8/2014 | Martin |
| 8,808,259 B2 | 8/2014 | Walton et al. |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,834,519 B2 | 9/2014 | van der Burg et al. |
| 8,845,621 B2 | 9/2014 | Fotjik |
| 8,852,205 B2 | 10/2014 | Brady et al. |
| 8,852,226 B2 | 10/2014 | Gilson et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 8,992,504 B2 | 3/2015 | Castella et al. |
| 9,005,172 B2 | 4/2015 | Chung |
| 9,011,551 B2 | 4/2015 | Oral et al. |
| 9,028,401 B1 | 5/2015 | Bacich et al. |
| 9,044,575 B2 | 6/2015 | Beasley et al. |
| 9,072,537 B2 | 7/2015 | Grandfield et al. |
| 9,078,682 B2 | 7/2015 | Lenker et al. |
| 9,101,382 B2 | 8/2015 | Krolik et al. |
| 9,125,683 B2 | 9/2015 | Farhangnia et al. |
| 9,126,016 B2 | 9/2015 | Fulton |
| 9,126,020 B2 | 9/2015 | Farhangnia et al. |
| 9,149,609 B2 | 10/2015 | Ansel et al. |
| 9,155,552 B2 | 10/2015 | Ulm, III |
| 9,161,766 B2 | 10/2015 | Slee et al. |
| 9,168,043 B2 | 10/2015 | van der Burg et al. |
| 9,173,668 B2 | 11/2015 | Ulm, III |
| 9,186,487 B2 | 11/2015 | Dubrul et al. |
| D744,639 S | 12/2015 | Aklog et al. |
| 9,204,887 B2 | 12/2015 | Cully et al. |
| 9,216,277 B2 | 12/2015 | Myers |
| 9,241,669 B2 | 1/2016 | Pugh et al. |
| 9,254,352 B2 | 2/2016 | Kumar et al. |
| 9,259,237 B2 | 2/2016 | Quick et al. |
| 9,265,512 B2 | 2/2016 | Carrison et al. |
| 9,283,066 B2 | 3/2016 | Hopkins et al. |
| 9,301,769 B2 | 4/2016 | Brady et al. |
| 9,351,747 B2 | 5/2016 | Kugler et al. |
| 9,358,037 B2 | 6/2016 | Farhangnia et al. |
| 9,402,938 B2 | 8/2016 | Aklog et al. |
| 9,439,664 B2 | 9/2016 | Sos |
| 9,439,751 B2 | 9/2016 | White et al. |
| 9,456,834 B2 | 10/2016 | Folk |
| 9,463,035 B1 | 10/2016 | Greenhalgh et al. |
| 9,463,036 B2 | 10/2016 | Brady et al. |
| 9,492,635 B2 | 11/2016 | Beasley et al. |
| 9,526,864 B2 | 12/2016 | Quick |
| 9,526,865 B2 | 12/2016 | Quick |
| 9,532,792 B2 | 1/2017 | Galdonik et al. |
| 9,545,464 B2 | 1/2017 | Roche et al. |
| 9,566,073 B2 | 2/2017 | Kassab et al. |
| 9,566,179 B2 | 2/2017 | Andreas et al. |
| 9,566,424 B2 | 2/2017 | Pessin |
| 9,579,116 B1 | 2/2017 | Nguyen et al. |
| 9,581,942 B1 | 2/2017 | Shippert |
| 9,616,213 B2 | 4/2017 | Furnish et al. |
| 9,636,206 B2 | 5/2017 | Nguyen et al. |
| 9,643,035 B2 | 5/2017 | Mastenbroek |
| 9,662,129 B2 | 5/2017 | Galdonik et al. |
| 9,700,332 B2 | 7/2017 | Marchand et al. |
| 9,717,488 B2 | 8/2017 | Kassab et al. |
| 9,717,514 B2 | 8/2017 | Martin et al. |
| 9,717,519 B2 | 8/2017 | Rosenbluth et al. |
| 9,744,024 B2 | 8/2017 | Nguyen et al. |
| 9,757,137 B2 | 9/2017 | Krolik et al. |
| 9,827,084 B2 | 11/2017 | Bonnette et al. |
| 9,827,364 B2 | 11/2017 | Peticca et al. |
| 9,844,386 B2 | 12/2017 | Nguyen et al. |
| 9,844,387 B2 | 12/2017 | Marchand et al. |
| 9,844,643 B2 | 12/2017 | Beasley et al. |
| 9,848,975 B2 | 12/2017 | Hauser |
| 9,849,014 B2 | 12/2017 | Kusleika |
| 9,884,387 B2 | 2/2018 | Plha |
| 9,937,321 B2 | 4/2018 | Welch et al. |
| 9,962,178 B2 | 5/2018 | Greenhalgh et al. |
| 9,980,813 B2 | 5/2018 | Eller |
| 9,999,493 B2 | 6/2018 | Nguyen et al. |
| 10,004,531 B2 | 6/2018 | Rosenbluth et al. |
| 10,010,335 B2 | 7/2018 | Greenhalgh et al. |
| 10,016,206 B1 | 7/2018 | Yang |
| 10,016,266 B2 | 7/2018 | Hauser |
| 10,028,759 B2 | 7/2018 | Wallace et al. |
| 10,045,790 B2 | 8/2018 | Cox et al. |
| 10,058,339 B2 | 8/2018 | Galdonik et al. |
| 10,098,651 B2 | 10/2018 | Marchand et al. |
| 10,130,385 B2 | 11/2018 | Farhangnia et al. |
| 10,130,795 B2 | 11/2018 | Parhangnia et al. |
| 10,179,224 B2 | 1/2019 | Yang et al. |
| 10,183,147 B2 | 1/2019 | Yang et al. |
| 10,183,159 B2 | 1/2019 | Nobles et al. |
| 10,188,829 B2 | 1/2019 | Beasley et al. |
| 10,195,320 B2 | 2/2019 | Fisher et al. |
| 10,226,263 B2 | 3/2019 | Look et al. |
| 10,238,406 B2 | 3/2019 | Cox et al. |
| 10,271,864 B2 | 4/2019 | Greenhalgh et al. |
| 10,327,883 B2 | 6/2019 | Yachia |
| 10,335,186 B2 | 7/2019 | Rosenbluth et al. |
| 10,342,571 B2 | 7/2019 | Marchand et al. |
| 10,349,960 B2 | 7/2019 | Quick |
| 10,383,644 B2 | 8/2019 | Molaei et al. |
| 10,383,983 B2 | 8/2019 | Aklog et al. |
| 10,384,034 B2 | 8/2019 | Carrison et al. |
| 10,426,510 B2 | 10/2019 | Farhangnia et al. |
| 10,426,644 B2 | 10/2019 | Shrivastava et al. |
| 10,441,745 B2 | 10/2019 | Yang et al. |
| 10,456,151 B2 | 10/2019 | Slee et al. |
| 10,456,555 B2 | 10/2019 | Carrison et al. |
| 10,471,234 B2 | 11/2019 | Taber |
| 10,478,535 B2 | 11/2019 | Ogle |
| 10,485,952 B2 | 11/2019 | Carrison et al. |
| 10,492,805 B2 | 12/2019 | Culbert et al. |
| 10,524,811 B2 | 1/2020 | Marchand et al. |
| 10,531,883 B1 | 1/2020 | Deville et al. |
| 10,537,710 B2 | 1/2020 | Jalgaonkar et al. |
| 10,561,440 B2 | 2/2020 | Look et al. |

(56) References Cited

U.S. PATENT DOCUMENTS

| 10,588,655 B2 | 3/2020 | Rosenbluth et al. |
| 10,648,268 B2 | 5/2020 | Jaffrey et al. |
| 10,661,053 B2 | 5/2020 | Yang et al. |
| 10,695,159 B2 | 6/2020 | Hauser |
| 10,709,471 B2 | 7/2020 | Rosenbluth et al. |
| 10,716,880 B2 | 7/2020 | Culbert et al. |
| 10,729,455 B2 | 8/2020 | Goyal et al. |
| 10,743,907 B2 | 8/2020 | Bruzzi et al. |
| 10,772,636 B2 | 9/2020 | Kassab et al. |
| 10,779,852 B2 | 9/2020 | Bruzzi et al. |
| 10,779,855 B2 | 9/2020 | Garrison |
| 10,792,056 B2 | 10/2020 | Vale et al. |
| 10,799,331 B2 | 10/2020 | Hauser |
| 10,799,671 B2 | 10/2020 | Shimada et al. |
| 10,813,663 B2 | 10/2020 | Bruzzi et al. |
| 10,828,061 B2 | 11/2020 | Bonnette et al. |
| 10,835,711 B2 | 11/2020 | Yang et al. |
| 10,874,421 B2 | 12/2020 | Bruzzi et al. |
| 10,912,577 B2 | 2/2021 | Marchand et al. |
| 10,926,060 B2 | 2/2021 | Stern et al. |
| 10,939,932 B1 | 3/2021 | Yang |
| 10,953,195 B2 | 3/2021 | Jalgaonkar et al. |
| 10,960,114 B2 | 3/2021 | Goisis |
| 10,967,111 B2 | 4/2021 | Iida |
| 10,994,063 B2 | 5/2021 | Fisher et al. |
| 11,000,682 B2 | 5/2021 | Merritt et al. |
| 11,013,523 B2 | 5/2021 | Arad Hadar |
| 11,058,445 B2 | 7/2021 | Cox et al. |
| 11,058,451 B2 | 7/2021 | Marchand et al. |
| 11,065,019 B1 | 7/2021 | Chou et al. |
| 11,065,028 B2 | 7/2021 | Parhangnia et al. |
| 11,147,571 B2 | 10/2021 | Cox et al. |
| 11,147,948 B2 | 10/2021 | Beasley et al. |
| 11,147,949 B2 | 10/2021 | Yang et al. |
| 11,154,314 B2 | 10/2021 | Quick |
| 11,166,703 B2 | 11/2021 | Kassab et al. |
| 11,185,664 B2 | 11/2021 | Carrison et al. |
| 11,197,684 B1 | 12/2021 | Ngo et al. |
| 11,213,356 B2 | 1/2022 | Tanner et al. |
| 11,224,450 B2 | 1/2022 | Chou et al. |
| 11,224,721 B2 | 1/2022 | Carrison et al. |
| 11,253,277 B2 | 2/2022 | Buck et al. |
| 11,259,821 B2 | 3/2022 | Buck et al. |
| 11,266,825 B2 | 3/2022 | Peter et al. |
| 11,278,307 B2 | 3/2022 | Bruzzi et al. |
| 11,305,094 B2 | 4/2022 | Carrison et al. |
| 11,317,939 B2 | 5/2022 | Bruzzi et al. |
| 11,337,714 B2 | 5/2022 | Ferrera et al. |
| 11,383,064 B2 | 7/2022 | Carrison et al. |
| 11,395,903 B2 | 7/2022 | Carrison et al. |
| 11,406,418 B2 | 8/2022 | Bruzzi et al. |
| 11,406,801 B2 | 8/2022 | Fojtik et al. |
| 11,419,621 B2 | 8/2022 | Goyal et al. |
| 11,433,218 B2 | 9/2022 | Quick et al. |
| 11,439,799 B2 | 9/2022 | Buck et al. |
| 11,457,936 B2 | 10/2022 | Buck et al. |
| 11,478,262 B2 | 10/2022 | Ngo et al. |
| 11,529,158 B2 | 12/2022 | Hauser |
| 11,541,184 B2 | 1/2023 | Han et al. |
| 11,553,935 B2 | 1/2023 | Buck et al. |
| 11,553,942 B2 | 1/2023 | Bonnette et al. |
| 11,554,005 B2 | 1/2023 | Merritt et al. |
| 11,559,382 B2 | 1/2023 | Merritt et al. |
| 11,576,691 B2 | 2/2023 | Chou et al. |
| 11,589,880 B2 | 2/2023 | Aklog et al. |
| 11,596,768 B2 | 3/2023 | Stern et al. |
| 11,607,483 B2 | 3/2023 | Iida |
| 11,633,272 B2 | 4/2023 | Buck et al. |
| 11,638,637 B2 | 5/2023 | Buck et al. |
| 11,642,209 B2 | 5/2023 | Merritt et al. |
| 11,648,028 B2 | 5/2023 | Rosenbluth et al. |
| 11,672,561 B2 | 6/2023 | Look et al. |
| 11,678,905 B2 | 6/2023 | Look et al. |
| 11,697,011 B2 | 7/2023 | Merritt et al. |
| 11,697,012 B2 | 7/2023 | Merritt et al. |
| 11,724,052 B2 | 8/2023 | White et al. |
| 11,730,925 B2 | 8/2023 | Saadat et al. |
| 11,744,691 B2 | 9/2023 | Merritt et al. |
| 11,806,033 B2 | 11/2023 | Marchand et al. |
| 11,819,228 B2 | 11/2023 | Buck et al. |
| 11,832,837 B2 | 12/2023 | Hauser |
| 11,832,838 B2 | 12/2023 | Hauser |
| 11,833,023 B2 | 12/2023 | Hauser |
| 11,839,393 B2 | 12/2023 | Hauser |
| 11,844,921 B2 | 12/2023 | Merritt et al. |
| 11,849,963 B2 | 12/2023 | Quick |
| 11,865,291 B2 | 1/2024 | Merritt et al. |
| 11,890,180 B2 | 2/2024 | Merritt et al. |
| 11,918,243 B2 | 3/2024 | Marchand et al. |
| 11,918,244 B2 | 3/2024 | Marchand et al. |
| 11,925,369 B2 | 3/2024 | Hauser |
| 11,937,834 B2 | 3/2024 | Dinh |
| 11,937,838 B2 | 3/2024 | Cox et al. |
| 11,963,861 B2 | 4/2024 | Strauss et al. |
| 11,969,178 B2 | 4/2024 | Hauser |
| 11,969,331 B2 | 4/2024 | Merritt et al. |
| 11,969,332 B2 | 4/2024 | Merritt et al. |
| 11,969,333 B2 | 4/2024 | Merritt et al. |
| 11,974,909 B2 | 5/2024 | Merritt et al. |
| 11,974,910 B2 | 5/2024 | Merritt et al. |
| 11,980,537 B2 | 5/2024 | Merritt et al. |
| 11,986,382 B2 | 5/2024 | Merritt et al. |
| 11,998,436 B2 | 6/2024 | Merritt et al. |
| 12,016,580 B2 | 6/2024 | Quick et al. |
| 12,023,057 B2 | 7/2024 | Hauser |
| 12,102,343 B2 | 10/2024 | Quick |
| 12,109,384 B2 | 10/2024 | Merritt et al. |
| 12,156,669 B2 | 12/2024 | Quick et al. |
| 12,239,333 B2 | 3/2025 | Quick et al. |
| 12,251,120 B2 | 3/2025 | Marchand et al. |
| 12,274,459 B2 | 4/2025 | Dihn |
| 12,310,608 B2 | 5/2025 | Marchand et al. |
| 2001/0004699 A1 | 6/2001 | Gittings et al. |
| 2001/0031981 A1 | 10/2001 | Evans et al. |
| 2001/0041881 A1 | 11/2001 | Sarge et al. |
| 2001/0041909 A1 | 11/2001 | Tsugita et al. |
| 2001/0049486 A1 | 12/2001 | Evans et al. |
| 2001/0049517 A1 | 12/2001 | Zadno-azizi et al. |
| 2001/0051810 A1 | 12/2001 | Dubrul et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0032455 A1 | 3/2002 | Boock et al. |
| 2002/0049452 A1 | 4/2002 | Kurz et al. |
| 2002/0095161 A1 | 7/2002 | Dhindsa |
| 2002/0095171 A1 | 7/2002 | Belef |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0151918 A1 | 10/2002 | Lafontaine et al. |
| 2002/0156457 A1 | 10/2002 | Fisher |
| 2002/0161392 A1 | 10/2002 | Dubrul |
| 2002/0169474 A1 | 11/2002 | Kusleika |
| 2002/0173819 A1 | 11/2002 | Leeflang et al. |
| 2002/0188276 A1 | 12/2002 | Evans et al. |
| 2003/0004536 A1 | 1/2003 | Boylan et al. |
| 2003/0023263 A1 | 1/2003 | Krolik et al. |
| 2003/0069601 A1 | 4/2003 | Nowakowski et al. |
| 2003/0083693 A1 | 5/2003 | Daniel et al. |
| 2003/0100919 A1 | 5/2003 | Hopkins et al. |
| 2003/0114875 A1 | 6/2003 | Sjostrom |
| 2003/0116731 A1 | 6/2003 | Hartley |
| 2003/0125663 A1 | 7/2003 | Coleman et al. |
| 2003/0135151 A1 | 7/2003 | Deng |
| 2003/0135230 A1 | 7/2003 | Massey et al. |
| 2003/0135258 A1 | 7/2003 | Andreas et al. |
| 2003/0144672 A1 | 7/2003 | Gellman et al. |
| 2003/0153873 A1 | 8/2003 | Luther et al. |
| 2003/0153973 A1 | 8/2003 | Soun et al. |
| 2003/0168068 A1 | 9/2003 | Poole et al. |
| 2003/0176884 A1 | 9/2003 | Berrada et al. |
| 2003/0191425 A1 | 10/2003 | Rosenblatt et al. |
| 2003/0191516 A1 | 10/2003 | Weldon et al. |
| 2003/0208224 A1 | 11/2003 | Broome |

(56) References Cited

U.S. PATENT DOCUMENTS

| | | |
|---|---|---|
| 2003/0216774 A1 | 11/2003 | Larson |
| 2003/0225379 A1 | 12/2003 | Schaffer et al. |
| 2004/0019310 A1 | 1/2004 | Hogendijk |
| 2004/0039351 A1 | 2/2004 | Barrett |
| 2004/0039412 A1 | 2/2004 | Isshiki et al. |
| 2004/0068288 A1 | 4/2004 | Palmer et al. |
| 2004/0073243 A1 | 4/2004 | Sepetka et al. |
| 2004/0098033 A1 | 5/2004 | Leeflang et al. |
| 2004/0102807 A1 | 5/2004 | Kusleika et al. |
| 2004/0122359 A1 | 6/2004 | Wenz et al. |
| 2004/0127936 A1 | 7/2004 | Salahieh et al. |
| 2004/0133232 A1 | 7/2004 | Rosenbluth et al. |
| 2004/0138525 A1 | 7/2004 | Saadat et al. |
| 2004/0138692 A1 | 7/2004 | Phung et al. |
| 2004/0167567 A1 | 8/2004 | Cano et al. |
| 2004/0199201 A1 | 10/2004 | Kellett et al. |
| 2004/0199202 A1 | 10/2004 | Dubrul et al. |
| 2004/0260344 A1 | 12/2004 | Lyons et al. |
| 2004/0267272 A1 | 12/2004 | Henniges et al. |
| 2005/0004534 A1 | 1/2005 | Lockwood et al. |
| 2005/0033172 A1 | 2/2005 | Dubrul et al. |
| 2005/0038468 A1 | 2/2005 | Panetta et al. |
| 2005/0054995 A1 | 3/2005 | Barzell et al. |
| 2005/0055047 A1 | 3/2005 | Greenhalgh |
| 2005/0080398 A1 | 4/2005 | Markel et al. |
| 2005/0085769 A1 | 4/2005 | MacMahon et al. |
| 2005/0085826 A1 | 4/2005 | Nair et al. |
| 2005/0085846 A1 | 4/2005 | Carrison et al. |
| 2005/0085849 A1 | 4/2005 | Sepetka et al. |
| 2005/0119668 A1 | 6/2005 | Teague et al. |
| 2005/0131387 A1 | 6/2005 | Pursley |
| 2005/0177132 A1 | 8/2005 | Lentz et al. |
| 2005/0187570 A1 | 8/2005 | Nguyen et al. |
| 2005/0203605 A1 | 9/2005 | Dolan |
| 2005/0283165 A1 | 12/2005 | Gadberry |
| 2005/0283166 A1 | 12/2005 | Greenhalgh et al. |
| 2005/0283186 A1 | 12/2005 | Berrada et al. |
| 2006/0020286 A1 | 1/2006 | Niermann |
| 2006/0042786 A1 | 3/2006 | West |
| 2006/0047286 A1 | 3/2006 | West |
| 2006/0074401 A1 | 4/2006 | Ross |
| 2006/0079787 A1 | 4/2006 | Whiting et al. |
| 2006/0085952 A1 | 4/2006 | Kaneko et al. |
| 2006/0089533 A1 | 4/2006 | Ziegler et al. |
| 2006/0100662 A1 | 5/2006 | Daniel et al. |
| 2006/0149219 A1 | 7/2006 | Calderon |
| 2006/0155305 A1 | 7/2006 | Freudenthal et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0217664 A1 | 9/2006 | Hattler et al. |
| 2006/0224177 A1 | 10/2006 | Finitsis |
| 2006/0229645 A1 | 10/2006 | Bonnette et al. |
| 2006/0247500 A1 | 11/2006 | Voegele et al. |
| 2006/0253145 A1 | 11/2006 | Lucas |
| 2006/0264905 A1 | 11/2006 | Eskridge et al. |
| 2006/0276874 A1 | 12/2006 | Wilson et al. |
| 2006/0282111 A1 | 12/2006 | Morsi |
| 2006/0293696 A1 | 12/2006 | Fahey et al. |
| 2007/0010787 A1 | 1/2007 | Hackett et al. |
| 2007/0038225 A1 | 2/2007 | Osborne |
| 2007/0060911 A1 | 3/2007 | Webster et al. |
| 2007/0093744 A1 | 4/2007 | Elmaleh |
| 2007/0112374 A1 | 5/2007 | Paul, Jr. et al. |
| 2007/0118165 A1 | 5/2007 | DeMello et al. |
| 2007/0149996 A1 | 6/2007 | Coughlin |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0213765 A1 | 9/2007 | Adams et al. |
| 2007/0233043 A1 | 10/2007 | Dayton et al. |
| 2007/0255252 A1 | 11/2007 | Mehta |
| 2007/0288054 A1 | 12/2007 | Tanaka et al. |
| 2008/0015541 A1 | 1/2008 | Rosenbluth et al. |
| 2008/0033467 A1 | 2/2008 | Miyamoto et al. |
| 2008/0087853 A1 | 4/2008 | Kees |
| 2008/0088055 A1 | 4/2008 | Ross |
| 2008/0157017 A1 | 7/2008 | Macatangay et al. |
| 2008/0167678 A1 | 7/2008 | Morsi |
| 2008/0183136 A1 | 7/2008 | Lenker et al. |
| 2008/0228209 A1 | 9/2008 | DeMello et al. |
| 2008/0234715 A1 | 9/2008 | Pesce et al. |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0294096 A1 | 11/2008 | Uber, III et al. |
| 2008/0300466 A1 | 12/2008 | Gresham |
| 2008/0312681 A1 | 12/2008 | Ansel et al. |
| 2009/0018550 A1 | 1/2009 | Poll |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0069828 A1 | 3/2009 | Martin et al. |
| 2009/0076417 A1 | 3/2009 | Jones |
| 2009/0082857 A1 | 3/2009 | Lashinski et al. |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0192495 A1 | 7/2009 | Ostrovsky et al. |
| 2009/0281525 A1 | 11/2009 | Harding et al. |
| 2009/0292307 A1 | 11/2009 | Razack |
| 2009/0299393 A1 | 12/2009 | Martin et al. |
| 2009/0312786 A1 | 12/2009 | Trask et al. |
| 2010/0016837 A1 | 1/2010 | Howat |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0087850 A1 | 4/2010 | Razack |
| 2010/0094201 A1 | 4/2010 | Mallaby |
| 2010/0106081 A1 | 4/2010 | Brandeis |
| 2010/0114017 A1 | 5/2010 | Lenker et al. |
| 2010/0114113 A1 | 5/2010 | Dubrul et al. |
| 2010/0121312 A1 | 5/2010 | Gielenz et al. |
| 2010/0137846 A1 | 6/2010 | Desai et al. |
| 2010/0190156 A1 | 7/2010 | Van Wordragen et al. |
| 2010/0204712 A1 | 8/2010 | Mallaby |
| 2010/0217276 A1 | 8/2010 | Garrison et al. |
| 2010/0228221 A1 | 9/2010 | Kassab et al. |
| 2010/0249815 A1 | 9/2010 | Jantzen et al. |
| 2010/0268264 A1 | 10/2010 | Bonnette et al. |
| 2010/0297577 A1 | 11/2010 | Cohen |
| 2010/0318178 A1 | 12/2010 | Rapaport et al. |
| 2011/0009950 A1 | 1/2011 | Grandfield et al. |
| 2011/0034986 A1 | 2/2011 | Chou et al. |
| 2011/0034987 A1 | 2/2011 | Kennedy |
| 2011/0054405 A1 | 3/2011 | Whiting et al. |
| 2011/0060212 A1 | 3/2011 | Slee et al. |
| 2011/0071503 A1 | 3/2011 | Takagi et al. |
| 2011/0087173 A1* | 4/2011 | Sibbitt, Jr. .......... A61B 10/0233 |
| | | 604/207 |
| 2011/0118817 A1 | 5/2011 | Gunderson et al. |
| 2011/0125181 A1 | 5/2011 | Brady et al. |
| 2011/0144592 A1 | 6/2011 | Wong et al. |
| 2011/0152823 A1 | 6/2011 | Mohiuddin et al. |
| 2011/0152889 A1 | 6/2011 | Ashland |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |
| 2011/0190806 A1 | 8/2011 | Wittens |
| 2011/0196309 A1 | 8/2011 | Wells |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1 | 10/2011 | Sakata et al. |
| 2011/0251629 A1 | 10/2011 | Galdonik et al. |
| 2011/0264132 A1 | 10/2011 | Strauss et al. |
| 2011/0264133 A1 | 10/2011 | Hanlon et al. |
| 2011/0265681 A1 | 11/2011 | Allen et al. |
| 2011/0288529 A1 | 11/2011 | Fulton |

(56) References Cited

U.S. PATENT DOCUMENTS

| | | |
|---|---|---|
| 2011/0288572 A1 | 11/2011 | Martin |
| 2011/0309037 A1 | 12/2011 | Lee |
| 2011/0319917 A1 | 12/2011 | Ferrera et al. |
| 2012/0059309 A1 | 3/2012 | di Palma et al. |
| 2012/0059356 A1 | 3/2012 | di Palma et al. |
| 2012/0083824 A1 | 4/2012 | Berrada et al. |
| 2012/0083868 A1 | 4/2012 | Shrivastava |
| 2012/0089216 A1 | 4/2012 | Rapaport et al. |
| 2012/0095448 A1 | 4/2012 | Kajii |
| 2012/0101480 A1 | 4/2012 | Ingle et al. |
| 2012/0101510 A1 | 4/2012 | Lenker et al. |
| 2012/0109109 A1 | 5/2012 | Kajii |
| 2012/0138832 A1 | 6/2012 | Townsend |
| 2012/0143123 A1 | 6/2012 | Agnew |
| 2012/0143239 A1 | 6/2012 | Aklog et al. |
| 2012/0165919 A1 | 6/2012 | Cox et al. |
| 2012/0172918 A1 | 7/2012 | Fifer et al. |
| 2012/0179181 A1 | 7/2012 | Straub et al. |
| 2012/0197277 A1 | 8/2012 | Stinis |
| 2012/0232655 A1 | 9/2012 | Lorrison et al. |
| 2012/0271105 A1 | 10/2012 | Nakamura et al. |
| 2012/0271231 A1 | 10/2012 | Agrawal |
| 2012/0277788 A1 | 11/2012 | Cattaneo |
| 2012/0310166 A1 | 12/2012 | Huff |
| 2013/0030460 A1 | 1/2013 | Marks et al. |
| 2013/0035628 A1 | 2/2013 | Garrison et al. |
| 2013/0046332 A1 | 2/2013 | Jones et al. |
| 2013/0066348 A1 | 3/2013 | Fiorella et al. |
| 2013/0092012 A1 | 4/2013 | Marchand et al. |
| 2013/0096571 A1 | 4/2013 | Massicotte et al. |
| 2013/0102996 A1 | 4/2013 | Strauss |
| 2013/0116708 A1 | 5/2013 | Ziniti et al. |
| 2013/0116721 A1 | 5/2013 | Takagi et al. |
| 2013/0123705 A1 | 5/2013 | Holm et al. |
| 2013/0126559 A1 | 5/2013 | Cowan et al. |
| 2013/0144326 A1 | 6/2013 | Brady et al. |
| 2013/0150793 A1 | 6/2013 | Beissel et al. |
| 2013/0165871 A1 | 6/2013 | Fiorella et al. |
| 2013/0184703 A1 | 7/2013 | Shireman et al. |
| 2013/0190701 A1 | 7/2013 | Kirn |
| 2013/0197454 A1 | 8/2013 | Shibata et al. |
| 2013/0197567 A1 | 8/2013 | Brady et al. |
| 2013/0204297 A1 | 8/2013 | Melsheimer et al. |
| 2013/0226196 A1 | 8/2013 | Smith |
| 2013/0270161 A1 | 10/2013 | Kumar et al. |
| 2013/0281788 A1 | 10/2013 | Garrison |
| 2013/0289608 A1 | 10/2013 | Tanaka et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046133 A1 | 2/2014 | Nakamura et al. |
| 2014/0046243 A1 | 2/2014 | Ray et al. |
| 2014/0052161 A1 | 2/2014 | Cully et al. |
| 2014/0074144 A1 | 3/2014 | Shrivastava et al. |
| 2014/0121672 A1 | 5/2014 | Folk |
| 2014/0155830 A1 | 6/2014 | Bonnette et al. |
| 2014/0155908 A1 | 6/2014 | Rosenbluth et al. |
| 2014/0155980 A1 | 6/2014 | Turjman |
| 2014/0163615 A1 | 6/2014 | Gadlage et al. |
| 2014/0180055 A1 | 6/2014 | Glynn et al. |
| 2014/0180397 A1 | 6/2014 | Gerberding et al. |
| 2014/0188127 A1 | 7/2014 | Dubrul et al. |
| 2014/0188143 A1 | 7/2014 | Martin et al. |
| 2014/0222070 A1 | 8/2014 | Belson et al. |
| 2014/0236219 A1 | 8/2014 | Dubrul et al. |
| 2014/0243882 A1 | 8/2014 | Ma |
| 2014/0257253 A1 | 9/2014 | Jemison |
| 2014/0257363 A1 | 9/2014 | Lippert |
| 2014/0276403 A1 | 9/2014 | Follmer et al. |
| 2014/0276592 A1 | 9/2014 | Mottola et al. |
| 2014/0296868 A1 | 10/2014 | Garrison et al. |
| 2014/0303658 A1 | 10/2014 | Bonnette et al. |
| 2014/0318354 A1 | 10/2014 | Thompson et al. |
| 2014/0324091 A1 | 10/2014 | Rosenbluth et al. |
| 2014/0330286 A1 | 11/2014 | Wallace et al. |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick et al. |
| 2015/0018860 A1 | 1/2015 | Quick |
| 2015/0018929 A1 | 1/2015 | Martin et al. |
| 2015/0025555 A1 | 1/2015 | Sos |
| 2015/0032144 A1 | 1/2015 | Holloway |
| 2015/0059908 A1 | 3/2015 | Mollen |
| 2015/0088190 A1 | 3/2015 | Jensen |
| 2015/0119862 A1 | 4/2015 | Cajamarca et al. |
| 2015/0127035 A1 | 5/2015 | Trapp et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0164666 A1 | 6/2015 | Johnson et al. |
| 2015/0173782 A1 | 6/2015 | Garrison et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0283309 A1 | 10/2015 | Look et al. |
| 2015/0305756 A1 | 10/2015 | Rosenbluth |
| 2015/0305759 A1 | 10/2015 | St. George et al. |
| 2015/0305859 A1 | 10/2015 | Eller |
| 2015/0314050 A1 | 11/2015 | Beer |
| 2015/0327875 A1 | 11/2015 | Look et al. |
| 2015/0352325 A1 | 12/2015 | Quick |
| 2015/0360001 A1 | 12/2015 | Quick |
| 2015/0366690 A1 | 12/2015 | Lumauig |
| 2015/0374391 A1 | 12/2015 | Quick |
| 2016/0008014 A1 | 1/2016 | Rosenbluth |
| 2016/0022293 A1 | 1/2016 | Dubrul et al. |
| 2016/0030708 A1 | 2/2016 | Casiello et al. |
| 2016/0038267 A1 | 2/2016 | Allen et al. |
| 2016/0058540 A1 | 3/2016 | Don Michael |
| 2016/0074627 A1 | 3/2016 | Cottone |
| 2016/0106353 A1 | 4/2016 | Schuetz et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0113666 A1 | 4/2016 | Quick |
| 2016/0128857 A1 | 5/2016 | Kao |
| 2016/0135829 A1 | 5/2016 | Holoehwost et al. |
| 2016/0143721 A1 | 5/2016 | Rosenbluth |
| 2016/0151605 A1 | 6/2016 | Welch et al. |
| 2016/0192912 A1 | 7/2016 | Kassab et al. |
| 2016/0206344 A1 | 7/2016 | Bruzzi et al. |
| 2016/0220741 A1 | 8/2016 | Garrison et al. |
| 2016/0220795 A1 | 8/2016 | Korkuch et al. |
| 2016/0228134 A1 | 8/2016 | Martin et al. |
| 2016/0262774 A1 | 9/2016 | Honda |
| 2016/0262790 A1 | 9/2016 | Rosenbluth et al. |
| 2016/0287276 A1 | 10/2016 | Cox et al. |
| 2016/0367285 A1 | 12/2016 | Sos |
| 2017/0014560 A1 | 1/2017 | Minskoff et al. |
| 2017/0021130 A1 | 1/2017 | Dye |
| 2017/0035445 A1 | 2/2017 | Nguyen et al. |
| 2017/0037548 A1 | 2/2017 | Lee |
| 2017/0042571 A1 | 2/2017 | Levi |
| 2017/0049942 A1 | 2/2017 | Conlan et al. |
| 2017/0056032 A1 | 3/2017 | Look et al. |
| 2017/0058623 A1 | 3/2017 | Jaffrey et al. |
| 2017/0079672 A1 | 3/2017 | Quick |

(56) References Cited

U.S. PATENT DOCUMENTS

| | | |
|---|---|---|
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0105745 A1 | 4/2017 | Rosenbluth et al. |
| 2017/0112513 A1 | 4/2017 | Marchand et al. |
| 2017/0112514 A1 | 4/2017 | Marchand et al. |
| 2017/0113005 A1 | 4/2017 | Linder et al. |
| 2017/0143359 A1 | 5/2017 | Nguyen et al. |
| 2017/0143880 A1 | 5/2017 | Luxon et al. |
| 2017/0143938 A1 | 5/2017 | Ogle et al. |
| 2017/0165468 A1 | 6/2017 | Nobles et al. |
| 2017/0172591 A1 | 6/2017 | Ulm, III |
| 2017/0189041 A1 | 7/2017 | Cox et al. |
| 2017/0196576 A1 | 7/2017 | Long et al. |
| 2017/0209162 A1 | 7/2017 | Sperry et al. |
| 2017/0233908 A1 | 8/2017 | Kroczynski et al. |
| 2017/0238951 A1 | 8/2017 | Yang et al. |
| 2017/0252057 A1 | 9/2017 | Bonnette et al. |
| 2017/0265878 A1 | 9/2017 | Marchand et al. |
| 2017/0281204 A1 | 10/2017 | Garrison et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0319221 A1 | 11/2017 | Chu |
| 2017/0325839 A1 | 11/2017 | Rosenbluth et al. |
| 2017/0340867 A1 | 11/2017 | Accisano, II |
| 2017/0348014 A1 | 12/2017 | Wallace et al. |
| 2018/0014840 A1 | 1/2018 | Panian |
| 2018/0042623 A1 | 2/2018 | Batiste |
| 2018/0042624 A1 | 2/2018 | Greenhalgh et al. |
| 2018/0042626 A1 | 2/2018 | Greenhalgh et al. |
| 2018/0055999 A1 | 3/2018 | Bare et al. |
| 2018/0064453 A1 | 3/2018 | Garrison et al. |
| 2018/0064454 A1 | 3/2018 | Losordo et al. |
| 2018/0070968 A1 | 3/2018 | Wallace et al. |
| 2018/0078707 A1 | 3/2018 | Loonan |
| 2018/0092652 A1 | 4/2018 | Marchand et al. |
| 2018/0104404 A1 | 4/2018 | Ngo-Chu |
| 2018/0105963 A1 | 4/2018 | Quick |
| 2018/0125512 A1 | 5/2018 | Nguyen et al. |
| 2018/0184912 A1 | 7/2018 | Al-Ali |
| 2018/0193043 A1 | 7/2018 | Marchand et al. |
| 2018/0235742 A1 | 8/2018 | Fields et al. |
| 2018/0236205 A1 | 8/2018 | Krautkremer et al. |
| 2018/0250498 A1 | 9/2018 | Stern et al. |
| 2018/0256177 A1 | 9/2018 | Cooper et al. |
| 2018/0256178 A1 | 9/2018 | Cox et al. |
| 2018/0280623 A1 | 10/2018 | Pilkington et al. |
| 2018/0289394 A1 | 10/2018 | Shah |
| 2018/0296240 A1 | 10/2018 | Rosenbluth et al. |
| 2018/0338770 A1 | 11/2018 | Mogi et al. |
| 2018/0339130 A1 | 11/2018 | Ogle |
| 2018/0344339 A1 | 12/2018 | Cox et al. |
| 2018/0353195 A1 | 12/2018 | Sigmon, Jr. et al. |
| 2018/0361116 A1 | 12/2018 | Quick et al. |
| 2019/0000492 A1 | 1/2019 | Casey et al. |
| 2019/0015298 A1 | 1/2019 | Beatty et al. |
| 2019/0046219 A1 | 2/2019 | Marchand et al. |
| 2019/0070401 A1 | 3/2019 | Merritt et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0150959 A1 | 5/2019 | Cox et al. |
| 2019/0216476 A1 | 7/2019 | Barry et al. |
| 2019/0223893 A1 | 7/2019 | Gilvarry et al. |
| 2019/0231373 A1 | 8/2019 | Quick |
| 2019/0239910 A1 | 8/2019 | Brady et al. |
| 2019/0321071 A1 | 10/2019 | Marchand et al. |
| 2019/0328411 A1 | 10/2019 | Vale et al. |
| 2019/0336142 A1 | 11/2019 | Torrie et al. |
| 2019/0336148 A1 | 11/2019 | Greenhalgh et al. |
| 2019/0365395 A1 | 12/2019 | Tran et al. |
| 2019/0366036 A1 | 12/2019 | Jalgaonkar et al. |
| 2019/0366049 A1 | 12/2019 | Hannon et al. |
| 2019/0374239 A1 | 12/2019 | Martin et al. |
| 2020/0009301 A1 | 1/2020 | Yee |
| 2020/0022711 A1 | 1/2020 | Look et al. |
| 2020/0030579 A1 | 1/2020 | Taber |
| 2020/0046368 A1 | 2/2020 | Merritt et al. |
| 2020/0046940 A1 | 2/2020 | Carrison et al. |
| 2020/0054861 A1 | 2/2020 | Korkuch et al. |
| 2020/0069889 A1* | 3/2020 | Lin ...................... A61M 5/486 |
| 2020/0078029 A1 | 3/2020 | Hansen et al. |
| 2020/0113412 A1 | 4/2020 | Jensen |
| 2020/0121334 A1 | 4/2020 | Galdonik et al. |
| 2020/0129741 A1 | 4/2020 | Kawwas et al. |
| 2020/0187596 A1 | 6/2020 | Krout et al. |
| 2020/0324079 A1 | 10/2020 | Jalgaonkar et al. |
| 2021/0022843 A1 | 1/2021 | Hauser |
| 2021/0038385 A1 | 2/2021 | Popp et al. |
| 2021/0113224 A1 | 4/2021 | Dinh |
| 2021/0128182 A1 | 5/2021 | Teigen et al. |
| 2021/0128184 A1 | 5/2021 | Fulkerson et al. |
| 2021/0128185 A1 | 5/2021 | Nguyen et al. |
| 2021/0137667 A1 | 5/2021 | Sonnette et al. |
| 2021/0138193 A1 | 5/2021 | Garrison et al. |
| 2021/0138194 A1 | 5/2021 | Carrison et al. |
| 2021/0154433 A1 | 5/2021 | Casey et al. |
| 2021/0186537 A1 | 6/2021 | Buck et al. |
| 2021/0186541 A1 | 6/2021 | Thress |
| 2021/0205577 A1 | 7/2021 | Jalgaonkar et al. |
| 2021/0236148 A1 | 8/2021 | Marchand et al. |
| 2021/0290925 A1 | 9/2021 | Merritt et al. |
| 2021/0315596 A1 | 10/2021 | Buck et al. |
| 2021/0315598 A1 | 10/2021 | Buck et al. |
| 2021/0316127 A1 | 10/2021 | Buck et al. |
| 2021/0330344 A1 | 10/2021 | Rosenbluth et al. |
| 2021/0378692 A1 | 12/2021 | Xiang et al. |
| 2021/0378694 A1 | 12/2021 | Thress et al. |
| 2021/0393278 A1 | 12/2021 | O'Malley et al. |
| 2021/0404464 A1 | 12/2021 | Patoskie |
| 2022/0000505 A1 | 1/2022 | Hauser |
| 2022/0000506 A1 | 1/2022 | Hauser |
| 2022/0000507 A1 | 1/2022 | Hauser |
| 2022/0015798 A1 | 1/2022 | Marchand et al. |
| 2022/0021197 A1 | 1/2022 | Zhao et al. |
| 2022/0022898 A1 | 1/2022 | Cox et al. |
| 2022/0033888 A1 | 2/2022 | Schnall-Levin et al. |
| 2022/0039815 A1* | 2/2022 | Thress ............. A61M 5/31505 |
| 2022/0047281 A1 | 2/2022 | Kamalova |
| 2022/0125451 A1 | 4/2022 | Hauser |
| 2022/0142638 A1 | 5/2022 | Enright et al. |
| 2022/0151647 A1 | 5/2022 | Dolendo et al. |
| 2022/0152355 A1 | 5/2022 | Dolendo et al. |
| 2022/0160381 A1 | 5/2022 | Hauser |
| 2022/0160382 A1 | 5/2022 | Hauser |
| 2022/0160383 A1 | 5/2022 | Hauser |
| 2022/0211400 A1 | 7/2022 | Cox et al. |
| 2022/0211992 A1 | 7/2022 | Merritt et al. |
| 2022/0226555 A1 | 7/2022 | Sunenshine et al. |
| 2022/0240959 A1 | 8/2022 | Quick |
| 2022/0296797 A1 | 9/2022 | Chawla |
| 2022/0331554 A1 | 10/2022 | Beasley et al. |
| 2022/0346800 A1 | 11/2022 | Merritt et al. |
| 2022/0346813 A1 | 11/2022 | Quick |
| 2022/0346814 A1 | 11/2022 | Quick |
| 2022/0347455 A1 | 11/2022 | Merritt et al. |
| 2022/0362512 A1 | 11/2022 | Quick et al. |
| 2022/0370761 A1 | 11/2022 | Chou et al. |
| 2022/0378445 A1 | 12/2022 | Culbert et al. |
| 2022/0378446 A1 | 12/2022 | Culbert et al. |
| 2022/0378447 A1 | 12/2022 | Culbert et al. |
| 2022/0378448 A1 | 12/2022 | Culbert et al. |
| 2022/0378451 A1 | 12/2022 | Goyal et al. |
| 2022/0378460 A1 | 12/2022 | Culbert et al. |
| 2022/0387072 A1 | 12/2022 | Look et al. |
| 2023/0015259 A1 | 1/2023 | Buck et al. |
| 2023/0046775 A1 | 2/2023 | Quick |
| 2023/0047682 A1 | 2/2023 | Deaton et al. |

(56)         References Cited

U.S. PATENT DOCUMENTS

| | | | |
|---|---|---|---|
| 2023/0052964 A1 | 2/2023 | Singh et al. |
| 2023/0059721 A1 | 2/2023 | Chou et al. |
| 2023/0062809 A1 | 3/2023 | Merritt et al. |
| 2023/0063701 A1 | 3/2023 | Horowitz et al. |
| 2023/0070120 A1 | 3/2023 | Cox et al. |
| 2023/0122587 A1 | 4/2023 | Chou et al. |
| 2023/0149034 A1 | 5/2023 | Aklog et al. |
| 2023/0181200 A1 | 6/2023 | Deville et al. |
| 2023/0200970 A1 | 6/2023 | Merritt et al. |
| 2023/0210554 A1 | 7/2023 | Bruzzi et al. |
| 2023/0218310 A1 | 7/2023 | Scheinblum et al. |
| 2023/0218313 A1 | 7/2023 | Rosenbluth et al. |
| 2023/0218383 A1 | 7/2023 | Merritt et al. |
| 2023/0233311 A1 | 7/2023 | Merritt et al. |
| 2023/0240705 A1 | 8/2023 | Rosenbluth et al. |
| 2023/0240706 A1 | 8/2023 | Rosenbluth et al. |
| 2023/0241302 A1 | 8/2023 | Merritt et al. |
| 2023/0248380 A1 | 8/2023 | Long et al. |
| 2023/0248498 A1 | 8/2023 | Buck et al. |
| 2023/0248499 A1 | 8/2023 | Buck et al. |
| 2023/0248500 A1 | 8/2023 | Buck et al. |
| 2023/0248501 A1 | 8/2023 | Buck et al. |
| 2023/0248502 A1 | 8/2023 | Buck et al. |
| 2023/0248503 A1 | 8/2023 | Buck et al. |
| 2023/0248504 A1 | 8/2023 | Buck et al. |
| 2023/0270991 A1 | 8/2023 | Merritt et al. |
| 2023/0310137 A1 | 10/2023 | Merritt et al. |
| 2023/0310138 A1 | 10/2023 | Merritt et al. |
| 2023/0310751 A1 | 10/2023 | Merritt et al. |
| 2023/0320834 A1 | 10/2023 | Merritt et al. |
| 2023/0329734 A1 | 10/2023 | Marchand et al. |
| 2023/0338130 A1 | 10/2023 | Merritt et al. |
| 2023/0338131 A1 | 10/2023 | Merritt et al. |
| 2023/0355256 A1 | 11/2023 | Dinh |
| 2023/0355259 A1 | 11/2023 | Marchand et al. |
| 2023/0355371 A1 | 11/2023 | Buck et al. |
| 2023/0355938 A1 | 11/2023 | Merritt et al. |
| 2023/0363776 A1 | 11/2023 | Quick |
| 2023/0363883 A1 | 11/2023 | Merritt et al. |
| 2023/0389932 A1 | 12/2023 | Ozenne et al. |
| 2023/0390045 A1 | 12/2023 | Merritt et al. |
| 2024/0016505 A1 | 1/2024 | Horowitz et al. |
| 2024/0016993 A1 | 1/2024 | Haslam et al. |
| 2024/0058113 A1 | 2/2024 | Strauss et al. |
| 2024/0074771 A1 | 3/2024 | Quick et al. |
| 2024/0081857 A1 | 3/2024 | Luong et al. |
| 2024/0082540 A1 | 3/2024 | Brodt et al. |
| 2024/0108366 A1 | 4/2024 | Horowitz et al. |
| 2024/0131235 A1 | 4/2024 | Horowitz et al. |
| 2024/0157041 A1 | 5/2024 | Zikry et al. |
| 2024/0173042 A1 | 5/2024 | Yang et al. |
| 2024/0198072 A1 | 6/2024 | Merritt et al. |
| 2024/0207593 A1 | 6/2024 | Merritt et al. |
| 2024/0225674 A1 | 7/2024 | Dederich et al. |
| 2024/0245501 A1 | 7/2024 | Strauss et al. |
| 2024/0245502 A1 | 7/2024 | Merritt et al. |
| 2024/0261492 A1 | 8/2024 | Yang et al. |
| 2024/0285387 A1 | 8/2024 | Merritt et al. |
| 2024/0299053 A1 | 9/2024 | Hauser |
| 2024/0307082 A1 | 9/2024 | Marchand et al. |
| 2024/0307166 A1 | 9/2024 | Merritt et al. |
| 2024/0341779 A1 | 10/2024 | Dinh |
| 2024/0341788 A1 | 10/2024 | Cox et al. |
| 2024/0407905 A1 | 12/2024 | Merrit et al. |
| 2024/0415626 A1 | 12/2024 | Merrit et al. |
| 2024/0415627 A1 | 12/2024 | Merrit et al. |
| 2025/0017618 A1 | 1/2025 | Truty et al. |
| 2025/0049456 A1 | 2/2025 | Cox et al. |
| 2025/0064464 A1 | 2/2025 | Barkley et al. |
| 2025/0090182 A1 | 3/2025 | Slaughter et al. |
| 2025/0177625 A1 | 6/2025 | Merritt |

FOREIGN PATENT DOCUMENTS

| | | |
|---|---|---|
| CN | 102014772 | 4/2011 |
| CN | 102186427 | 9/2011 |
| CN | 102316809 | 1/2012 |
| CN | 103764049 | 4/2014 |
| CN | 103932756 | 7/2014 |
| CN | 104068910 | 10/2014 |
| CN | 106178227 | 12/2016 |
| CN | 106470728 | 3/2017 |
| CN | 108348319 | 7/2018 |
| CN | 110312481 | 10/2019 |
| CN | 110420046 | 11/2019 |
| CN | 110652645 | 1/2020 |
| CN | 111281482 | 6/2020 |
| CN | 215082793 | 12/2021 |
| DE | 1116001 | 10/1961 |
| DE | 102017004383 | 7/2018 |
| EP | 0914807 | 5/1999 |
| EP | 0956072 | 10/2001 |
| EP | 1254634 | 11/2002 |
| EP | 1991138 | 11/2008 |
| EP | 2073864 | 7/2009 |
| EP | 2203209 | 7/2010 |
| EP | 2209509 | 7/2010 |
| EP | 2394680 | 12/2011 |
| EP | 1867290 | 2/2013 |
| EP | 2624905 | 8/2013 |
| EP | 2540328 | 10/2013 |
| EP | 2726135 | 5/2014 |
| EP | 2908783 | 8/2015 |
| EP | 2939704 | 11/2015 |
| EP | 2942624 | 11/2015 |
| EP | 2967614 | 1/2016 |
| EP | 2977072 | 1/2016 |
| EP | 2367482 | 10/2016 |
| EP | 3102274 | 12/2016 |
| EP | 3122412 | 2/2017 |
| EP | 3340896 | 3/2017 |
| EP | 3202340 | 8/2017 |
| EP | 3302624 | 4/2018 |
| EP | 3305220 | 4/2018 |
| EP | 3305221 | 4/2018 |
| EP | 3311875 | 4/2018 |
| EP | 2231256 | 5/2018 |
| EP | 3344157 | 7/2018 |
| EP | 3417893 | 12/2018 |
| EP | 3419528 | 1/2019 |
| EP | 3422963 | 1/2019 |
| EP | 3439561 | 2/2019 |
| EP | 3449967 | 3/2019 |
| EP | 3544528 | 10/2019 |
| EP | 3583972 | 12/2019 |
| EP | 3589348 | 1/2020 |
| EP | 3603690 | 2/2020 |
| EP | 3612264 | 2/2020 |
| EP | 3620204 | 3/2020 |
| EP | 3013404 | 4/2020 |
| EP | 4039205 | 8/2022 |
| EP | 4072613 | 10/2022 |
| EP | 4076611 | 10/2022 |
| EP | 4079344 | 10/2022 |
| EP | 4137070 | 2/2023 |
| EP | 4144310 | 3/2023 |
| EP | 4252992 | 10/2023 |
| EP | 4419159 | 8/2024 |
| GB | 1588072 | 4/1981 |
| GB | 2498349 | 7/2013 |
| JP | H6190049 | 7/1994 |
| JP | H07323090 A | 12/1995 |
| JP | 2001522631 | 5/1999 |
| JP | 2000175925 | 6/2000 |
| JP | 2004097807 | 4/2004 |
| JP | 2005511989 | 4/2005 |
| JP | 2005-095242 | 6/2005 |
| JP | 2005230132 | 9/2005 |
| JP | 2005323702 | 11/2005 |
| JP | 2006094876 | 4/2006 |
| JP | 2007-222658 | 9/2007 |

(56) References Cited

FOREIGN PATENT DOCUMENTS

| | | |
|---|---|---|
| JP | 2011526820 | 1/2010 |
| JP | 2011517424 | 6/2011 |
| JP | 05694718 | 4/2015 |
| JP | 2015208685 | 11/2015 |
| JP | 2016513505 | 5/2016 |
| JP | 2016104212 | 6/2016 |
| JP | 2017533051 | 11/2017 |
| JP | 2018525088 | 9/2018 |
| JP | 2003033359 | 2/2023 |
| JP | 7253376 | 3/2023 |
| JP | 7324264 | 8/2023 |
| JP | 7491974 | 5/2024 |
| WO | WO1997017889 | 5/1997 |
| WO | WO1998024501 | 6/1998 |
| WO | WO9833443 | 8/1998 |
| WO | WO9838920 | 9/1998 |
| WO | WO9839053 | 9/1998 |
| WO | WO9851237 | 11/1998 |
| WO | WO1999044542 | 9/1999 |
| WO | WO9951140 | 10/1999 |
| WO | WO0032118 | 6/2000 |
| WO | WO2000053120 | 9/2000 |
| WO | WO0202162 | 1/2002 |
| WO | WO2002055146 | 7/2002 |
| WO | WO20002055146 | 7/2002 |
| WO | WO03015840 | 2/2003 |
| WO | WO2004018916 | 3/2004 |
| WO | WO2004093696 | 11/2004 |
| WO | WO2005046736 | 5/2005 |
| WO | WO2006029270 | 3/2006 |
| WO | WO2006110186 | 10/2006 |
| WO | WO2006124307 | 11/2006 |
| WO | WO2007092820 | 8/2007 |
| WO | WO2009082513 | 7/2009 |
| WO | WO2009086482 | 7/2009 |
| WO | WO2009105710 | 8/2009 |
| WO | WO2009126747 | 10/2009 |
| WO | WO2009155571 | 12/2009 |
| WO | WO2010002549 | 1/2010 |
| WO | WO2010010545 | 1/2010 |
| WO | WO2010023671 | 3/2010 |
| WO | WO2010049121 | 5/2010 |
| WO | WO2010095712 | 8/2010 |
| WO | WO2010102307 | 9/2010 |
| WO | WO2011032712 | 3/2011 |
| WO | WO2011054531 | 5/2011 |
| WO | WO2011073176 | 6/2011 |
| WO | WO2012009675 | 1/2012 |
| WO | WO2012011097 | 1/2012 |
| WO | WO2012049652 | 4/2012 |
| WO | WO2012065748 | 5/2012 |
| WO | WO2012114633 | 8/2012 |
| WO | WO2012120490 | 9/2012 |
| WO | WO2012162437 | 11/2012 |
| WO | WO2014047650 | 3/2014 |
| WO | WO2014081892 | 5/2014 |
| WO | WO2014139845 | 9/2014 |
| WO | WO2015006782 | 1/2015 |
| WO | WO2015061365 | 4/2015 |
| WO | WO2015121424 | 8/2015 |
| WO | WO2015179329 | 11/2015 |
| WO | WO2015189354 | 12/2015 |
| WO | WO2015191646 | 12/2015 |
| WO | WO2016014955 | 1/2016 |
| WO | WO2016071524 | 5/2016 |
| WO | WO2017024258 | 2/2017 |
| WO | WO2017033182 | 3/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018049317 | 3/2018 |
| WO | WO2018065092 | 4/2018 |
| WO | WO2018080590 | 5/2018 |
| WO | WO2018100445 | 6/2018 |
| WO | WO2018148174 | 8/2018 |
| WO | WO2019010318 | 1/2019 |
| WO | WO2019050765 | 3/2019 |
| WO | WO2019064306 | 4/2019 |
| WO | WO2019075444 | 4/2019 |
| WO | WO2019094456 | 5/2019 |
| WO | WO2019173475 | 9/2019 |
| WO | WO2019222117 | 11/2019 |
| WO | WO2019246240 | 12/2019 |
| WO | WO2020036809 | 2/2020 |
| WO | WO2020142381 | 7/2020 |
| WO | WO2021067134 | 4/2021 |
| WO | WO2021076954 | 4/2021 |
| WO | WO2021127202 | 6/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |
| WO | WO2022261448 | 12/2022 |
| WO | WO2023018819 | 2/2023 |
| WO | WO2023069874 | 4/2023 |
| WO | WO2003048616 | 6/2023 |
| WO | WO2023115032 | 6/2023 |
| WO | WO2023137341 | 7/2023 |
| WO | WO2023143700 | 8/2023 |
| WO | WO2023147353 | 8/2023 |
| WO | WO2023154612 | 8/2023 |
| WO | WO2023192925 | 10/2023 |
| WO | WO2023215779 | 11/2023 |
| WO | WO2023239706 | 12/2023 |
| WO | WO2024006482 | 1/2024 |
| WO | WO2024054988 | 3/2024 |
| WO | WO2024059695 | 3/2024 |
| WO | WO2024103036 | 5/2024 |
| WO | WO2024151629 | 7/2024 |
| WO | WO2024238472 | 11/2024 |
| WO | WO2025014517 | 1/2025 |
| WO | WO2025059542 | 3/2025 |
| WO | WO2025106851 | 5/2025 |
| WO | WO2025111572 | 5/2025 |
| WO | WO2025117864 | 6/2025 |

OTHER PUBLICATIONS

US 12,115,056 B2, 10/2024, Merritt et al. (withdrawn)

Gibbs, et al., "Temporary Stent as a bail-out device during percutaneous transluminal coronary angioplasty: preliminary clinical experience," British Heart Journal, 1994, 71:372-377, Oct. 12, 1993, 6 pgs.

Gupta, S. et al., "Acute Pulmonary Embolism Advances in Treatment", JAPI, Association of Physicians India, Mar. 2008, vol. 56, 185-191.

International Search Report and Written Opinion for International App. No. PCT/US13/61470, mailed Jan. 17, 2014, 7 pages.

International Search Report and Written Opinion for International App. No. PCT/US2014/046567, mailed Nov. 3, 2014, 13 pages.

International Search Report and Written Opinion for International App. No. PCT/US2014/061645, mailed Jan. 23, 2015, 15 pages.

International Search Report for International App. No. PCT/US13/71101, mailed Mar. 31, 2014, 4 pages.

Konstantinides, S. et al., "Pulmonary embolism hotline 2012—Recent and expected trials", Thrombosis and Haemostasis, Jan. 9, 2013:33; 43-50.

Konstantinides, S. et al., "Pulmonary embolism: risk assessment and management", European Society of Cardiology; European Heart Journal, Sep. 7, 2012:33, 3014-3022.

Kucher, N. et al., "Percutaneous Catheter Thrombectomy Device for Acute Pulmonary Embolism: In Vitro and in Vivo Testing", Circulation, Sep. 2005:112:e28-e32.

Kucher, N., "Catheter Interventions in Massive Pulmonary Embolism", Cardiology Rounds, Mar. 2006 vol. 10, Issue 3, 6 pages.

(56)        References Cited

OTHER PUBLICATIONS

Kucher, N. et al., "Management of Massive Pulmonary Embolism", Radiology, Sep. 2005:236:3 852-858.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.

Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.

Lee, L. et al., "Massive pulmonary embolism: review of management strategies with a focus on catheter-based techniques", Expert Rev. Cardiovasc. Ther. 8(6), 863-873 (2010).

Liu, S. et al., "Massive Pulmonary Embolism: Treatment with the Rotarex Thrombectomy System", Cardiovascular Interventional Radiology; 2011: 34:106-113.

Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.

Reekers, J. et al., "Mechanical Thrombectomy for Early Treatment of Massive Pulmonary Embolism", CardioVascular and Interventional Radiology, 2003: 26:246-250.

Schmitz-Rode et al., "New Mesh Basket for Percutaneous Removal of Wall-Adherent Thrombi in Dialysis Shunts," Cardiovasc Intervent Radiol 16:7-10 1993 4 pgs.

Schmitz-Rode et al., "Temporary Pulmonary Stent Placement as Emergency Treatment of Pulmonary Embolism," Journal of the American College of Cardiology, vol. 48, No. 4, 2006 (5 pgs.).

Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.

Spiotta, A et al., "Evolution of thrombectomy approaches and devices for acute stroke: a technical review." J NeuroIntervent Surg 2015, 7, pp. 7 pages.

Svilaas, T. et al., "Thrombus Aspiration During Primary Percutaneous Coronary Intervention." The New England Journal of Medicine, 2008, vol. 358, No. 6, 11 pages.

Tapson, V., "Acute Pulmonary Embolism", The New England Journal of Medicine, Mar. 6, 2008:358:2037-52.

The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.

Truong et al., "Mechanical Thrombectomy of Iliocaval Thrombosis Using a Protective Expandable Sheath," Cardiovasc Intervent Radiol 27-254-258, 2004, 5 pgs.

Turk et al., "ADAPT FAST study: a direct aspiration first pass technique for acute stroke thrombectomy." J NeuroIntervent Surg, vol. 6, 2014, 6 pages.

Uflacker, R., "Interventional Therapy for Pulmonary Embolism", Journal of Vascular and Interventional Radiology, Feb. 2001: 12:147-164.

Verma, R., MD et al. "Evaluation of a Newly Developed Percutaneous Thrombectomy Basket Device in Sheep With Central Pulmonary Embolisms", *Investigative Radiology*, Oct. 2006, 41, 729-734.

International Search Report and Written Opinion for International App. No. PCT/US2015/034987 filed Jun. 9, 2015, Applicant: Inceptus Medical, LLC, Date of Mailing: Sep. 17, 2015, 12 pages.

International Search Report and Written Opinion for International App. No. PCT/US2016/067628 filed Dec. 19, 2016, Applicant: Inari Medical, Inc., Date of Mailing: Apr. 10, 2017, 11 pages.

Goldhaber, S. et al. "Percutaneous Mechanical Thrombectomy for Acute Pulmonary Embolism—A Double-Edged Sword," American College of CHEST Physicians, Aug. 2007, 132:2, 363-372.

Goldhaber, S., "Advanced treatment strategies for acute pulmonary embolism, including thrombolysis and embolectomy," Journal of Thrombosis and Haemostasis, 2009: 7 (Suppl. 1): 322-327.

International Search Report and Written Opinion for International App. No. PCT/US2017/029696, Date of Filing: Apr. 26, 2017, Applicant: Inari Medical, Inc., Date of Mailing: Sep. 15, 2017, 19 pages.

International Search Report and Written Opinion for International App. No. PCT/US2016/058536, Date of Filing: Oct. 24, 2016, Applicant: Inari Medical, Inc., Date of Mailing: Mar. 13, 2017, 14 pages.

International Search Report and Written Opinion for International App. No. PCT/US2018/048786, Date of Filing: Aug. 30, 2018, Applicant: Inari Medical, Inc., Date of Mailing: Dec. 13, 2018, 12 pages.

International Search Report and Written Opinion for International App. No. PCT/US2018/055780, Date of Filing: Oct. 13, 2018, Applicant: Inceptus Medical LLC., Date of Mailing: Jan. 22, 2019, 8 pages.

International Search Report and Written Opinion for International App. No. PCT/US2019/045794, Date of Filing: Aug. 8, 2019, Applicant: Inari Medical, Inc., Date of Mailing: Nov. 1, 2019, 17 pages.

International Search Report and Written Opinion for International App. No. PCT/US2020/056067, Date of Filing: Oct. 16, 2020; Applicant: Inari Medical, Inc., Date of Mailing: Jan. 22, 2021, 8 pages.

International Search Report and Written Opinion for International App. No. PCT/US2020/055645, Date of Filing: Dec. 17, 2020; Applicant: Inari Medical, Inc., Date of Mailing: Apr. 14, 2021, 12 pages.

Vorwerk, D. MD, et al., "Use of a Temporary Caval Filter to Assist Percutaneous Iliocaval Thrombectomy: Experimental Results." SCVIR, 1995, 4 pages.

WIKIPEDIA; Embolectomy; retrieved from the internet: https://en.wikipedia.org/wiki/Embolectomy; 4 pgs.; retrieved/printed: Mar. 24, 2016.

O'Sullivan; Thrombolysis versus thrombectomy in acute deep vein thrombosis; Interventional Cardiology; 3(5); pp. 589-596; Oct. 2011.

Capture Vascular Systems; (company website); retrieved from the internet: http://www.capturevascular.com; 3 pgs.; retrieved/printed: Mar. 24, 2016.

Edwards LifeSciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.

Boston Scientific; Fetch(TM) 2 Aspiration Catheter (product information); retrieved from the internet: http://www.bostonscientific.com/en-us/products/thrombectomy-systems/fetch2-aspiration-catheter.html; 2 pgs.; retrieved/printed: Mar. 24, 2016.

Penumbra, Inc.; Indigo® System (product information); retrieved from the internet: http://www.penumbrainc.com/peripherallpercutaneous-thromboembolectomy/indigo-system; 7 pgs.; retrieved/printed: Mar. 24, 2016.

YouTube; Merci Retrieval System X Series Animation; uploaded Mar. 16, 2009 (product information); posted on May 7, 2009 by SSMDePAUL, time 1:09, retrieved from the internet: https://www.youtube.com/watch?v=MGX7deuFkhc; 3 pgs.; retrieved/printed: Mar. 24, 2016.

COVIDIEN; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.

(56)                References Cited

OTHER PUBLICATIONS

International Search Report and Written Opinion for International App. No. PCT/US21/35965, Date of Filing: Jun. 4, 2021, Applicant: Inari Medical, Inc., Date of Mailing: Sep. 28, 2021, 12 pages.
International Search Report and Written Opinion for International App. No. PCT/US21/45072 Date of Filing: Aug. 6, 2021, Applicant: Inari Medical, Inc., Date of Mailing: Jan. 20, 2022, 10 pages.
International Search Report and Written Opinion for International App. No. PCT/US21/58793; Date of Filing: Nov. 10, 2021, Applicant: Inari Medical, Inc., Date of Mailing: Mar. 16, 2022, 13 pages.
International Search Report and Written Opinion for International App. No. PCT/US21/59718; Date of Filing: Nov. 17, 2021, Applicant: Inari Medical, Inc., Date of Mailing: Mar. 22, 2022, 13 pages.
International Search Report and Written Opinion for International App. No. PCT/US21/59735; Date of Filing: Nov. 17, 2021, Applicant: Inari Medical, Inc., Date of Mailing: Mar. 22, 2022, 11 pages.
International Search Report and Written Opinion for International App. No. PCT/US23/60502; Date of Filing: Jan. 11, 2023, Applicant: Inari Medical, Inc., Date of Mailing: May 25, 2023, 9 pages.
International Search Report and Written Opinion for International App. No. PCT/US23/61256; Date of Filing: Jan. 25, 2023, Applicant: Inari Medical, Inc., Date of Mailing: Jun. 7, 2023, 8 pages.
Gross et al., "Dump the pump: manual aspiration thrombectomy (MAT) with a syringe is technically effective, expeditious, and cost-efficient," J NeuroIntervent Surg, 2018, 4 pages.
English translation of Japanese Office Action mailed Jun. 7, 2023 for Japanese Application No. 2021- 507564, 7 pages.
European Office Action received for EP Application No. 16876941.2, Applicant: Inari Medical, Inc, Date of Mailing: Jul. 18, 2023, 6 pages.
International Search Report and Written Opinion for International App. No. PCT/US23/60927; Date of Filing: Jan. 19, 2023, Applicant: Inari Medical, Inc., Date of Mailing: Jul. 20, 2023, 12 pages.
Extended European Search Report issued for EP Application No. 20877370.5, Date of Mailing: Oct. 17, 2023, 11 pages.
International Search Report and Written Opinion for International App. No. PCT/US23/65128; Date of Filing: Mar. 30, 2023, Applicant: Inari Medical, Inc., Date of Mailing: Nov. 14, 2023, 14 pages.
International Search Report and Written Opinion for International App. No. PCT/US23/66538; Date of Filing: May 3, 2023, Applicant: Inari Medical, Inc., Date of Mailing: Jan. 4, 2024, 14 pages.
English translation of Japanese Office Action received for JP Application No. 2022-574456, Applicant: Inari Medical, Inc, Date of Mailing: Jan. 23, 2024, 12 pages.
Chinese First Office Action received for CN Application No. 201980067623.1, Applicant: Inari Medical, Inc., Date of Mailing: Jan. 31, 2024, 10 pages.
International Search Report and Written Opinion for International App. No. PCT/US23/73765; Date of Filing: Sep. 8, 2023, Applicant: Inari Medical, Inc., Date of Mailing: Feb. 28, 2024, 7 pages.
International Search Report and Written Opinion for International App. No. PCT/US23/69892; Date of Filing: Jul. 10, 2023, Applicant: Inari Medical, Inc., Date of Mailing: Feb. 29, 2024, 12 pages.
English translation of Japanese Office Action mailed Jan. 19, 2024 for Japanese Application No. 2022-160947, 8 pages.
International Search Report and Written Opinion for International App. No. PCT/US2024/010875; Applicant: Inari Medical, Inc., Date of Mailing: Apr. 26, 2024, 15 pages.
International Search Report and Written Opinion for International App. No. PCT/US2023/079428; Applicant: Inari Medical, Inc., Date of Mailing: May 29, 2024, 18 pages.
Extended European Search Report for European Application No. 21818772.2, Applicant: Inari Medical, Inc., Date of Mailing: May 10, 9 pages.

Chinese Office Action received for Application No. 202111061740.2, Applicant: Inari Medical, Inc, Date of Mailing: May 23, 2024, 15 pages.
English translation of Japanese Office Action mailed Jun. 25, 2024 for Japanese Application No. 2022- 574456, 5 pages.
Japanese Office Action mailed Jul. 8, 2024 for Japanese Application No. 2022-522892, 14 pages.
Chinese first Office Action mailed May 10, 2024 for Chinese Application No. 202080087833.X, 11 pages.
Partial Supplementary European Search Report received for European Application No. 21852966.7; Applicant: Inari Medical, Inc., Date of Mailing: Jul. 23, 2024, 12 pages.
Japanese Office Action mailed Aug. 2, 2024 for Japanese Application No. 2023-213724, 3 pages.
English Translation of Japanese Office Action mailed Jul. 23, 2024 for Japanese Application No. 2022- 535535, 11 pages.
Extended European Search Report received for European Application No. 21895504.5; Applicant: Inari Medical, Inc., Date of Mailing: Aug. 16, 2024, 10 pages.
English translation of Japanese Office Action mailed Sep. 17, 2024 for Japanese Application No. 2023-203650, 6 pages.
English machine translation of Japanese Office Action mailed Oct. 10, 2024 for Japanese Application No. 2022-522892, 11 pages.
International Search Report and Written Opinion for International App. No. PCT/US2024/043504; Applicant: Inari Medical, Inc., Date of Mailing: Nov. 12, 2024, 12 pages.
International Search Report and Written Opinion for International App. No. PCT/US2024/037570; Applicant: Inari Medical, Inc., Date of Mailing: Nov. 20, 2024, 12 pages.
International Search Report and Written Opinion for International App. No. PCT/US2024/046723; Applicant: Inari Medical, Inc., Date of Mailing: Nov. 27, 2024, 11 pages.
English translation of Chinese Office Action mailed Jan. 22, 2025 for Chinese Application No. 202210842779.6, 17 pages.
Extended European Search Report received for European Application No. 24209030.6; Applicant: Inari Medical, Inc., Date of Mailing: Feb. 3, 2025, 7 pages.
International Search Report and Written Opinion for International App. No. PCT/US2024/057919; Applicant: Inari Medical, Inc., Date of Mailing: Mar. 28, 2025, 13 pages.
English translation of Chinese Second Office Action mailed Apr. 24, 2025 for Chinese Application No. 202080097026.6, 10 pages.
International Search Report for International Application No. PCT/US2023/026648, mailed on Dec. 19, 2023, 6 pages.
Written Opinion of the International Searching Authority for International Application No. PCT/US2023/026648, dated Dec. 19, 2023, 31 pages.
International Search Report and Written Opinion for International App. No. PCT/US2024/057143; Applicant: Inari Medical, Inc., Date of Mailing: Feb. 10, 2025, 9 pages.
Bayer HealthCare, 'Our Next Generation Aspiration Catheter.' Fetch 2 Catheter Specifications, Feb. 2013, 2 pages.
Medtronic, Solitaire X, Revascularization Device. http://www.ev3.net/neuro/intl/remodeling-devices/solitaire-ab.htm. 6 pages, (2019).
International Search Report and Written Opinion for International App. No. PCT/US2023/074169; Applicant: Inari Medical, Inc., Date of Mailing: May 1, 2024, 12 pages.
English translation of Japanese Office Action for Japanese Application No. 2023-507628 mailed Apr. 23, 2025, 8 pages.
English translation of Japanese Office Action for Japanese Application No. 2024-064603 mailed May 16, 2025, 4 pages.
International Search Report and Written Opinion for International App. No. PCT/US2024/056178; Applicant: Inari Medical, Inc., Date of Mailing: Mar. 24, 2025, 13 pages.

* cited by examiner

1120

1130

1144    1140        1142       1160

1120     1130         1160

1140   1144    1142

AUTOMATIC LOCKING AND UNLOCKING VACUUM SYRINGES, AND ASSOCIATED SYSTEMS AND METHODS

CROSS-REFERENCE TO RELATED APPLICATION

This application claims the benefit of U.S. Provisional Patent Application No. 63/599,648, filed Nov. 16, 2023, and titled "AUTOMATIC LOCKING AND UNLOCKING VACUUM SYRINGES, AND ASSOCIATED SYSTEMS AND METHODS," which is incorporated herein by reference in its entirety.

TECHNICAL FIELD

The present technology generally relates to automatically locking and unlocking syringes, such as for use in systems for treating occlusive (e.g., clot) material within a human patient, and associated systems and methods.

BACKGROUND

Thromboembolic events are characterized by an occlusion of a blood vessel. Thromboembolic disorders, such as stroke, pulmonary embolism, heart attack, peripheral thrombosis, atherosclerosis, and the like, affect many people. These disorders are a major cause of morbidity and mortality.

When an artery is occluded by occlusive material, such as clot material, tissue ischemia develops. The ischemia will progress to tissue infarction if the occlusion persists. However, infarction does not develop or is greatly limited if the flow of blood is reestablished rapidly. Failure to reestablish blood flow can accordingly lead to the loss of limb, angina pectoris, myocardial infarction, stroke, or even death.

In the venous circulation, occlusive material can also cause serious harm. Blood clots can develop in the large veins of the legs and pelvis, a common condition known as deep venous thrombosis (DVT). DVT commonly occurs where there is a propensity for stagnated blood (e.g., long-distance air travel, immobility, etc.) and clotting (e.g., cancer; recent surgery, such as orthopedic surgery, etc.). DVT can obstruct drainage of venous blood from the legs, leading to swelling, ulcers, pain, and infection. DVT can also create a reservoir in which blood clots can collect and then travel to other parts of the body, including the heart, lungs, brain (which may cause a stroke), abdominal organs, and/or extremities.

In the pulmonary circulation, occlusive material can cause harm by obstructing pulmonary arteries—a condition known as pulmonary embolism (PE). If the obstruction is upstream, in the main or large branch pulmonary arteries, it can severely compromise total blood flow within the lungs, and therefore the entire body, and result in low blood pressure and shock. If the obstruction is downstream, in large to medium pulmonary artery branches, it can prevent a significant portion of the lung from participating in the exchange of gases to the blood resulting in low blood oxygen and buildup of blood carbon dioxide.

Various systems exist for performing a thrombectomy or removing occlusive material to reestablish blood flow within a patient. Some of these systems use (i) a syringe or other pressure source to generate and store a vacuum and (ii) a fluid control device, such as a stopcock, to apply the vacuum to a catheter to aspirate the occlusive material. To maintain the vacuum pressure generated in the syringe before opening the fluid control device, a plunger of the syringe may be selectively or automatically locked in a withdrawn position. However, such syringes require a user input to lock and/or unlock the plunger.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

Figure 1:
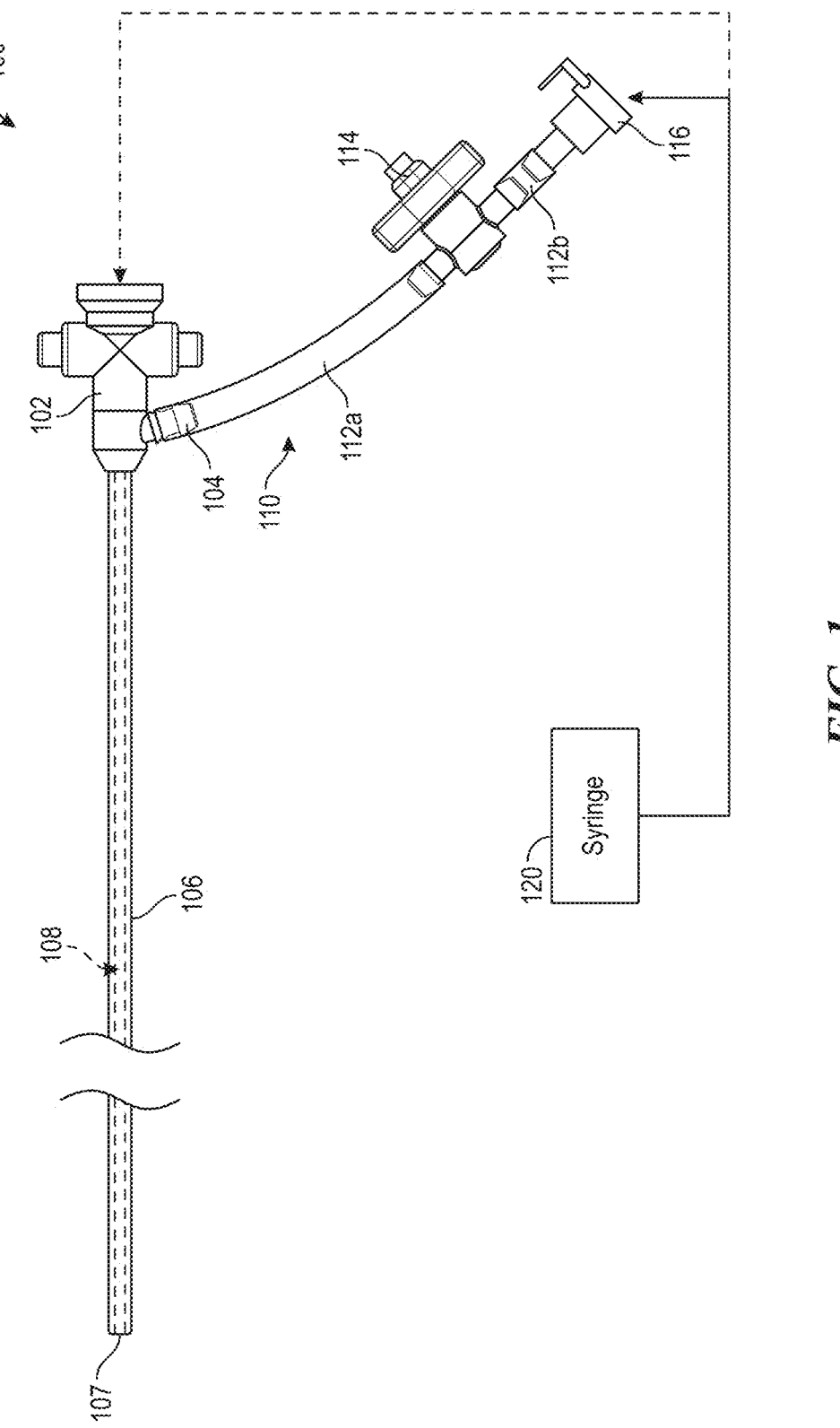
FIG. 1 is a partially schematic side view of a clot treatment system in accordance with embodiments of the present technology.

The present technology is generally directed to syringes for use in clot treatment systems, and associated systems and methods. In some embodiments, a syringe in accordance with the present technology can include a barrel, a plunger assembly slidably positioned within the barrel, and a locking assembly coupled to the barrel. The syringe is configured to (i) automatically lock the plunger assembly to the locking assembly when the plunger assembly is withdrawn through the barrel with a vacuum in the barrel, (ii) automatically unlock the plunger assembly from the locking assembly when the barrel no longer experiences vacuum and/or experiences negligible vacuum, and/or (iii) inhibit or even prevent automatic locking of the plunger assembly to the locking assembly when the plunger assembly is withdrawn through the barrel with no and/or negligible vacuum within the barrel. In some aspects of the present technology, the automatic-locking and automatic-unlocking syringe can simplify a clot removal procedure using the syringe by not requiring user input to either lock or unlock the position of the plunger assembly relative to the barrel during the clot removal procedure.

In some embodiments, an automatic-locking and automatic-unlocking syringe comprises a barrel, a plunger assembly slidably positioned within the barrel, and a locking assembly coupled to the barrel. The plunger assembly can be movable between a first position and a second position. The plunger assembly can be configured to be withdrawn through the barrel to generate vacuum pressure in the barrel. The plunger assembly can be configured to move from the first position to the second position in response to the vacuum pressure, and to move from the second position to the first position in response to the vacuum pressure being released. The plunger assembly can be configured to lock to the locking assembly in the second position such that the locking assembly inhibits movement of the plunger assembly through the barrel, and to unlock from the locking assembly in the first position such that the locking assembly permits movement of the plunger assembly through the barrel.

In some embodiments, an automatic-locking and automatic-unlocking syringe comprises a barrel and a plunger assembly slidably positioned within the barrel. The plunger assembly can comprise (i) a handle assembly including a first shaft having a distal portion, (ii) a seal assembly including a second shaft and a seal head coupled to the second shaft and having a scaling member positioned to sealingly engage the barrel, and (iii) a biasing member operably coupling the first shaft to the second shaft. The handle assembly can be configured to be withdrawn relative to the barrel to withdraw the seal assembly and the sealing member through the barrel to generate vacuum pressure within the barrel. The vacuum pressure can generate a vacuum force on the seal assembly greater than a biasing force of the biasing member such that the biasing member compresses and the seal head moves away from the distal portion of the first shaft.

In some embodiments, an automatic-locking and automatic-unlocking syringe comprises a barrel and a plunger assembly slidably positioned within the barrel. The plunger assembly can include a handle assembly and a seal assembly. The handle assembly can include a first shaft having a distal portion and a locking recess formed at the distal portion. The seal assembly can include a shield member. The seal assembly can be movable relative to the handle assembly between (i) a first position in which the shield member radially shields the locking recess and (ii) a second position in which the shield member is axially spaced apart from the locking recess.

Certain details are set forth in the following description and in FIGS. 1-15 to provide a thorough understanding of various embodiments of the present technology. In other instances, well-known structures, materials, operations, and/or systems often associated with intravascular procedures, clot removal procedures, clot treatment systems, clot treatment devices, fluid control devices, syringes, vacuum-locking syringes, blood-filtering syringes, catheters, and/or the like are not shown or described in detail in the following disclosure to avoid unnecessarily obscuring the description of the various embodiments of the technology. Those of ordinary skill in the art will recognize, however, that the present technology can be practiced without one or more of the details set forth herein, and/or with other structures, methods, components, and so forth. Moreover, although many of the devices and systems are described herein in the context of removing and/or treating clot material, the present technology can be used to remove and/or treat other unwanted material in addition or alternatively to clot material, such as thrombi, emboli, plaque, intimal hyperplasia, post-thrombotic scar tissue, etc. Accordingly, the terms "clot" and "clot material" as used herein can refer to any of the foregoing materials and/or the like.

The terminology used below is to be interpreted in its broadest reasonable manner, even though it is being used in conjunction with a detailed description of certain examples of embodiments of the technology. Indeed, certain terms may even be emphasized below; however, any terminology intended to be interpreted in any restricted manner will be overtly and specifically defined as such in this Detailed Description section.

The accompanying Figures depict embodiments of the present technology and are not intended to be limiting of its scope unless expressly indicated. The sizes of various depicted elements are not necessarily drawn to scale, and these various elements may be enlarged to improve legibility. Component details may be abstracted in the Figures to exclude details such as position of components and certain precise connections between such components when such details are unnecessary for a complete understanding of how to make and use the present technology. Many of the details, dimensions, angles and other features shown in the Figures are merely illustrative of particular embodiments of the disclosure. Accordingly, other embodiments can have other details, dimensions, angles and features without departing from the present technology. In addition, those of ordinary skill in the art will appreciate that further embodiments of the present technology can be practiced without several of the details described below.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," and the like are not meant to limit the referenced component to a specific orientation. It will be appreciated that such designations refer to the orientation of the referenced component as illustrated in the Figures; the systems of the present technology can be used in any orientation suitable to the user.

In the Figures, identical reference numbers identify identical, or at least generally similar, elements. To facilitate the discussion of any particular element, the most significant digit or digits of any reference number refers to the Figure in which that element is first introduced. For example, tubing assembly 110 is first introduced and discussed with reference to FIG. 1.

To the extent any materials incorporated herein by reference conflict with the present disclosure, the present disclosure controls.

FIG. 1 is a partially schematic side view of a clot treatment system 100 ("the system 100") in accordance with embodiments of the present technology. The system 100 can also be referred to as an aspiration assembly, a vascular access system, a clot removal system, a thrombectomy system, and/or the like. In the illustrated embodiment, the system 100 includes a tubing assembly 110 fluidly coupled to a catheter 106 via a valve 102. In some embodiments, the catheter 106 is an elongate member (e.g., a sheath, a shaft) configured to be inserted into and through a patient's vasculature and used to, for example, remove or otherwise treat clot material therein. In other embodiments, the catheter 106 can be an introducer sheath configured to be inserted through the skin and tissue tract of the patient to provide an access site through which other components (e.g., other catheters used to treat clot material) can traverse to easily access the vasculature. Accordingly, while referred to as "catheter 106," the catheter 106 can comprise an introducer sheath, an access sheath, and/or another type of elongate member configured to be inserted through the skin and tissue tract and/or to traverse the vasculature of a patient. The catheter 106 can be a large bore catheter, having, for example, a size equal to or greater than 16 French (Fr), such as 20 Fr, 22 Fr, 24 Fr, 26 Fr, 28 Fr, 30 Fr, 32 Fr, and/or the like. In general, the system 100 (i) can include features generally similar in structure and/or function, or identical in structure and/or function, to those of the clot treatment systems described in detail in U.S. patent application Ser. No. 16/536,185, now U.S. Pat. No. 11,559,382, filed Aug. 8, 2019, and titled "SYSTEM FOR TREATING EMBOLISM AND ASSOCIATED DEVICES AND METHODS," which is incorporated herein by reference in its entirety, and/or (ii) can be used to treat/remove clot material from a patient (e.g., a human patient) using any of the methods described in detail therein.

The catheter 106 further defines a lumen 108 (shown in dashed line in FIG. 1) extending entirely therethrough, e.g., from the valve 102 to a distal terminus 107 of the catheter 106. The catheter 106 can have varying lengths, flexibilities, shapes, thicknesses, and/or other properties along its length. For example, the catheter 106 can comprise one or more coils, braids, and/or other structures positioned between one or more liner layers (e.g., an inner liner layer and an outer liner layer). In some embodiments, the catheter 106 can include several features generally similar or identical in structure and/or function to any of the catheters described in (i) U.S. patent application Ser. No. 17/529,018, titled "CATHETERS HAVING SHAPED DISTAL PORTIONS, AND ASSOCIATED SYSTEMS AND METHODS," and filed Nov. 17, 2021, (ii) U.S. patent application Ser. No. 17/529,064, titled "CATHETERS HAVING STEERABLE DISTAL PORTIONS, AND ASSOCIATED SYSTEMS AND METHODS," and filed Nov. 17, 2021, (iii) U.S. patent application Ser. No. 18/159,507, titled "ASPIRATION CATHETERS HAVING GROOVED INNER SURFACE, AND ASSOCIATED SYSTEM AND METHODS," and filed Jan. 25, 2023, and/or (iv) U.S. patent application Ser.

No. 18/463,960, titled "CATHETERS HAVING MULTIPLE COIL LAYERS, AND ASSOCIATED SYSTEMS AND METHODS," and filed Sep. 8, 2023, each of which is incorporated by reference herein in its entirety.

The valve 102 is fluidly coupled to the lumen 108 of the catheter 106 and can be integral with or coupled to the catheter 106 such that these components move together. In some embodiments, the valve 102 is a hemostasis valve that is configured to maintain hemostasis during a clot treatment procedure by preventing fluid flow in a proximal direction through the valve 102 as various components such as dilators, delivery sheaths, pull members, guidewires, interventional devices, other aspiration catheters, and so on are inserted through the valve 102 to be delivered through the catheter 106 to a treatment site in a blood vessel. The valve 102 can include a branch or side port 104 configured to fluidly couple the lumen 108 of the catheter 106 to the tubing assembly 110. In some embodiments, the valve 102 can be a valve of the type disclosed in U.S. patent application Ser. No. 16/536,185, titled "HEMOSTASIS VALVES AND METHODS OF USE," and filed Aug. 30, 2018, which is incorporated herein by reference in its entirety.

In the illustrated embodiment, the tubing assembly 110 fluidly couples the catheter 106 to a syringe 120. The syringe 120 can be configured to generate (e.g., form, create, charge, build-up) a vacuum (e.g., negative relative pressure) and store the vacuum for subsequent application to the catheter 106. Further details of the syringe 120 are described in detail below with reference to FIGS. 2A-9. The tubing assembly 110 can include one or more tubing sections 112 (individually labeled as a first tubing section 112a and a second tubing section 112b), at least one valve or fluid control device 114, and at least one connector 116 (e.g., a Toomey tip connector) for fluidly coupling the tubing assembly 110 to the syringe 120 and/or other suitable components. In some embodiments, the connector 116 is a quick-release connector (e.g., a quick disconnect fitting) that enables rapid coupling/decoupling of the catheter 106 and the fluid control device 114 to/from the syringe 120. The tubing assembly 110 and the catheter 106 can have a same or substantially same inner dimension to, for example, define a lumen or flow path of uniform or substantially uniform diameter extending from the distal terminus 107 of the catheter to the syringe 120. In some embodiments, the fluid control device 114 is fluidly coupled to (i) the side port 104 of the valve 102 via the first tubing section 112a and (ii) the connector 116 via the second tubing section 112b. The fluid control device 114 is externally operable by a user to regulate the flow of fluid therethrough and, specifically, from the lumen 108 of the catheter 106 to the syringe 120. For example, the fluid control device 114 can be transitioned between (i) a first or closed configuration in which the fluid control device 114 inhibits or even prevents fluid flow therethrough and (ii) a second or open configuration in which fluid can flow through the fluid control device 114.

During a clot removal procedure, at least a portion of the system 100, including at least a portion of the catheter 106, can be inserted through the vasculature of a patient to treat clot material therein. In some embodiments, the system 100 is inserted to a target treatment location proximate to the clot material through an introducer sheath that traverses the skin and tissue of the patient to provide an access site. The fluid control device 114 can be in the closed position during insertion of the catheter 106. After positioning the catheter 106 at the treatment location and with the fluid control device 114 in the closed position, a user/operator can generate a vacuum in the syringe 120 by, for example, fluidly coupling the syringe 120 to the connector 116 and withdrawing a plunger of the syringe 120. In this manner, a vacuum is charged within the syringe 120 (e.g., a negative pressure is maintained) before the syringe 120 is fluidly connected to the lumen 108 of the catheter 106. To aspirate the lumen 108 of the catheter 106, the user can actuate (e.g., open) the fluid control device 114 to fluidly connect the syringe 120 to the catheter 106 and thereby apply or release the vacuum stored in the syringe 120 to the lumen 108 of the catheter 106. Opening of the fluid control device 114 instantaneously or nearly instantaneously applies the stored vacuum pressure to the tubing assembly 110 and the catheter 106, thereby generating a suction pulse throughout the catheter 106 that can aspirate the clot material into the catheter 106. In some embodiments, the vacuum from the syringe 120 is applied with the fluid control device 114 in an open position (e.g., to provide continuous vacuum). That is, the user can generate the vacuum in the syringe 120 while the fluid control device 114 is open (e.g., while the syringe 120 is fluidly connected to the lumen 108 of the catheter 106) to thereby aspirate the clot material while also simultaneously generating the vacuum—that is, for example, without or substantially without storing the vacuum in the syringe 120.

Figure 2A:
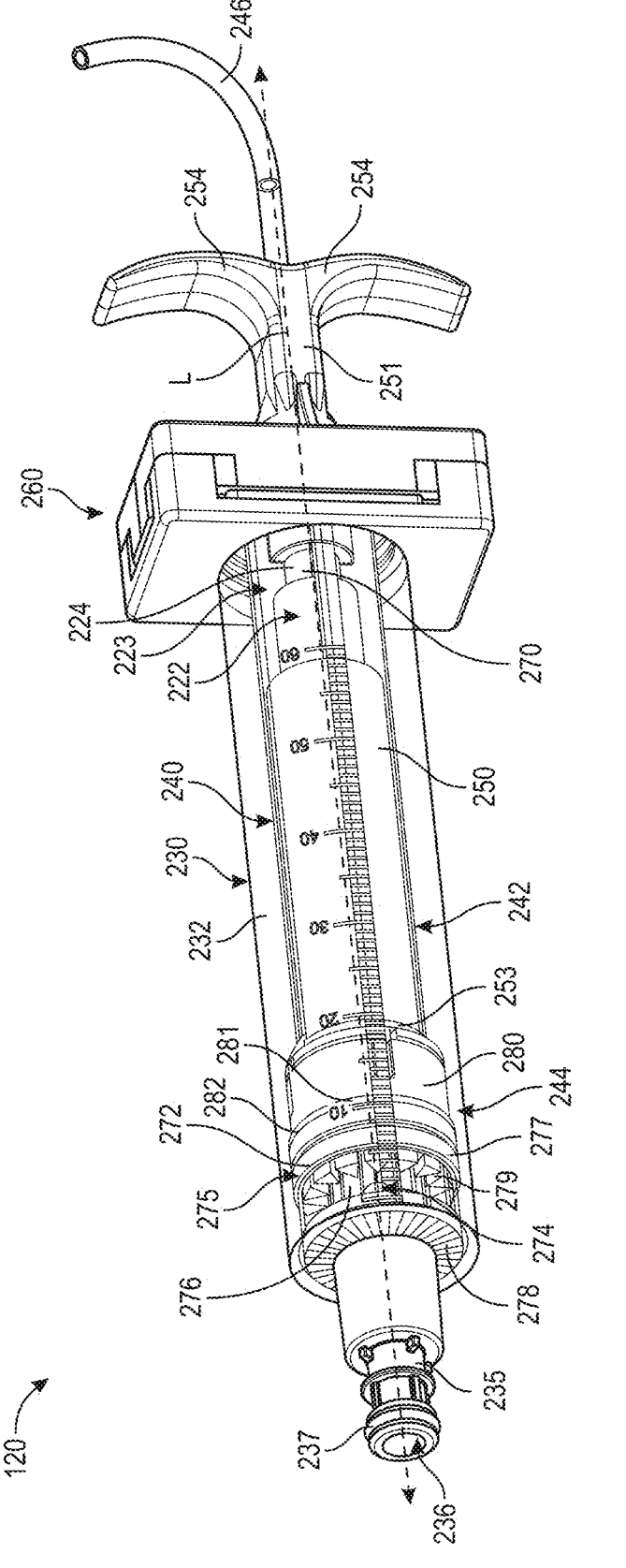
FIGS. 2A and 2B are an isometric view and an exploded view, respectively, of a syringe of the clot treatment system of FIG. 1 in accordance with embodiments of the present technology.
Figure 2B:
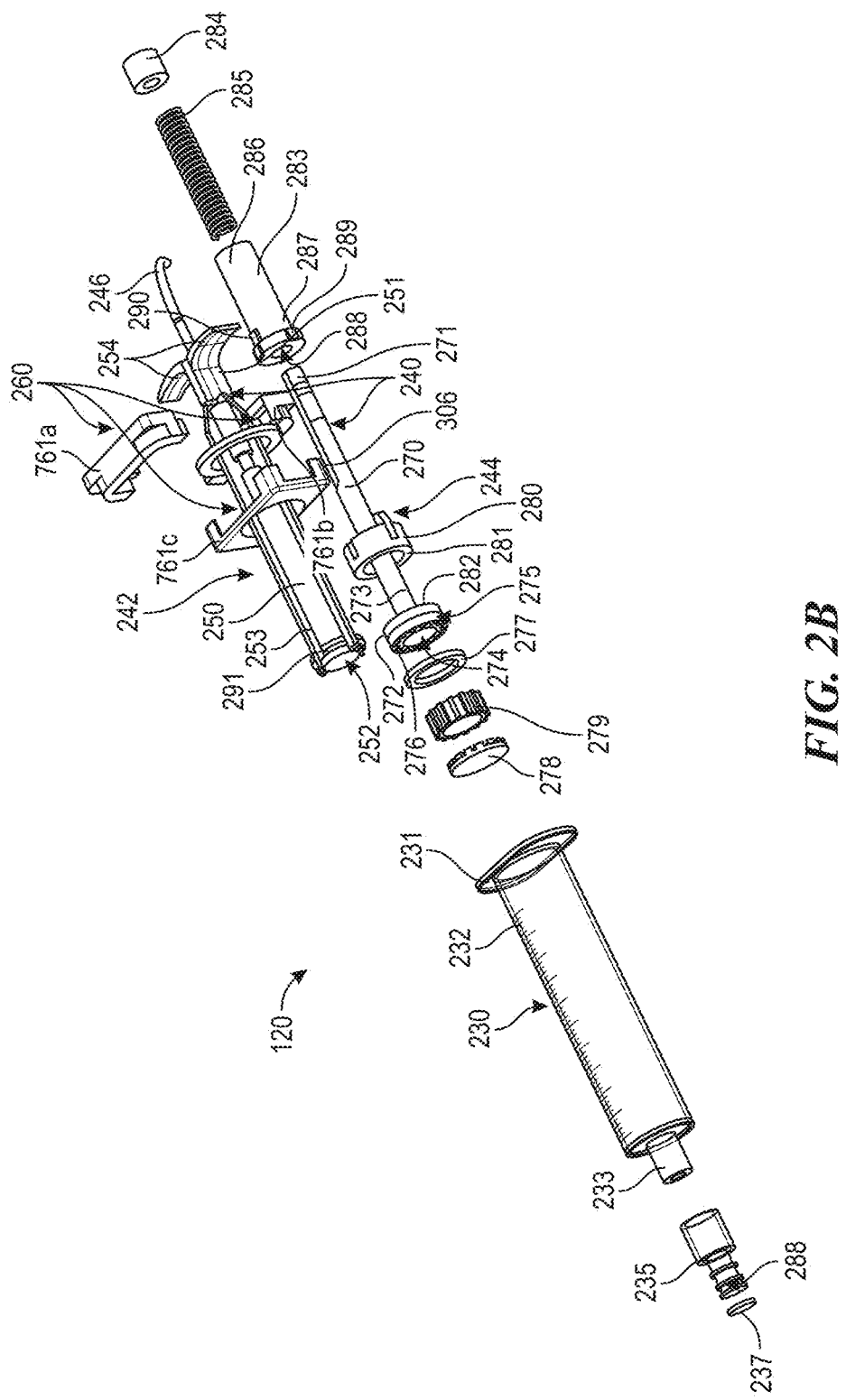

FIGS. 2A and 2B are an isometric view and an exploded view, respectively, of the syringe 120 of FIG. 1 in accordance with embodiments of the present technology. The syringe 120 can be referred to as a pressure source, a vacuum syringe, an automatic-locking syringe, an automatic-unlocking syringe, a filtering syringe, an automatic-locking and automatic-unlocking syringe, an automatic-locking and automatic-unlocking vacuum syringe, a vacuum-locking syringe, a vacuum-unlocking syringe, and/or the like. In some embodiments, the syringe 120 can include some features generally similar in structure and/or function, or identical in structure and/or function, to those of any of the syringes described in U.S. patent application Ser. No. 17/396,426, titled "AUTOMATICALLY-LOCKING VACUUM SYRINGES, AND ASSOCIATED SYSTEMS AND METHODS," and filed Aug. 8, 2021, and/or U.S. patent application Ser. No. 18/192,855, titled "BLOOD-FILTERING DEVICES FOR USE WITH CLOT TREATMENT SYSTEMS," and filed Mar. 30, 2023, each of which is incorporated by reference herein in its entirety.

Referring to FIGS. 2A and 2B, in the illustrated embodiment the syringe 120 includes a plunger assembly 240 slidably positioned within a barrel 230. The barrel 230 is shown as partially transparent in FIG. 2A for clarity. Referring to FIG. 2B, the barrel 230 can include a barrel portion 232 (e.g., a cylindrical portion) extending between a proximal flange 231 (e.g., a proximal end portion) and a distal tip 233 (e.g., a distal end portion). In some embodiments, the barrel portion 232 can have a volume of about 60 cc or greater than 60 cc. The tip 233 is configured to be releasably or permanently coupled to an adaptor 235. Referring to FIGS. 2A and 2B, in some embodiments the adaptor 235 can define a bore 236 having a size (e.g., and corresponding inner diameter) equal to or greater than 16 Fr, 20 Fr, 22 Fr, 24 Fr, 26 Fr, 28 Fr, 30 Fr, 32 Fr, and/or the like. In the illustrated embodiment, the adaptor 235 is a Toomey-tip adaptor having a sealing member 277 (e.g., an O-ring) extending around an exterior surface thereof for sealingly engaging (e.g., connecting to) a Toomey fitting or Toomey adaptor, such as the connector 116 of FIG. 1. In other embodiments, the adaptor 235 can be omitted and the tip 233 (FIG. 2B) of the barrel 230 can be directly coupled to another device or system (not shown), and/or the adaptor 235 can be another type of adaptor such as, for example, a Luer lock, Lock slip, and/or needle.

In the illustrated embodiment, the plunger assembly 240 includes a handle assembly 242 (which can also be referred to as a first assembly, a locking assembly, and/or the like) operably coupled to a seal assembly 244 (which can also be referred a second assembly, a filter assembly, a seal and filter assembly, an unlocking assembly, and/or the like). The syringe 120 further includes a locking assembly 260 coupled to the flange 231 (FIG. 2B) of the barrel 230. The locking assembly 260 is configured to selectively lock the plunger assembly 240 in a withdrawn position under vacuum pressure as described in further detail below with reference to FIGS. 8A and 9.

The handle assembly 242 includes a first shaft 250 (e.g., an elongate member, a tube, a column) extending between a proximal end portion 251 and a distal end portion 253 and defining a lumen 252 (FIG. 2B). The proximal end portion 251 can be configured (e.g., shaped, sized) to be grasped by a user for withdrawing (e.g., retracting, pulling) and/or depressing (e.g., advancing, pushing) the plunger assembly 240 through the barrel 230 during operation of the syringe 120. For example, in the illustrated embodiment the proximal end portion 251 includes a pair of opposing flanges 254 extending radially outward from a longitudinal axis L (FIG. 2A) of the syringe 120 and forming a handle configured to be grasped by a hand of the user.

The seal assembly 244 includes a second shaft 270 (partially obscured in FIG. 2A; e.g., an elongate member, a tube, a column) having a proximal end portion 271 (FIG. 2B) and a distal end portion 273 (FIG. 2B). The distal end portion 273 of the second shaft 270 can be coupled to (e.g., integrally formed, releasably or permanently attached to) a sealing head 272. The second shaft 270 defines a lumen (obscured in FIGS. 2A and 2B) extending therethrough and having a proximal opening at the proximal end portion 271 and a distal opening 274 at the sealing head 272. In the illustrated embodiment, the sealing head 272 has an annular shape including a circumferential groove 275 and a distal face 276. The distal opening 274 is formed through the distal face 276 and can, for example, be generally aligned along the longitudinal axis L (FIG. 2A). An outlet tube 246 can extend partially through the lumen 252 (FIG. 2B) of the first shaft 250 from the proximal end portion 251 of the first shaft 250 and be coupled to the proximal end portion 271 (FIG. 2B) of the second shaft 270 to fluidically couple the lumen of the second shaft 270 to the outlet tube 246 such that a fluid flow path extends through (i) the distal opening 274 in the sealing head 272, (ii) the lumen of the second shaft 270, and (iii) the outlet tube 246.

The circumferential groove 275 in the sealing head 272 can receive a sealing member 277 therein, such as an O-ring. The sealing member 277 is configured to sealingly engage an interior surface of the barrel portion 232—even as the plunger assembly 240 moves through the barrel 230—to, for example, define a sealed volume (e.g., of negative/vacuum pressure) within the barrel 230.

In the illustrated embodiment, the seal assembly 244 further includes a distal cap 278 and a filter 279 positioned between the cap 278 and the sealing head 272 (e.g., the distal face 276 of the sealing head 272). The cap 278 can have an annular shape and be impermeable to blood or other liquid flow. The filter 279 can have a circumferential shape and, in some embodiments, can include a plurality of folds or pleats circumferentially disposed thereabout. The filter 279 and the cap 278 can extend entirely about the distal face 276 of the sealing head 272 to enclose the distal opening 274. The filter 279, the cap 278, and the sealing head 272 can be coupled together (e.g., integrally formed, releasably or permanently attached together) such that these components are configured to move together through the barrel 230.

The filter 279 can be permeable to blood but impermeable to the clot material by, for example, including a plurality of pores sized to allow blood to pass therethrough but to inhibit clot material from passing therethrough. When the syringe 120 is used in a clot removal procedure on a patient, such as described in detail above with reference to FIG. 1, clot material and blood can be aspirated into the barrel 230. To filter the clot material from the blood, the plunger assembly 240 can be depressed through the barrel 230 to drive the sealing head 272 and the sealing member 277 distally through the barrel 230 to thereby increase the pressure in the barrel 230. The increased pressure can drive the blood (i) radially through the filter 279, (ii) proximally through the distal opening 274 in the scaling head 272, (iii) proximally through the lumen of the second shaft 270, and (iv) proximally through the outlet tube 246. Alternatively or additionally, a source of negative pressure (e.g., another syringe) can be coupled to the outlet tube 246 and activated to generate negative pressure that acts to draw the blood (i) radially through the filter 279, (ii) proximally through the distal opening 274 in the scaling head 272, (iii) proximally through the lumen of the second shaft 270, and (iv) proximally through the outlet tube 246. The filtered blood can be collected in a reservoir, container, aspiration source, etc., for reintroduction into the patient to minimize blood loss during the clot removal procedure. In some embodiments, such filtration components of the syringe 120 can include some features generally similar in structure and/or function, or identical in structure and/or function, to those of any of the syringes described in U.S. patent application Ser. No. 18/192,855, titled "BLOOD-FILTERING DEVICES FOR USE WITH CLOT TREATMENT SYSTEMS," and filed Mar. 30, 2023, which is incorporated by reference herein in its entirety.

In other embodiments, the filter 279, the cap 278, the lumen in the second shaft 270, and/or the outlet tube 246 can be omitted. That is, the syringe 120 can be a non-filtering syringe. For example, FIGS. 11A-14 described in detail below illustrate a non-filtering syringe in accordance with embodiments of the present technology. In such embodiments, the seal assembly 244 can comprise only the second shaft 270 (e.g., without a lumen therethrough), the sealing head 272 (e.g., without a distal opening therethrough), and the sealing member 277.

In the illustrated embodiment, the seal assembly 244 further includes an unlocking member 280 coupled to the sealing head 272. More specifically, the unlocking member 280 (which can also be referred to as a shield member, an unlocking and shield member, and/or the like) can include a distal face or end portion 281 coupled to (e.g., attached to, fixed to, integrally formed with) a proximal face or end portion of 282 of the sealing head 272. Referring to FIG. 2B, the handle assembly 242 can further include an elongate annular insert member 283 configured to be coupled to the distal end portion 253 of the first shaft 250 and to extend at least partially through the lumen 252 of the first shaft 250. The seal assembly 244 can further include an annular mount member 284 slidably positioned within the lumen 252 of the first shaft 250 and coupled to second shaft 270. A biasing member 285, such as a compression spring, can be coupled between the insert member 283 and the mount to member 284 to operatively couple the seal assembly 244 to the handle assembly 242. As described in greater detail below, the insert member 283 constrains travel (e.g., distal movement) of the mount member 284. Accordingly, in some embodiments the insert member 283 need not extend through the lumen 252 of the first shaft 250 (e.g., where the biasing member 285 is configured to compress and bottom out to constrain travel of the mount member 284).

Figure 3:
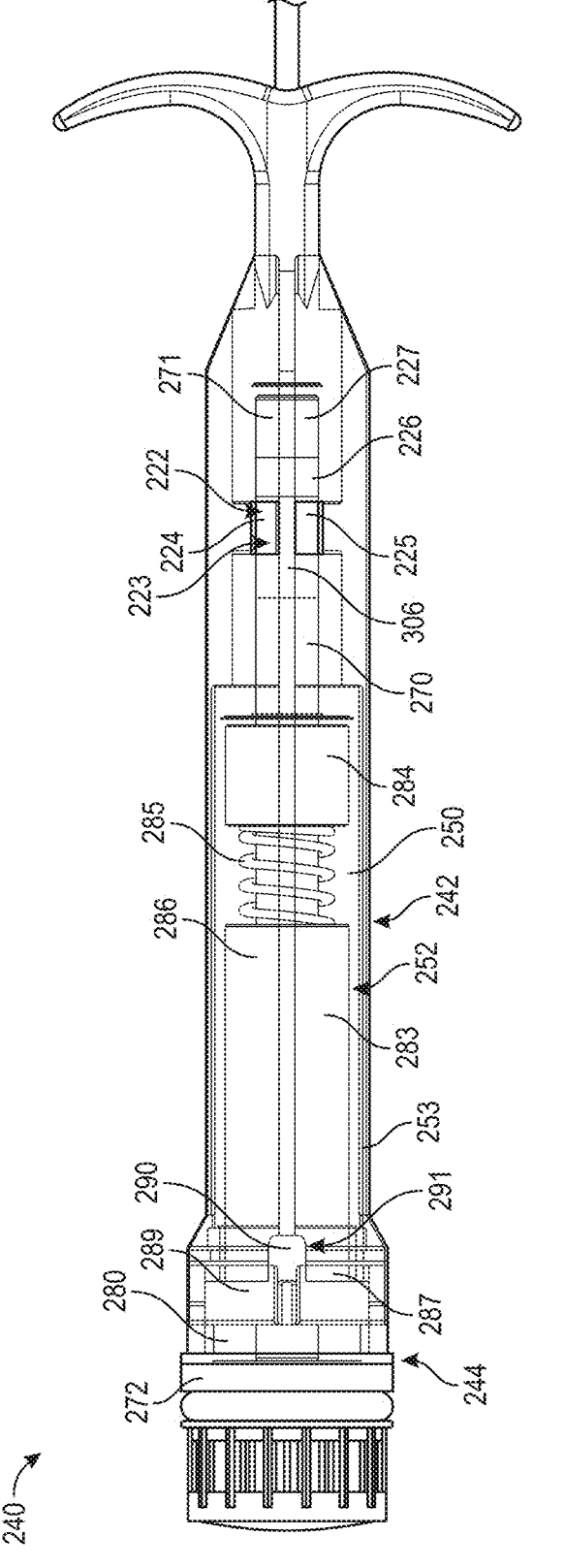
FIG. 3 is a partially-transparent side view of a plunger assembly of the syringe of FIGS. 2A and 2B in accordance with embodiments of the present technology.

FIG. 3 is a partially-transparent side view of the plunger assembly 240 in accordance with embodiments of the present technology. The first shaft 250 of the handle assembly 242 and the unlocking member 280 of the seal assembly 244 are shown as partially transparent in FIG. 3 for clarity. Referring to FIGS. 2B and 3, the insert member 283 can have a proximal end portion 286, a distal end portion 287, a lumen 288 (FIG. 2B) extending between the proximal end portion 286 and the distal end portion 287, and a flange 289 extending circumferentially about the distal end portion 287. The flange 289 can be coupled (e.g., fixedly coupled) to the distal end portion 253 of the first shaft 250 via one or more tabs 290 that engage corresponding recesses or detents 291 at the distal end portion 253 of the first shaft 250. In some embodiments, the flange 289 includes two of the tabs 290 on opposing circumferential portions of the flange 289 (e.g., spaced apart by about 180 degrees) that engage with a corresponding pair of the detents 291 while, in other embodiments, the flange 289 includes more or fewer of the tabs 290 and/or the insert member 283 can be coupled to the first shaft 250 in different manners (e.g., via fasteners, via adhesive, integrally formed).

Referring to FIG. 3, the insert member 283 extends at least partially through the lumen 252 of the first shaft 250. The second shaft 270 of the seal assembly 244 extends from the scaling head 272 through the annular unlocking member 280, through the lumen 288 (FIG. 2B) of the insert member 283, through the annular mount member 284, and terminates at the proximal end portion 271 within the lumen 252 of the first shaft 250 proximal to the mount member 284. The mount member 284 is positioned proximal to the proximal end portion 286 of the insert member 283 within the lumen 252 of the first shaft 250 and is slidably positioned within the lumen 252. The mount member 284 can be coupled (e.g., fixedly coupled) to the second shaft 270 within the lumen 252 such that these components are configured to move together. In some embodiments, the mount member 284 includes one or more protrusions (obscured in FIG. 3) on an inner surface thereof that engage a corresponding one or more detents or tracks 306 (also shown in FIG. 2B) formed in the second shaft 270 to couple the mount member 284 to the second shaft 270. The biasing member 285 extends over (e.g., is coiled over) the second shaft 270 within the lumen 252 of the first shaft 250 and has a proximal end portion (obscured in FIG. 3) fixed to the mount member 284 and a distal end portion (obscured in FIG. 3) fixed to the insert member 283. In some embodiments, the biasing member 285 extends at least partially through the lumen 288 (FIG. 2B) of the insert member 283 and is fixed therein.

Figure 4A:
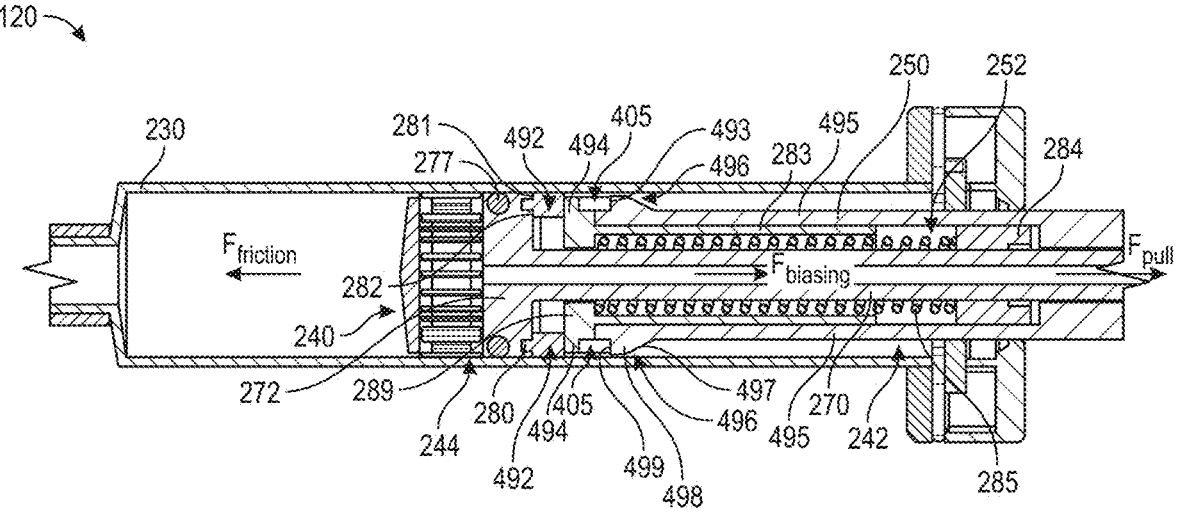
FIGS. 4A and 5A are cross-sectional side views of the syringe of FIGS. 2A and 2B in a first position and a second position, respectively, in accordance with embodiments of the present technology.
Figure 4B:
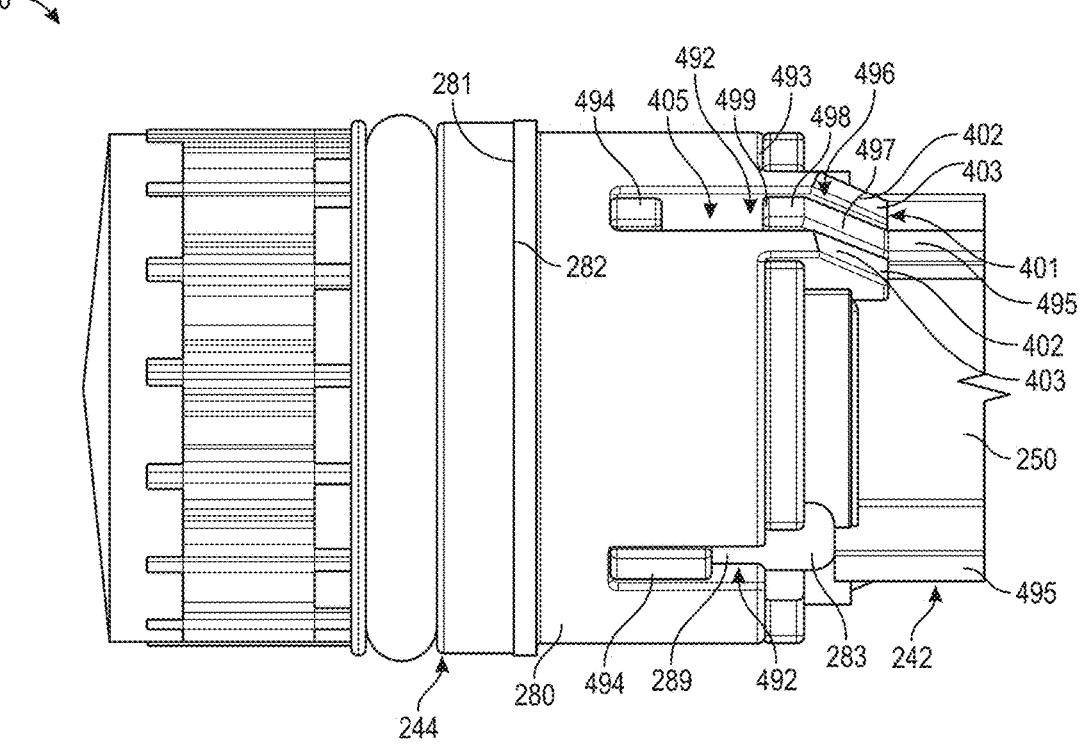
FIGS. 4B and 5B are enlarged side views of a distal portion of the plunger assembly of the syringe of FIGS. 2A and 2B in the first position and the second position, respectively, in accordance with embodiments of the present technology.
Figure 5A:
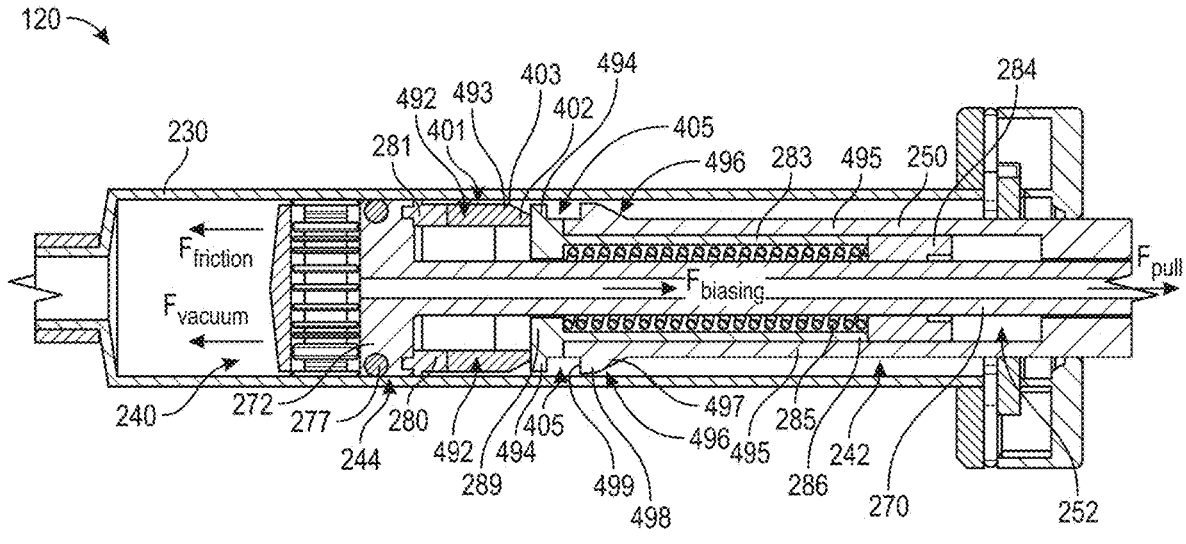
Figure 5B:
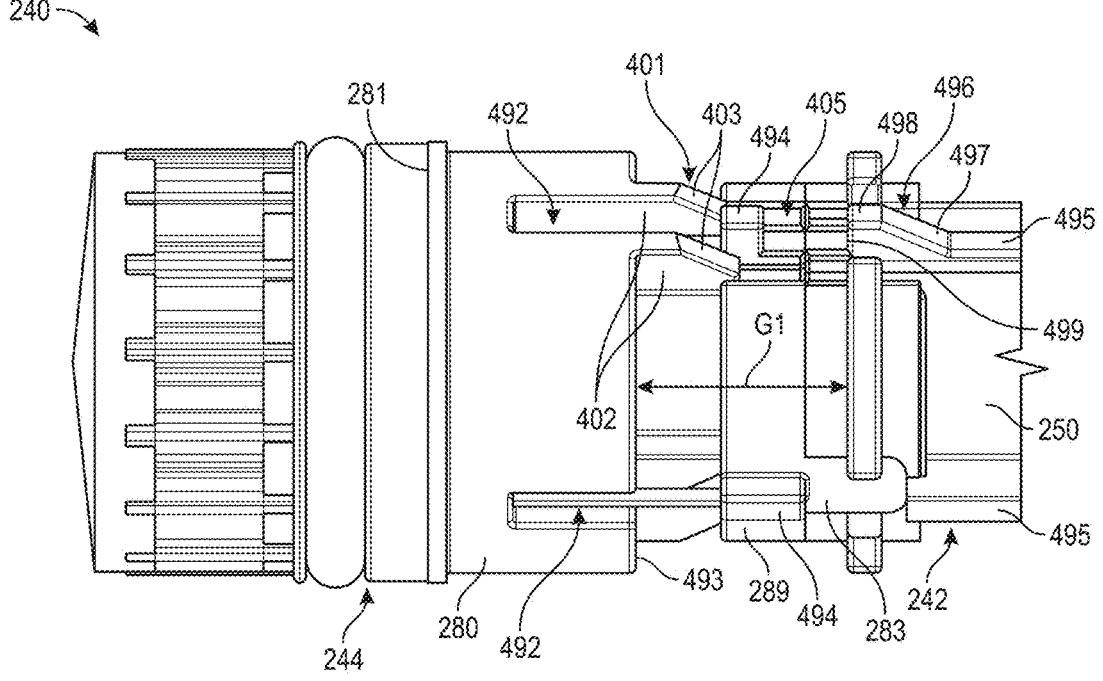

FIGS. 4A and 5A are cross-sectional side views of the syringe 120 in a first position (which can also be referred to as a shielded position, a non-vacuum position, and/or the like; as shown in FIGS. 2A and 3) and a second position (which can also be referred to as a locking position, a vacuum position, and/or the like), respectively, in accordance with embodiments of the present technology. FIGS. 4B and 5B are corresponding enlarged side views of a distal portion of the plunger assembly 240 in the first position and the second position, respectively, in accordance with embodiments of the present technology.

Referring to FIGS. 4A-5B together, the unlocking member 280 of the seal assembly 244 can include one or more grooves or channels 492 formed therein and extending distally from a proximal face or end portion 493 of the unlocking member 280 at least partially toward the distal end portion 281 thereof parallel to the longitudinal axis L (FIG. 2A). In the illustrated embodiment, the insert member 283 includes one or more projections or tabs 494 extending radially outward from the flange 289. The tabs 494 can be aligned with corresponding ones of the channels 492 and can slidingly move through the channels 492 between the first position (FIGS. 4A and 4B) and the second position (FIGS. 5A and 5B).

In the illustrated embodiment, the first shaft 250 includes one or more rails 495 extending along an exterior surface thereof and aligned with corresponding ones of the channels 492 and tabs 494. One or more of the rails 495 can include a lock feature 496 at a distal end portion thereof. In the illustrated embodiment, the lock features 496 include (i) a ramp portion 497, (ii) a plateau portion 498 extending from the ramp portion 497, and (iii) a stop surface 499 extending from the plateau portion 498. The ramp portion 497 can extend/slope at angle relative to the longitudinal axis L (FIG. 2A) in a direction (i) away from the longitudinal axis L and (ii) distally toward the unlocking member 280. The plateau portion 498 can extend away from the ramp portion 497 in a direction toward the unlocking member 280 and generally parallel to the longitudinal axis L. The stop surface 499 can extend away from the plateau portion 498 in a direction generally perpendicular to the plateau portion 498 and the longitudinal axis L. The stop surface 499 of the lock features 496 and a corresponding one of the tabs 494 can together define a locking recess 405. In some embodiments, the tabs 494 can be omitted such that the locking recesses 405 are defined distal of the stop surfaces 499 of the lock features 496. In some embodiments, the lock features 496 can compromise a tab, flat face, half disc, and/or other feature extending from the exterior surface of the first shaft 250.

The unlocking member 280 can further include one or more unlock features 401 (obscured in FIG. 4A) aligned with corresponding ones of the lock features 496. In the illustrated embodiment, the unlock features 401 include a pair of spaced apart rails or projections 402 extending from the proximal end portion 493 of the unlocking member 280 and each having a ramp portion 403 that can extend/slope at angle relative to the longitudinal axis L (FIG. 2) in a similar or identical manner to the ramp portion 497 of the lock features 496. The projections 402 extend the channel 492 of the unlocking member 280. In other embodiments, the lock features 496 and/or the unlock features 401 can have different arrangements/configurations. For example, the lock features 496 can comprise a pair of spaced apart rails or projections that extend from the unlocking member 280, and the unlock features 401 can include a ramp portion, a plateau portion, and a stop surface. In the first position shown in FIGS. 4A and 4B, the tabs 494 and the locking features 496 of the handle assembly 242 are positioned within corresponding ones of the channels 492 formed in/by the unlocking member 280 and the unlock features 401 such that the locking recesses 405 are covered (e.g., radially shielded) by the unlocking member 280. In the second position shown in FIGS. 5A and 5B, the tabs 494 and the lock features 496 of the handle assembly 242 are translated outside of the channels 492 such that the locking recesses 405 are uncovered (e.g., radially unshielded) by the unlocking member 280 and accessible.

In some embodiments, the unlocking member 280 only includes one of the channels 492 and one of the unlock features 401, and the handle assembly 242 only includes one of the rails 495, one of the lock features 496, and one of the tabs 494 (collectively a "locking and unlocking mechanism")—each aligned with one another. In some embodiments, the plunger assembly 240 can include multiple ones of the locking and unlocking mechanisms—such as a pair of the locking and unlocking mechanisms on opposing circumferential portions of the plunger assembly 240 (e.g., spaced apart by about 180 degrees) as shown in FIGS. 4A, 5A, and 5B. In some embodiments, the plunger assembly 240 can include one or more of the channels 492, tabs 494, and rails 495 in an aligned configuration without a corresponding lock feature 496 or unlock feature 401.

Referring to FIG. 4A, the biasing member 285 can be configured (e.g., shaped, sized, formed) to allow the plunger assembly 240 to move between the first position (FIG. 4A) and the second position (FIG. 5A) based on (e.g., in response to) an amount of vacuum pressure within the barrel 230. This operation of the plunger assembly 240 is best understood in view of the various forces acting on the plunger assembly 240 as the plunger assembly 240 is withdrawn through the barrel 230. For example, retraction of the handle assembly 242 generates (i) a pull force $F_{pull}$ in the proximal direction and (ii) a friction force $F_{friction}$ in the opposite, distal direction, via the engagement of the scaling member 277 with the barrel 230. To retract the plunger assembly 240, the user must overcome the resistance of the sealing member 277 on the barrel 230 (i.e., $F_{pull} > F_{friction}$). Although $F_{friction}$ can act in both directions to resist movement of the plunger assembly 240 or keep the plunger assembly 240 fixed when not acted upon, this illustration will strictly define it as the force that opposes the user's pull force $F_{pull}$.

Referring to FIG. 5A, when vacuum is generated within the barrel 230 (e.g., when the syringe 120 is coupled to the connector 116 of FIG. 1 and the plunger assembly 240 is retracted with the fluid control device 114 of FIG. 1 in the closed position), an additional vacuum force F vacuum acts on the plunger assembly 240 (e.g., the sealing member 277) in the distal direction. To retract the plunger assembly 240 under vacuum, the user must overcome both the resistance of the scaling member 277 on the barrel 230 as well as the opposing vacuum force (i.e., $F_{pull} > F_{friction} + F_{vacuum}$). The vacuum force $F_{vacuum}$ depends on both the amount of negative pressure generated as well as the cross-sectional area of the plunger assembly 240 subject to the negative pressure (Pressure=Force/Area). When pressure decreases (e.g., negative pressure increases in magnitude) as the plunger assembly 240 is retracted, $F_{vacuum}$ also increases, presenting a larger contribution at the end of the withdrawal stroke. Conversely, as negative pressure approaches its minimum theoretical value (e.g., maximum magnitude), $F_{vacuum}$ plateaus before reaching the end of the withdrawal stroke.

Referring to FIGS. 4A and 5A, the biasing member 285 contributes a biasing force $F_{biasing}$ that acts in the proximal direction against the seal assembly 244 via the coupling of the biasing member 285 against the mount member 284, which is in turn coupled to the second shaft 270. That is, the biasing member 285 biases the mount member 284 proximally through the lumen 252 of the first shaft 250 to urge the second shaft 270 and the sealing head 272 proximally through the barrel 230.

Referring to FIG. 4A, the biasing member 285 can be configured such that the biasing force $F_{biasing}$ is greater than the friction force $F_{friction}$ (i.e., $F_{biasing} > F_{friction}$). For example, the biasing member 285 can be a compression spring selected to have a spring force (e.g., spring constant) that is greater than the friction force $F_{friction}$. Accordingly, in the first position shown in FIGS. 4A and 4B in the absence of the vacuum force $F_{vacuum}$ (FIG. 5A), the biasing member 285 is generally rigid and drives/biases the mount member 284 and coupled seal assembly 244 proximally through the barrel 230 such that the locking recesses 405 are positioned with the channels 492 (e.g., as best seen in FIG. 4B). In this first position, the flange 289 of the handle assembly 242 can abut the proximal end portion 493 of the unlocking member 280 and/or the tabs 494 can abut distal end portions of corresponding ones of the channels 492. Accordingly, during retraction of the plunger assembly 240, the plunger assembly 240 acts as an integral plunger in which the handle assembly 242 and the seal assembly 244 move in tandem through the barrel 230 as the biasing member 285 provides a rigid coupling therebetween.

Referring to FIG. 5A, the biasing member 285 can be configured such that the biasing force $F_{biasing}$ is greater than the friction force $F_{friction}$ but less than the combined friction force $F_{friction}$ and vacuum force $F_{vacuum}$ (i.e., $F_{vacuum}+F_{friction}>F_{biasing}>F_{friction}$). For example, the biasing member 285 can be a compression spring selected to have a spring force (e.g., spring constant) that is greater than the friction force $F_{friction}$ but less than the combined friction force $F_{friction}$ and vacuum force $F_{vacuum}$. Accordingly, in the second position shown in FIGS. 5A and 5B, the combined friction force $F_{friction}$ and vacuum force $F_{vacuum}$ can overcome the biasing force $F_{biasing}$ of the biasing member 285—causing the biasing member 285 to compress and urge the mount member 284 and coupled seal assembly 244 distally through the barrel 230 such that the locking recesses 405 are spaced apart from and positioned at least partially outside of the channels 492 (e.g., as best seen in FIG. 5B). In this second position, the stop surfaces 499 of the locking features 496 can be spaced apart from the proximal end portion 493 of the unlocking member 280 by a gap $G_1$ (FIG. 5B).

In some embodiments, after the mount member 284 is drawn distally by the vacuum force $F_{vacuum}$ by a predefined distance (e.g., by a distance equal to the gap $G_1$ shown in FIG. 5B), the mount member 284 can contact/abut/engage the proximal end portion 286 of the insert member 283 within the lumen 252 of the first shaft 250. This engagement can inhibit or even prevent the mount member 284 and the coupled seal assembly 244 from being drawn farther distally through the barrel 230 by the vacuum force $F_{vacuum}$. Accordingly, after the plunger assembly 240 reaches the second position shown in FIGS. 5A and 5B, the plunger assembly 240 again acts as an integral plunger in which the handle assembly 242 and the seal assembly 244 move in tandem through the barrel 230 as the insert member 283 rigidly engages the mount member 284. In other embodiments, the mount member 284 need not engage the insert member 283 to fix the plunger assembly 240 in the second position and inhibit further separation between the seal assembly 244 and the handle assembly 242. For example, the biasing member 285 can be configured to fully compress (e.g., bottom out) to inhibit further movement of the seal assembly 244 relative to the handle assembly 242 after a predefined separation between the seal assembly 244 and the handle assembly 242.

Referring to FIGS. 4A and 5A, in some aspects of the present technology the plunger assembly 240 is configured to move between the first and second positions based on the presence of the vacuum force $F_{vacuum}$. That is, the plunger assembly 240 is vacuum-sensitive. In some embodiments the vacuum force $F_{vacuum}$ is significantly greater than the friction force $F_{friction}$ (e.g., 5 times greater, 10 times greater, 100 times greater, or more; i.e., $F_{vacuum}>>F_{friction}$). For example, the distal face of the seal assembly 244 can have a relatively large surface area and/or the barrel 230 can have a relatively large volume such that the magnitude of the resultant negative pressure is high. The friction force $F_{friction}$ on the sealing member 277 can be less predictable than the vacuum force $F_{vacuum}$ and can differ as a result of a quantity of silicone applied to the sealing member 277, an amount of compression of the sealing member 277, and/or a length of time since the sealing member 277 was moved. Accordingly, if the vacuum force $F_{vacuum}$ were not much larger than the friction force $F_{friction}$, it may be difficult to select the biasing member 285 to react to only one force and not the other. Therefore, in some embodiments of the present technology the syringe 120 is configured such that the vacuum force $F_{vacuum}$ is significantly greater than the friction force $F_{friction}$ to make the response of the biasing member 285 more predictable.

Although (i) a discrete first position is shown in FIGS. 4A and 4B in which the seal assembly 244 and the handle assembly 242 are positioned closest to one another (e.g., with the flange 289 of the handle assembly 242 butting the proximal end portion 493 of the unlocking member 280 and/or the tabs 494 abutting distal end portions of corresponding ones of the channels 492) and (ii) a discrete second position is shown in FIGS. 5A and 5B (e.g., with the stop surfaces 499 of the locking features 496 spaced apart from the proximal end portion 493 of the unlocking member 280 by the gap $G_1$ (FIG. 5B) and the mount member 284 contacting the proximal end portion 286 of the insert member 283), the plunger assembly 240 can have any intermediate position between the first position and the second position depending on, for example, a magnitude of the vacuum force $F_{vacuum}$. That is, as the vacuum force $F_{vacuum}$ increases (e.g., as the plunger assembly 240 is withdrawn farther proximally through the barrel 230) the vacuum force $F_{vacuum}$ can progressively compress the biasing member 285 to drive the plunger assembly 240 along a continuous spectrum of positions between the first position and the second position. Contrariwise, as the vacuum force $F_{vacuum}$ decreases (e.g., as the plunger assembly 240 is depressed farther distally through the barrel 230 and/or when the fluid control device 114 of FIG. 1 is opened after generating negative pressure in the barrel 230) the energy stored in the biasing member 285 can progressively extend the biasing member 285 to drive the plunger assembly 240 back along the continuous spectrum of positions between the second position and the first position.

Figure 6:
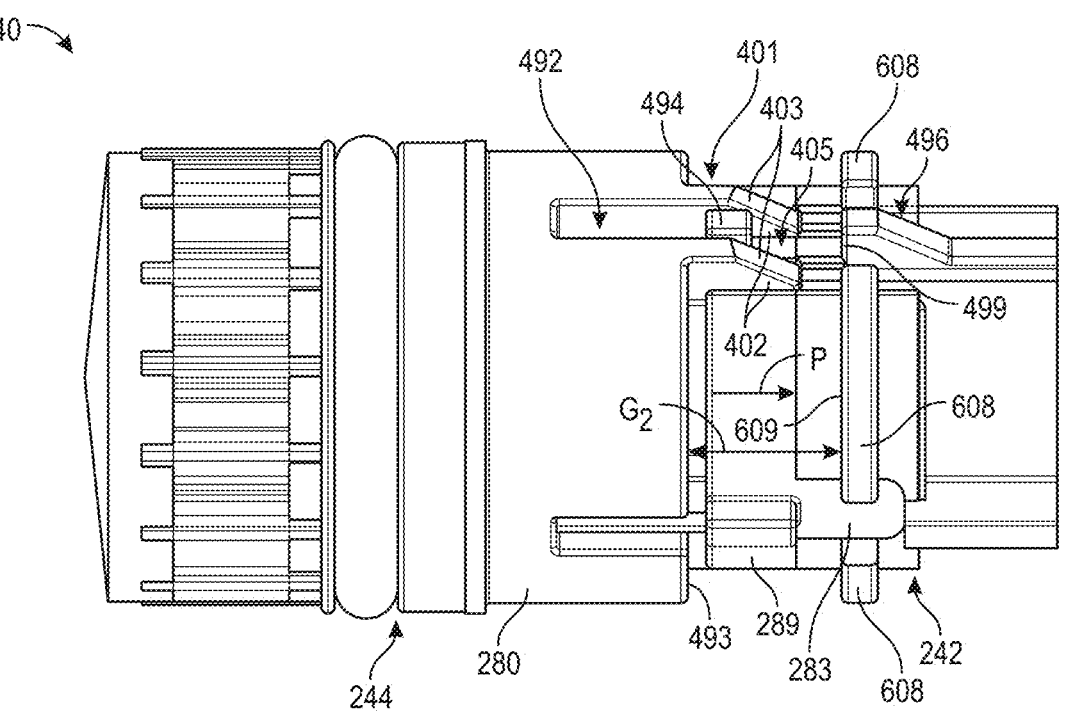
FIG. 6 is a side view of the distal portion of the plunger assembly shown in FIGS. 4B and 5B in an intermediate position between the first position and the second position in accordance with embodiments of the present technology.

FIG. 6, for example, is an enlarged side view of the distal portion of the plunger assembly 240 shown in FIGS. 4B and 5B in an intermediate position between the first position and the second position in accordance with embodiments of the present technology. In the illustrated embodiment, the stop surfaces 499 of the locking features 496 are spaced apart from the proximal end portion 493 of the unlocking member 280 by a gap $G_2$ smaller than the gap $G_1$ (FIG. 5B) in the second position. Similarly, the locking recesses 405 and the lock features 496 are at least partially exposed from and uncovered (e.g., not radially shielded) by the channels 492 in the unlocking member 280. As further shown in FIG. 6, the insert member 283 can include a flange 609 extending at least partially circumferentially thereabout and defining a distal surface 609. The distal surface 609 can be longitudinally aligned with the stop surfaces 499 of the lock features 496. Accordingly, the gap $G_2$ can be defined between the flange 609 and the proximal end portion 493 of the unlocking member 280.

Figure 7:
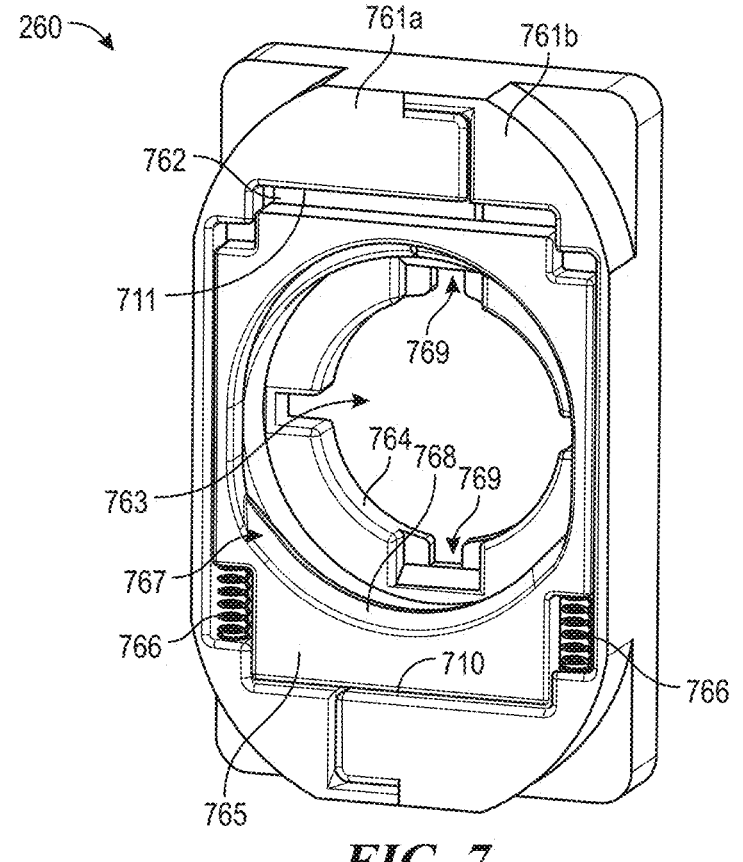
FIG. 7 is an isometric view of a locking assembly of the syringe of FIGS. 2A and 2B in accordance with embodiments of the present technology.

FIG. 7 is an isometric view of the locking assembly 260 of the syringe 120 of FIGS. 2A and 2B in accordance with embodiments of the present technology. In the illustrated embodiment, the locking assembly 260 includes a housing 761 (including an individually identified first housing portion 761a and a second housing portion 761b) defining a recess 762 and having a housing opening 763 extending axially therethrough and defined by an edge portion 764. In some embodiments, the housing 761 comprises multiple portions that can be interlocked or otherwise coupled together, such as the first housing portion 761a, the second housing portion 762b, and a third housing portion 762c (omitted in FIG. 7 for clarity; shown in FIG. 2B). Referring to FIGS. 2B and 7, the housing 761 can be assembled by interlocking or otherwise coupling the first housing portion 761a and the second housing portion 761b to define the recess 762 and the housing opening 763, positioning the flange 231 of the barrel 230 against the first and second housing portions 761a-b, and then coupling the third housing portion 761c over the flange 231 and to the first and second housing portions 761a-b. In other embodiments, the housing 761 can have a different shape, can be coupled to the barrel 230 in different manners, can comprise a different number of discrete portions, and/or can be integrally formed.

Referring to FIG. 7, the locking assembly 260 further includes a lock member or lock plate 765 coupled to the housing 761 within the recess 762 via one or more biasing members 766 (e.g., a pair of the biasing members 766). The lock plate 765 can include a lock plate opening 767 extending axially therethrough and defined by an edge including a lock rail 768 (which can also be referred to as a locking edge, a locking edge portion, a plunger engagement portion, and/or the like). Referring to FIGS. 2A, 4A-5B, and 7, the locking assembly 260 can receive the plunger assembly 240 through the housing opening 763 and the lock plate opening 767. In some embodiments, the edge portion 764 of the lock plate 765 defining the housing opening 764 can include one or more channels 769 (e.g., cutouts, grooves) configured (e.g., shaped, sized, positioned) to slidingly receive one or more of the rails 495 of the first shaft 250 of the plunger assembly 240 therethrough to, for example, facilitate and maintain alignment of the plunger assembly 240, more specifically the lock feature 496 and the unlock feature 401, relative to the locking assembly 260.

Referring to FIG. 7, the recess 762 can have a first end portion 710 and a second end portion 711 opposite the first end portion 710. The biasing members 766 can extend between and operably couple the lock plate 765 to the housing 761 proximate the first end portion 710 of the recess 762. The biasing members 766 can comprise, for example, compression springs that bias the lock plate 765 away from the first end portion 710 of the recess 762 toward the second end portion 711 of the recess 762. The locking assembly 260 is shown in a first position (e.g., a compressed position) in FIG. 7 in which the lock plate 765 is urged against the force of the biasing members 766 toward the first end portion 710 of the recess 762. In some embodiments, in the first position, the lock plate 765 can (i) abut the housing 761 at the first end portion 710 of the recess 762 and (ii) be spaced apart from the housing 761 at the second end portion 711 of the recess 762. Absent a force against the lock plate 765, the biasing members 766 can drive the lock plate 765 through the recess 762 to a second position (e.g., an extended position, a relaxed position) in which the lock plate 765 is urged toward the second end portion 711 of the recess 762. That is, the lock plate 765 can be normally biased to the second position. In some embodiments, in the second position, the lock plate 765 can (i) abut the housing 761 at the second end portion 711 of the recess 762 and (ii) be spaced apart from the housing 761 at the first end portion 710 of the recess 762.

Figures 8A, 8B:
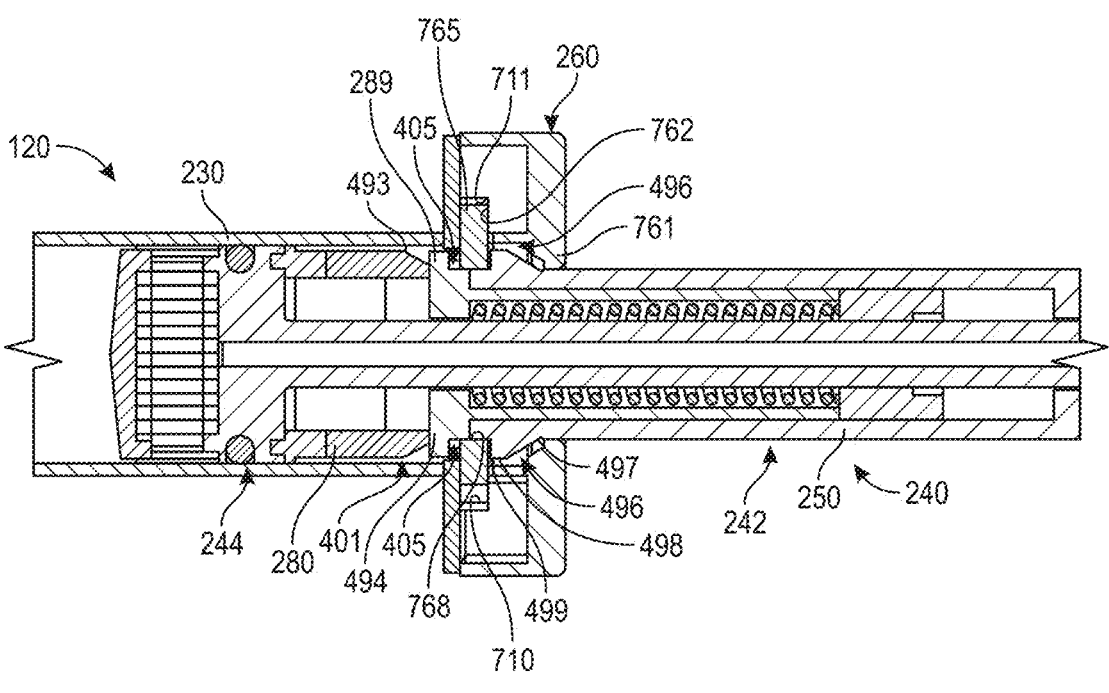
FIGS. 8A and 8B are enlarged cross-sectional side views of the syringe of FIGS. 2A and 2B with the plunger assembly in a withdrawn position and locked to the locking assembly and unlocked from the locking assembly, respectively, in accordance with embodiments of the present technology.

FIGS. 8A and 8B are enlarged cross-sectional side views of the syringe 120 with the plunger assembly 240 proximally withdrawn through the barrel 230 to a withdrawn position and locked to the locking assembly 260 and unlocked from the locking assembly 260, respectively, in accordance with embodiments of the present technology. Referring to FIG. 8A, the plunger assembly 240 is in the first position described in detail with reference to FIGS. 5A and 5B in which the vacuum force $F_{vacuum}$ actuates the plunger assembly 240 such that (i) the flange 289 of the handle assembly 242 is spaced apart from the proximal end portion 493 of the unlocking member 280 by the gap $G_1$ (FIG. 5B) and (ii) the locking recesses 405 are spaced apart from and uncovered (e.g., not radially shielded) by the unlocking member 280. As the plunger assembly 240 is withdrawn proximally through the barrel 230 with the plunger assembly 240 in the first position, the lock feature 496 is spaced apart from and exposed from the unlocking member 280 (e.g., spaced apart from the unlock feature 401).

During withdrawal of the plunger assembly 240, the lock feature 496 is configured to engage the lock rail 768 of the lock plate 765 of the locking assembly 260 to move the lock plate 765 from the normally-biased second position toward the first position. More specifically, the sloped ramp portion 497 of the lock feature 496 can engage the lock rail 768 and drive the lock rail 768 and lock plate 765 toward the first end portion 710 of the recess 762 in the housing 761 until the lock plate 765 reaches the plateau portion 498 of the lock feature 496. That is, the ramp portion 497 of the lock feature 496 translates the longitudinal force of the handle assembly 242 during withdrawal into radial movement of the lock plate 765. Continued withdrawal of the plunger assembly 240 slides the lock rail 768 of the lock plate 765 over/against the plateau portion 498 until the lock rail 768 reaches the stop surface 499. When the lock rail 768 passes the end of the plateau portion 498, the biasing members 766 (FIG. 7) can drive the lock plate 765 toward the second end portion 711 of the recess 762 (e.g., from the compressed first position toward the second position). At this stage, as shown in FIG. 8A, the lock rail 768 of the lock plate 765 is positioned within the locking recess 405 formed by the tab 494 and the lock feature 496 such that plunger assembly 240 is locked in position along the longitudinal axis L (FIG. 2A) relative to the locking assembly 260 (e.g., inhibited from moving/advancing past the lock plate 765 toward the depressed position shown in FIG. 2A). In some embodiments, the lock rail 768 can be positioned distal of the distal surface 609 of the flange 608 (obscured in FIGS. 8A and 8B; FIG. 6). Accordingly, the distal surface 609 of the flange 608 and/or the stop surface 499 of the lock feature 496 can abut the lock rail 768 to inhibit or even prevent distal movement of the plunger assembly 240. In some embodiments, the tab 494 can be omitted as the lock plate 765 inhibits distal movement of the plunger assembly 240 and the housing 761 controls (e.g., inhibits or even prevents) further proximal movement of the plunger assembly 240.

The plunger assembly 240 can remain locked to the locking assembly 260 so long as the vacuum force $F_{vacuum}$ remains and maintains the plunger assembly 240 in the first position shown in FIG. 8A. When the vacuum is released or the vacuum force $F_{vacuum}$ falls below the biasing force $F_{biasing}$, the seal assembly 244 of the plunger assembly 240 can automatically move from the first position shown in FIG. 8A to the second position shown in FIG. 8B to unlock the plunger assembly 240 from the locking assembly 260. More specifically, when the vacuum force $F_{vacuum}$ approaches zero, the biasing force $F_{biasing}$ of the biasing member 285 can drive the mount member 284 proximally through the first shaft 250 to pull the unlocking member 280 proximally toward the locking recess 405 of the handle assembly 242. As best seen in FIG. 6, as the unlocking member 280 moves proximally in the direction of arrow P, the unlock feature 401 can slide past the locking recess 405 as the tab 494 and the lock feature 496 slide through and into the channel 492. Referring to FIGS. 6 and 8B, similar to the operation of the ramp portion 497 of the lock feature 496, the proximal movement of the unlocking member 280 drives the ramp portions 403 (FIG. 6) of the projections 402 (FIG. 6) of the unlocking member 280 against the lock rail 768 of the lock plate 765 to move the lock plate 765 from the normally-biased second position toward the first position. More specifically, the sloped ramp portions 403 of the unlock feature 401 engage the lock rail 768 and drive the lock rail 768 and lock plate 765 toward the first end portion 710 of the recess 762 in the housing 761 and out of the locking recess 405. When the lock plate 765 is removed from the locking recess 405 as shown in FIG. 8B, the plunger assembly 240 is unlocked from the locking assembly 260 and can be moved (e.g., depressed through the barrel 230). In some embodiments, the locking assembly 260 can include a button or other feature that is actuatable to manually remove the lock rail 768 from the locking recess 405 even when there is little or no vacuum within the barrel 230, as described in greater detail below with reference to FIG. 10.

Referring to FIGS. 8A and 8B, only one of the locking recesses 405 and one of the lock features 496 at a lower side of the syringe 120 is configured to engage the lock plate 765. Accordingly, the syringe 120 can include only one of the locking recesses 405 and one of the lock features 496 positioned to engage the lock plate 765. In the illustrated embodiment, the one of the locking recesses 405 and the one of the lock features 496 at the upper side of the syringe 120 can provide for redundancy of installation of the plunger assembly 240 within the barrel 230 and the locking assembly 260—for example, allowing the plunger assembly 240 to be installed in a flipped or rotated (e.g., by 180 degrees) configuration without loss of functionality.

Referring to FIGS. 2A-8B together, in some aspects of the present technology the syringe 120 is configured to (i) automatically lock the plunger assembly 240 to the locking assembly 260 when the plunger assembly 240 is withdrawn through the barrel 230 with a vacuum within the barrel 230, (ii) automatically unlock the plunger assembly 240 from the locking assembly 260 when the barrel 230 no longer experiences vacuum, and (iii) inhibit or even prevent automatic locking of the plunger assembly 240 to the locking assembly 260 when the plunger assembly 240 is withdrawn through the barrel 230 with no or negligible vacuum within the barrel 230. For example, regarding (i) and as described in detail above with reference to FIG. 8A, the vacuum force $F_{vacuum}$ acting on the plunger assembly 240 can overcome the biasing force $F_{biasing}$ of the biasing member 285 to move the unlocking member 280 away from the locking recess 405 to expose the locking recess 405 such that the lock plate 765 can be driven into the locking recess 405 (e.g., via the lock feature 496) to lock the position of the plunger assembly 240 relative to the locking assembly 260. Regarding (ii) and as described in detail above with reference to FIG. 8B, release of the vacuum force $F_{vacuum}$ permits the biasing force $F_{biasing}$ of the biasing member 285 to drive the unlocking member 280 to engage the lock plate 765 and drive the lock plate 765 out of the locking recess 405 (e.g., via the unlock feature 401) to unlock the position of the plunger assembly 240 relative to the locking assembly 260. Finally, regarding (iii), in the absence of the vacuum force $F_{vacuum}$ the unlocking member 280 surrounds and radially shields (e.g., covers) the locking recess 405 such that the lock plate 765 cannot be inserted into the locking recess 405 even as the plunger assembly 240 is withdrawn through the locking assembly 260.

Accordingly, the syringe 120 can be an automatic-locking and automatic-unlocking syringe 120 in response to vacuum pressure in the barrel 230. In contrast, some conventional syringes may automatically lock upon withdrawal of a plunger or be user-actuatable to selectively lock the position of the plunger. However, these devices require a user input to lock the plunger and/or to unlock the plunger and allow its further movement. In some aspects of the present technology, the automatic-locking and automatic-unlocking syringe 120 of the present technology can simplify a clot removal procedure using the syringe 120. For example, referring to FIGS. 1-2B, during a clot removal procedure using the system 100, the plunger assembly 240 can be withdrawn with the fluid control device 114 in a closed position to generate vacuum pressure in the barrel 230 that acts on the plunger assembly 240 to allow the plunger assembly 240 to lock in position to the lock plate 765 without any user (e.g., physician) input when fully withdrawn through the barrel 230. The fluid control device 114 can then be opened to apply the vacuum pressure stored in the barrel 230 to the catheter 106 to aspirate clot material and blood into the barrel 230. With the vacuum pressure released, the plunger assembly 240 can automatically unlock from the locking assembly 260 without user input via the biasing member 285 urging the unlock feature 401 against the lock plate 765. With the fluid control device 114 closed, the plunger assembly 240 can then be depressed through the barrel 230 to drive the blood through the filter 279 and the filtered blood out through the outlet tube 246 (and/or the outlet tube 246 may be aspirated to draw the blood through the filter 279 and the filtered blood out through the outlet tube 246). Such automatic locking and unlocking of the syringe 120 simplifies the clot removal procedure.

In additional aspects of the present technology, the syringe 120 can act as a normal syringe (e.g., without automatic locking) when vacuum is not generated within the barrel 230. For example, when the syringe 120 is used for procedural steps other than aspiration, such as contrast injection, saline flushing, and/or the like, the syringe 120 can act as a standard syringe that does not lock to the locking assembly 260 when the plunger assembly 240 is withdrawn during a stroke. More specifically, when little or no vacuum pressure is generated within the barrel 230 during withdrawal of the plunger assembly 240, the biasing member 285 can bias the seal assembly 244 to the first position shown in FIGS. 4A and 4B in which the tabs 494 and the locking features 496 of the handle assembly 242 are positioned within the corresponding ones of the channels 492 formed in/by the unlocking member 280 and the unlock features 401 such that the locking recesses 405 are covered (e.g., radially shielded) by the unlocking member 280. Accordingly, when the plunger assembly 240 is withdrawn through/past the locking assembly 260 the lock plate 765 does not engage the locking recesses 405 and the plunger assembly 240 can be freely withdrawn proximally and/or advanced distally without locking to the locking assembly 260.

Referring to FIG. 2A, in some embodiments the syringe 120 can include an indicator 222 configured to provide an indication to the user of a level of vacuum in the barrel 230 and/or in the system 100 (FIG. 1) as a whole. In the illustrated embodiment, the indicator 222 includes an (i) aperture or window 223 in the first shaft 250 of the handle assembly 242 and (ii) a visual indicator 224 on the second shaft 270 and at least partially visible through the window 223. As described in detail above with reference to FIGS. 4A-6, the second shaft 270 translates within the first shaft 250 as the seal assembly 244 moves relative to the handle assembly 242 in response to vacuum pressure within the barrel 230. This movement can position the visual indicator 224 differently with respect to the window 223 based on a level of vacuum in the barrel 230.

Referring to FIG. 3, the visual indicator 224 can comprise a color scale including, for example, a first color 225 (e.g., red) along a first portion of the second shaft 270, a second color 226 (e.g., orange) along a second portion of the second shaft 270 proximal of the first portion, and a third color 227 (e.g., green) along a third portion of the second shaft 270 proximal of the second portion. Referring to FIGS. 2A and 3, when vacuum is not present in the barrel 230 or there is negligible vacuum within the barrel 230, the plunger assembly 240 is in the first position as shown in FIGS. 2A and 3 and the first color 225 can be visible through the window 223 indicating that there is no or negligible vacuum within the barrel 230. When a maximum or substantially maximum vacuum is within the barrel 230, the plunger assembly 240 is in the second position shown in FIGS. 5A and 5B and the third color 227 can be visible through the window 223 indicating that there is the maximum or substantially maximum vacuum within the barrel 230. When an intermediate vacuum between no vacuum and the maximum vacuum is within the barrel 230, the plunger assembly 240 is in an intermediate position (e.g., the intermediate position shown in FIG. 6) and the second color 226 can be visible through the window 223 indicating that there is the intermediate vacuum within the barrel 230. Likewise, when the plunger assembly 240 is in a withdrawn position, the first color 225 can indicate that the plunger assembly 240 is unlocked from the locking assembly 260, the second color 226 can indicate that plunger assembly 240 is partially unlocked, in the process of unlocking, and/or will soon unlock from the locking assembly 260, and the third color 227 can indicate that the plunger assembly 240 is locked to the locking assembly 260. In other embodiments, rather than different colors, the visual indicator 224 can comprise different icons, textures, values, marks, etc., that indicate the various vacuum and locking states.

Figure 9:
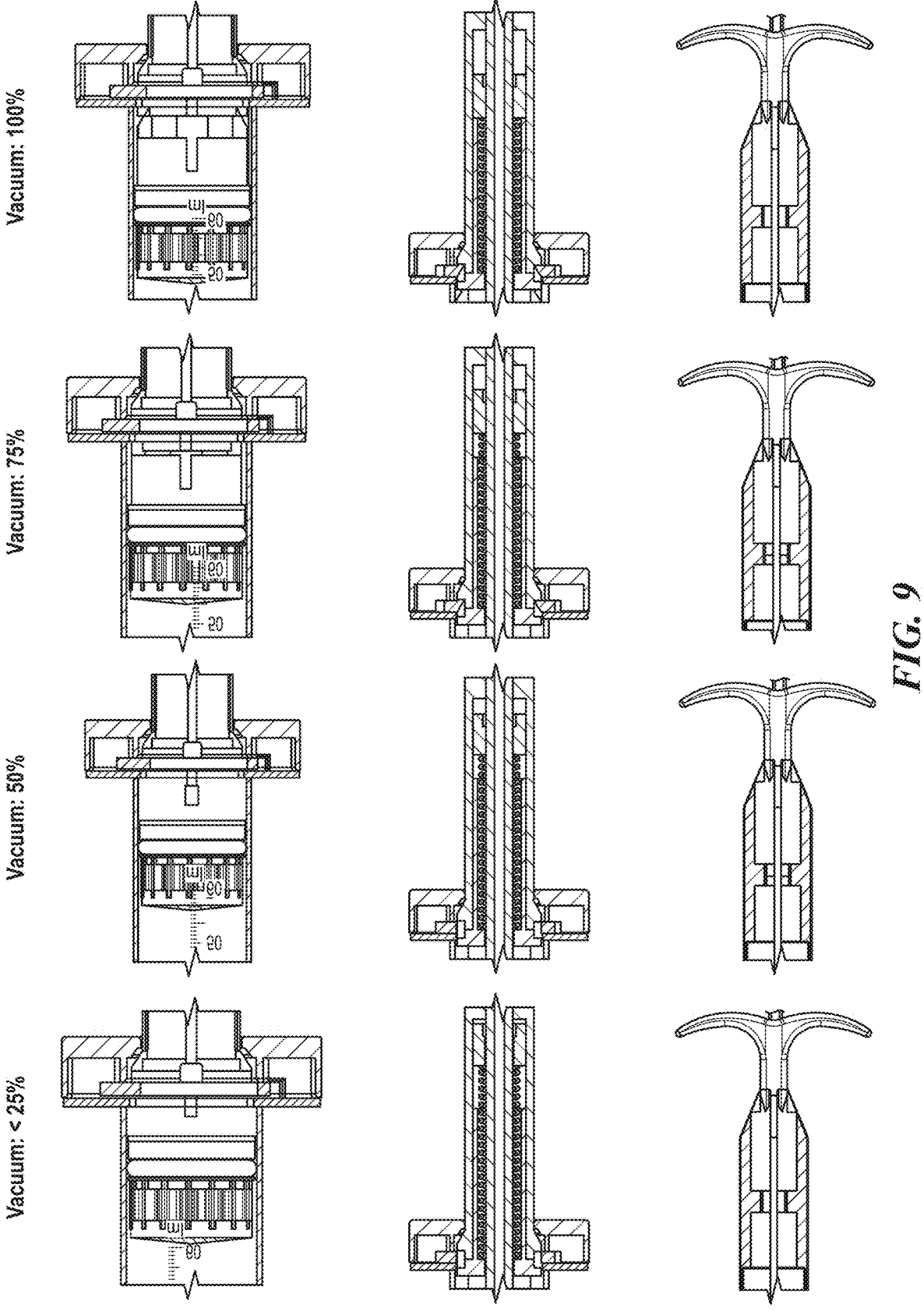
FIG. 9 is a table including various views of the syringe of FIGS. 2A and 2B at different vacuum levels in accordance with embodiments of the present technology.

FIG. 9 is a table including various views of the syringe 120 at different vacuum levels in accordance with embodiments of the present technology. More specifically, referring to FIGS. 2A-9, the views in the first column show the syringe 120 under no or negligible vacuum (e.g., less than 25% of a 100% maximum vacuum), the views in the second column show the syringe 120 under 50% of the maximum vacuum, the views in the third column show the syringe 120 under 75% of the maximum vacuum, and the views in the fourth column show the syringe 120 under the 100% maximum vacuum. The views in row A are partially-transparent side views of the syringe 120 proximate the locking assembly 260 with the plunger assembly 240 withdrawn to near the position at which the plunger assembly 240 can lock the locking assembly 260 (e.g., with the locking recesses 405 of the handle assembly 242 and/or the unlocking member 280 of the seal assembly 244 proximate to the lock plate 765). The views in row B are cross-sectional side views of a proximal portion of the syringe 120 at and proximal of the locking assembly 260 with the plunger assembly 240 withdrawn to near the position at which the plunger assembly 240 can lock the locking assembly 260. The views in row C are side views of a proximal portion of the handle assembly 242 including the indicator 222.

Figure 10:
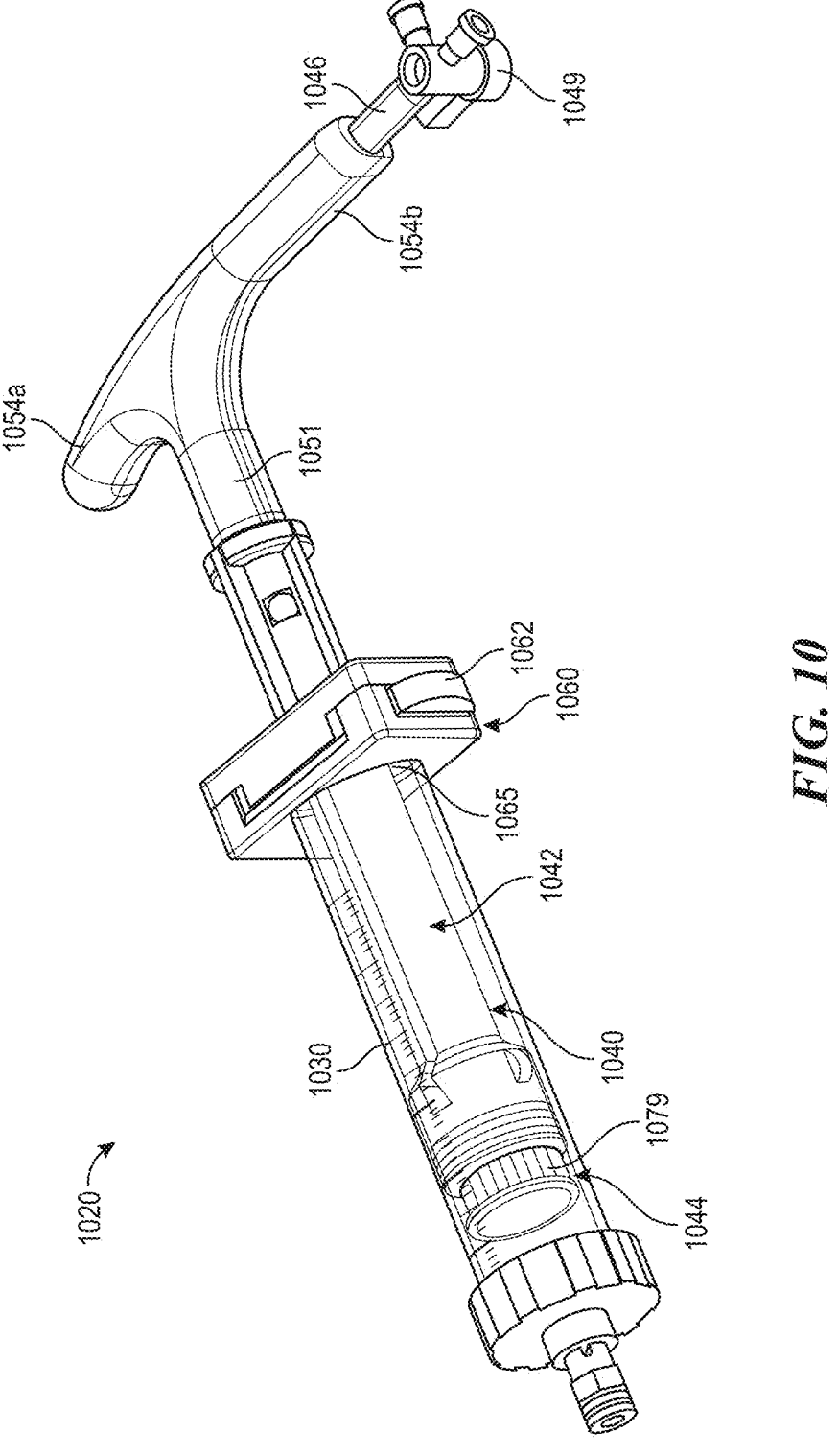
FIG. 10 is an isometric view of a syringe in accordance with additional embodiments of the present technology.

FIG. 10 is an isometric view of a syringe 1020 in accordance with additional embodiments of the present technology. The syringe 1020 can include some features that are at least generally similar in structure and function, or identical in structure and function, to the corresponding features of the syringe 120 described in detail above with reference to FIGS. 1-9, and can operate in a generally similar or identical manner to the syringe 120. For example, in the illustrated embodiment the syringe 1020 is an automatic-locking and automatic-unlocking syringe including a plunger assembly 1040 slidably positioned within a barrel 1030. The barrel 1030 is shown as partially transparent in FIG. 10 for clarity. In the illustrated embodiment, the plunger assembly 1040 includes a handle assembly 1042 operably coupled to a seal assembly 1044, and a locking assembly 1060 coupled to the barrel 1030. When the plunger assembly 1040 is withdrawn through the barrel 1030 and vacuum pressure is generated within the barrel 1030, the seal assembly 1044 is configured to move away from the handle assembly 1042 to permit locking of the plunger assembly 1040 to the locking assembly 1060 as described in detail above with reference to FIGS. 1-9.

The handle assembly 1042 includes a proximal end portion 1051 configured (e.g., shaped, sized) to be grasped by a user for withdrawing (e.g., retracting, pulling) and/or depressing (e.g., advancing, pushing) the plunger assembly 1040 through the barrel 1030 during operation of the syringe 1020. For example, in the illustrated embodiment the proximal end 1051 includes a pair of opposing flanges 1054 (individually identified as a first flange 1054a and a second flange 1054b) extending radially outward from a longitudinal axis of the syringe 1020 and forming a handle configured to be grasped by a hand of the user. In some embodiments, the second flange 1054b is larger than the first flange 1054a. An outlet tube 1046 can extend at least partially through the handle assembly 1042 and through the second flange 1054b to a connector 1049, such as a multi-lumen connector 1049. The seal assembly 1044 can include a filter 1079 fluidly coupled to the outlet 1046 via, for example, a lumen extending at least partially through the seal assembly 1044 (e.g., the lumen in the second shaft 270 described in detail above with reference to FIGS. 2A and 2B). The connector 1049 can be coupled to a reservoir/container for receiving blood filtered by the filter 1079 (e.g., as the plunger assembly 1040 is depressed with clot material and blood in the barrel 1030), a fluid source for injecting fluid into the barrel 1030, and/or the like.

In the illustrated embodiment, the locking assembly 1060 further includes an actuator 1062 operably coupled to a lock plate 1065 (partially obscured in FIG. 10). The lock plate 1065 can engage the plunger assembly 1040 (e.g., a locking recess formed thereby/therein) to selectively lock the plunger assembly 1040 relative to the barrel 1030 as described in detail above with reference to FIGS. 2A-9. The actuator 1062 can comprise a button and/or the like configured to be actuated (e.g., depressed) by a user to manually unlock the lock plate 1065 from the plunger assembly 1040 to, for example, allow the plunger assembly 1040 to move (e.g., be depressed) through the barrel 1030. In some aspects of the present technology, the actuator 1062 can act as an override feature to allow the plunger assembly 1040 to be unlocked from the locking assembly 1060 when there is significant vacuum pressure within the barrel 1030. In addition to manual unlock from the locking assembly 1060 via the actuator 1062, the plunger assembly 1040 can be configured to automatically unlock from the locking assembly 1060 as described in detail above with reference to FIGS. 2A-9. In some embodiments, the locking assembly 1060 and the actuator 1062 can include some features generally similar in structure and/or function, or identical in structure and/or function, to those of any of the locking assemblies and/or actuators (e.g., buttons) described in U.S. patent application Ser. No. 17/396,426, titled "AUTOMATI-CALLY-LOCKING VACUUM SYRINGES, AND ASSO-CIATED SYSTEMS AND METHODS," and filed Aug. 8, 2021, which is incorporated herein by reference in its entirety.

Figure 11A:
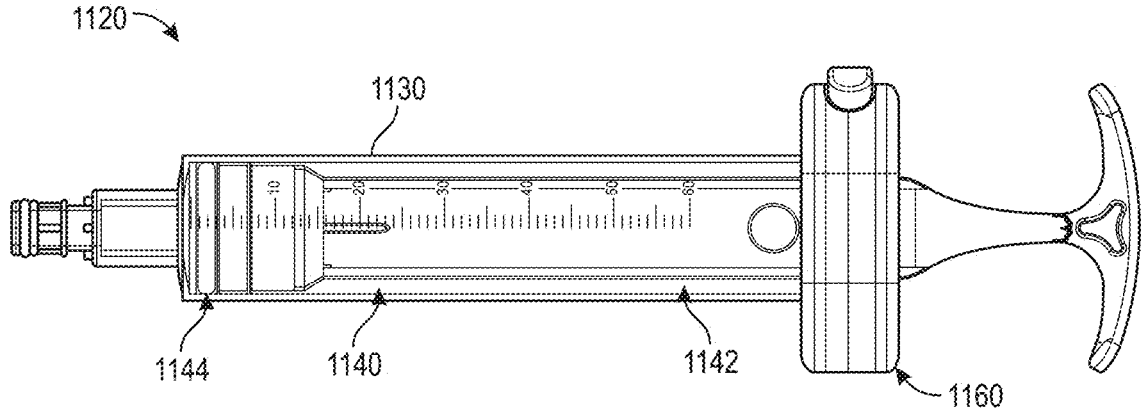
FIGS. 11A and 11B are side views of a syringe that can be used in the clot treatment system of FIG. 1 in a first position and a second position, respectively, in accordance with additional embodiments of the present technology.
Figure 11B:
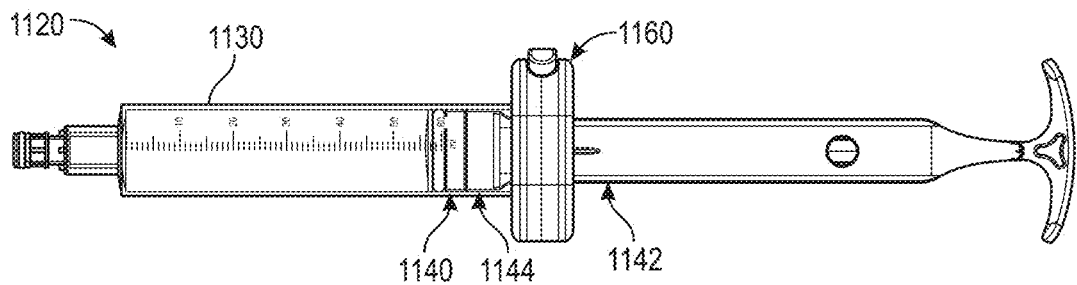

FIGS. 11A and 11B are side views of a syringe 1120 that can be used in the clot treatment system of FIG. 1 in a first position (e.g., a depressed position) and a second position (e.g., a withdrawn position), respectively, in accordance with additional embodiments of the present technology. Referring to FIGS. 11A and 11B, the syringe 1120 can include some features that are at least generally similar in structure and function, or identical in structure and function, to the corresponding features of the syringe 120 and/or the syringe 1020 described in detail above with reference to FIGS. 1-10, and can operate in a generally similar or identical manner to the syringe 120 and/or the syringe 1020. For example, in the illustrated embodiment the syringe 1120 is an automatic-locking and automatic-unlocking syringe including a plunger assembly 1140 slidably positioned within a barrel 1130.

In the illustrated embodiment, the plunger assembly 1140 includes a handle assembly 1142 operably coupled to a seal assembly 1144. The syringe 1120 further includes a locking assembly 1160 coupled to the barrel 1130. The locking assembly 1160 is configured to selectively lock the plunger assembly 1140 in a withdrawn position under vacuum pressure as described in detail above with reference to FIGS. 8A-10. When the plunger assembly 1140 is withdrawn through the barrel 1130, as shown in FIG. 11B, and vacuum pressure is generated within the barrel 1130, the seal assembly 1144 is configured to move away from the handle assembly 1142 to permit locking of the plunger assembly 1140 to the locking assembly 1160 as described in detail above with reference to FIGS. 1-10. Referring to FIG. 11A, the plunger assembly 1140 is in the first position and is fully depressed within the barrel 1130. Referring to FIG. 11B, the plunger assembly 1140 is in the second position and is withdrawn through the barrel 1130 and locked to the locking assembly 1160. In the illustrated embodiment, the syringe 1120 is not a filtering syringe and, for example, the seal assembly 1144 does not include features such as the filter 279, the cap 278, and/or the distal opening 274 described in detail above with reference to FIGS. 2A and 2B. Accordingly, the handle assembly 1142 need not define a lumen therethrough for, for example, receiving filtered blood.

Figure 12A:
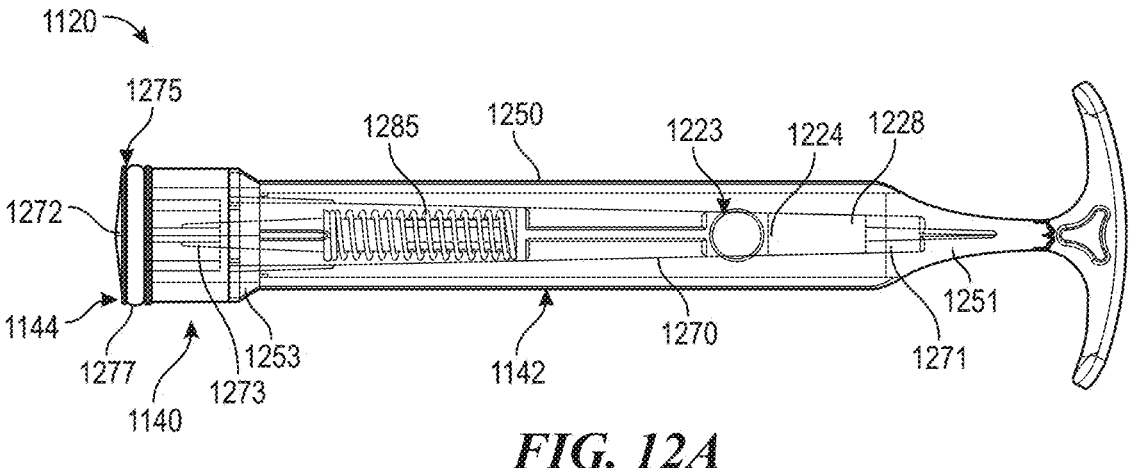
FIGS. 12A and 13A are partially-transparent side views of a plunger assembly of the syringe of FIGS. 11A and 11B in a first position and a second position, respectively, in accordance with embodiments of the present technology.
Figure 13A:
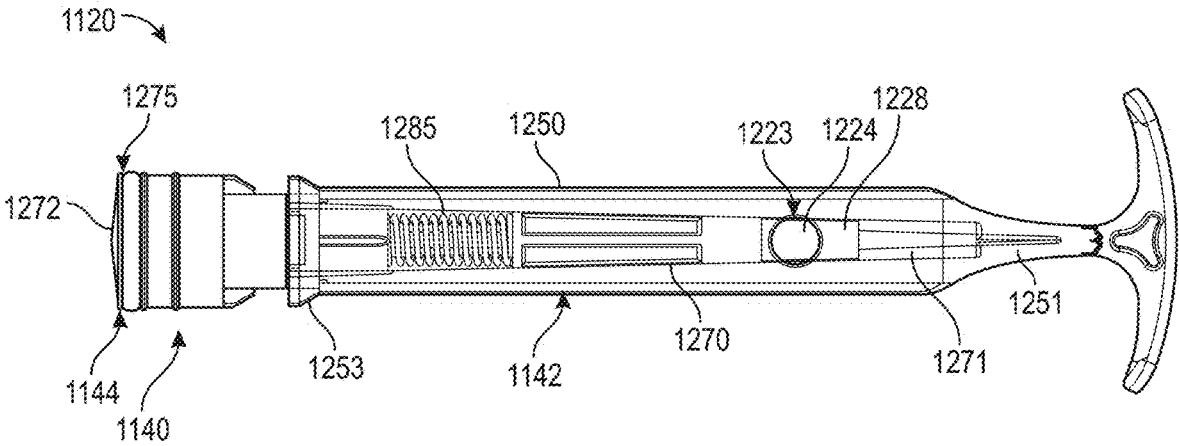

FIGS. 12A and 13A are partially-transparent side views of the plunger assembly 1140 of the syringe 1120 of FIGS. 11A and 11B in a first position (e.g., a non-vacuum position) and a second position (e.g., a vacuum position), respectively, in accordance with embodiments of the present technology. Referring to FIGS. 12A and 13A, in the illustrated embodiment the handle assembly 1142 includes a first shaft 1250 extending between a proximal end portion 1251 and a distal end portion 1253. The proximal end portion 1251 can be configured to be grasped by a user for withdrawing and/or depressing the plunger assembly 1140 through the barrel 1130 during operation of the syringe 1120, as described in detail above with reference to FIGS. 1-10. The seal assembly 1144 includes a second shaft 1270 having a proximal end portion 1271 and a distal end portion 1273 (FIG. 12A). The distal end portion 1273 of the second shaft 1270 can be coupled to a sealing head 1272. A circumferential groove 1275 in the sealing head 1272 can receive a sealing member 1277 therein, such as an O-ring, configured to sealingly engage an interior surface of the barrel 1130 (FIGS. 11A and 11B).

The plunger assembly 1140 further includes a biasing member 1285 operably coupling the first shaft 1250 to the second shaft 1270. The handle assembly 1142 can be configured to be withdrawn relative to the barrel 1130 (FIGS. 11A and 11B) to withdraw the seal assembly 1244 and the sealing member 1277 through the barrel 1130 to generate vacuum pressure within the barrel 1130. The vacuum pressure can generate a vacuum force on the seal assembly 1144 greater than a biasing force of the biasing member 1285 such that the biasing member 1285 compresses and the sealing head 1272 moves away from the distal portion of the first shaft 1250 as shown in FIG. 13A.

Figure 12B:
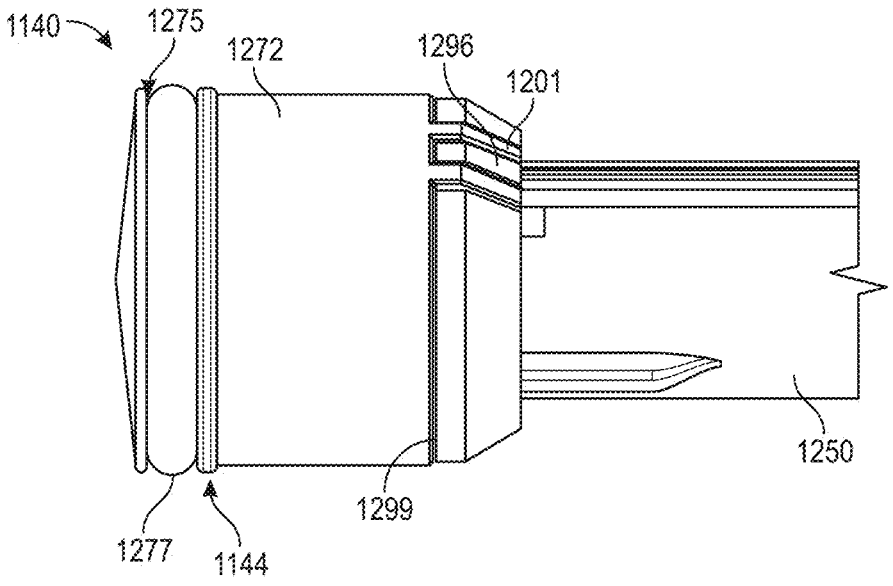
FIGS. 12B and 13B are enlarged side views of a distal portion of a plunger assembly of the syringe of FIGS. 12A and 13A in the first position and the second position, respectively, in accordance with embodiments of the present technology.
Figure 13B:
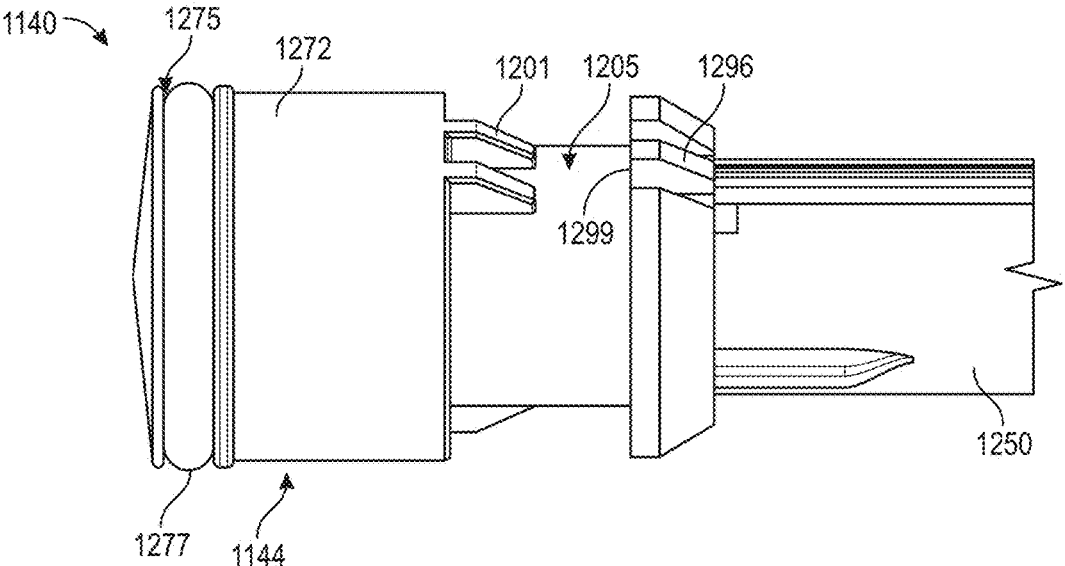

FIGS. 12B and 13B are enlarged side views of a distal portion of the plunger assembly 1140 of FIGS. 12A and 13A, respectively, in accordance with embodiments of the present technology. Referring to FIGS. 12B and 13B, in the illustrated embodiment the sealing head 1272 is configured as an unlocking member (e.g., an integral component integrating/combining, for example, the sealing head 272 and the unlocking member 280 of FIGS. 2A and 2B). In the illustrated embodiment, the sealing head 1272 includes one or more unlock features 1201 and the first shaft 1250 includes one or more lock features 1296. The lock features 1296 are aligned with corresponding ones of the unlock features 1201 and configured to nest therein in the first position (FIG. 12B) with a stop surface 1299 of the locking features 1296 abutting the sealing head 1272. In the second position (FIG. 13B), vacuum pressure on the sealing head 1272 compresses the biasing member 1285 (FIGS. 12A and 13A) such that the lock features 1296 are spaced apart from the unlock features 1201 to define a locking recess 1205. In some embodiments, compared to the embodiment of FIGS. 2-9, the plunger assembly 1120 can include a configuration of tabs (not shown; e.g., the tabs 494 of FIGS. 4B-6) and channels (not shown; e.g., the channels 492 of FIGS. 4B-6) that are internal to the first shaft 1250 and sealing head 1272 to facilitate continued alignment of these components.

Referring to FIGS. 12A and 13A, the plunger assembly 1140 can include an aperture or window 1223 in the first shaft 1250 and the second shaft 1270 of the handle assembly 1142 configured to provide an indication to the user of a level of vacuum in the barrel 1130 and/or in the system 100 (FIG. 1) as a whole. As described in detail above with reference to FIGS. 4A-6, the second shaft 1270 translates within the first shaft 1250 as the seal assembly 1144 moves relative to the handle assembly 1142 in response to vacuum pressure within the barrel 1130. This movement can position a visual indicator 1224 differently with respect to the window 1223 based on a level of vacuum in the barrel 1130 (FIGS. 11A and 11B). In other embodiments, the aperture or window 1223 can comprise different-shaped openings in the first shaft 1250 and the second shaft 1270 of the handle assembly 1142.

The visual indicator 1224 can comprise a solid color 1228. Referring to FIGS. 12A, when vacuum is not present in the barrel 1130 or there is negligible vacuum within the barrel 1130, the plunger assembly 1140 is in the first position and the solid color 1228 is not visible through the window 1223, indicating that there is no or negligible vacuum within the barrel 1130. When vacuum is generated within the barrel 1130, the plunger assembly 1140 is in the second position and the solid color 1228 can be visible through the window 1223 indicating that there is vacuum pressure within the barrel 1130. Likewise, when the plunger assembly 1140 is in a withdrawn position, the lack of visibility of the solid color 1228 can indicate that the plunger assembly 1140 is unlocked from the locking assembly 1160, and the visibility of the solid color 1228 can indicate that the plunger assembly 1140 is locked to the locking assembly 1160. For example, the visual indicator 1224 is visible through the window 1223 in FIG. 11B indicating that the plunger assembly 1140 is locked to the locking assembly 1160. In other embodiments, rather than different colors, the visual indicator 1224 can comprise different icons, textures, values, marks, etc., that indicate the various vacuum and locking states.

Figure 14A:
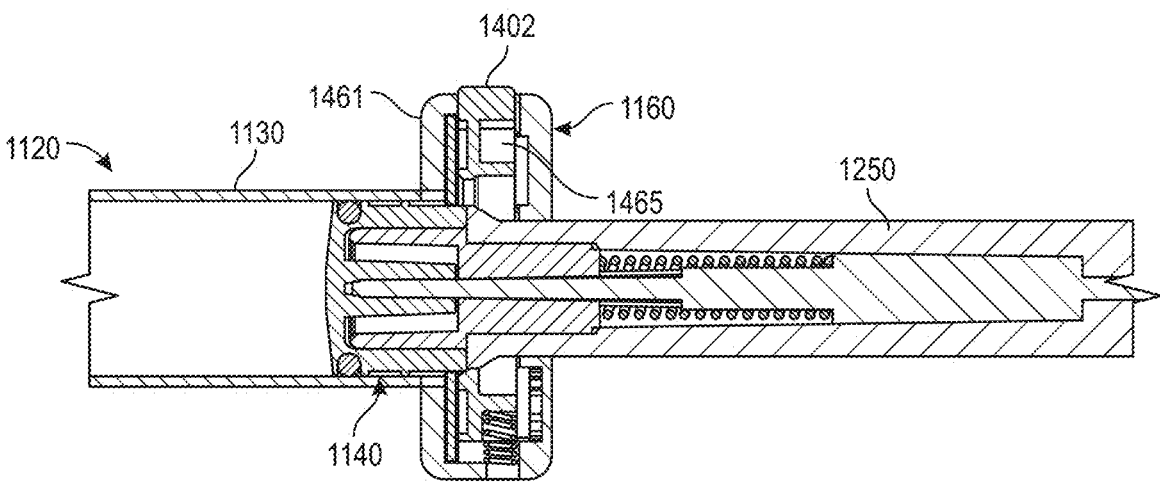
FIGS. 14A and 14B are cross-sectional side views of the syringe of FIGS. 11A and 11B in an unlocked position and a locked position, respectively, in accordance with additional embodiments of the present technology.
Figure 14B:
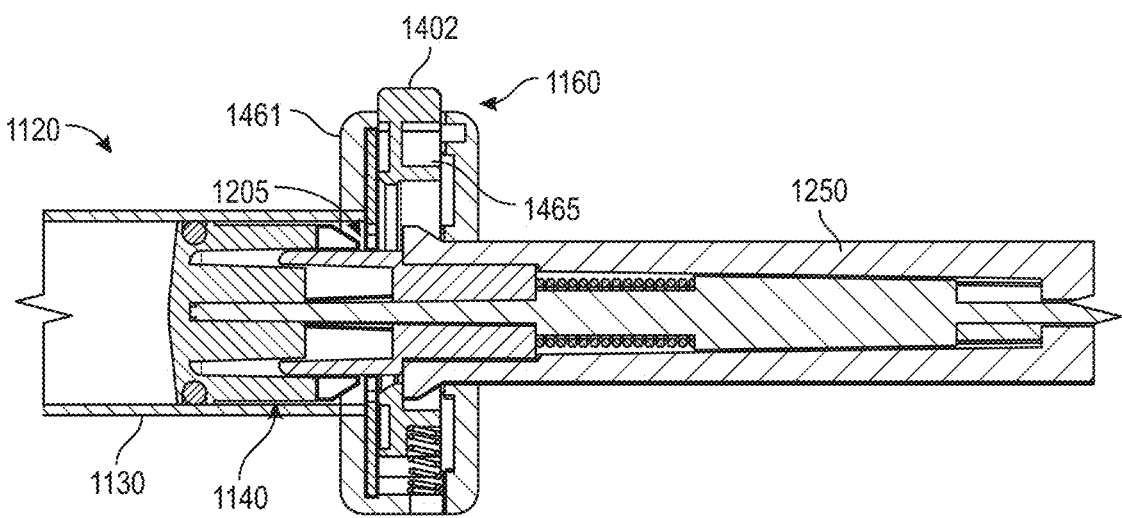

FIGS. 14A and 14B are cross-sectional side views of the syringe 1120 of FIGS. 11A and 11B in an unlocked position and a locked position, respectively, in accordance with additional embodiments of the present technology. Referring to FIGS. 14A and 14B, in the illustrated embodiment the locking assembly 1160 includes a housing 1461 and a lock plate 1465. In the locked position shown in FIG. 14B, the plunger assembly 1140 is in the second position (FIGS. 12B and 13B) and the lock plate 1465 can engage the plunger assembly 1140 (e.g., the locking recess 1205 formed thereby/therein) to selectively lock the plunger assembly 1140 relative to the barrel 1130. In the unlocked position shown in FIG. 14A, the plunger assembly 1140 is in the first position (FIGS. 12A and 13A) such that the locking recess 1205 is shielded and the lock plate 1465 does not engage the locking recess 1205. A button portion 1402 of the lock plate 1465 can protrude from the housing 1461 when the locking assembly 1160 is in the locked position. The button portion 1402 is configured to be actuated (e.g., depressed) by a user to manually unlock the lock plate 1465 from the plunger assembly 1140 to, for example, allow the plunger assembly 1140 to move (e.g., be depressed) through the barrel 1130. In some aspects of the present technology, the lock plate 1465 (e.g., the button portion 1402) can act as an override feature to allow the plunger assembly 1140 to be unlocked from the locking assembly 1160 when there is significant vacuum pressure within the barrel 1130.

In addition to manual unlock from the locking assembly 1160 via the lock plate 1465, the plunger assembly 1140 can be configured to automatically unlock from the locking assembly 1160 as described in detail above with reference to FIGS. 2A-9. For example, when vacuum pressure is released, the biasing member 1285 can move the sealing head 1272 toward the first shaft 1250 such that the ramped unlock features 1201 drive the lock plate 1465 out of the locking recess 1205. In some embodiments, the locking assembly 1160 and the lock plate 1465 can include some features generally similar in structure and/or function, or identical in structure and/or function, to those of any of the locking assemblies and/or actuators (e.g., buttons) described in U.S. patent application Ser. No. 17/396,426, titled "AUTOMATICALLY-LOCKING VACUUM SYRINGES, AND ASSOCIATED SYSTEMS AND METHODS," and filed Aug. 8, 2021, which is incorporated herein by reference in its entirety.

Figure 15:
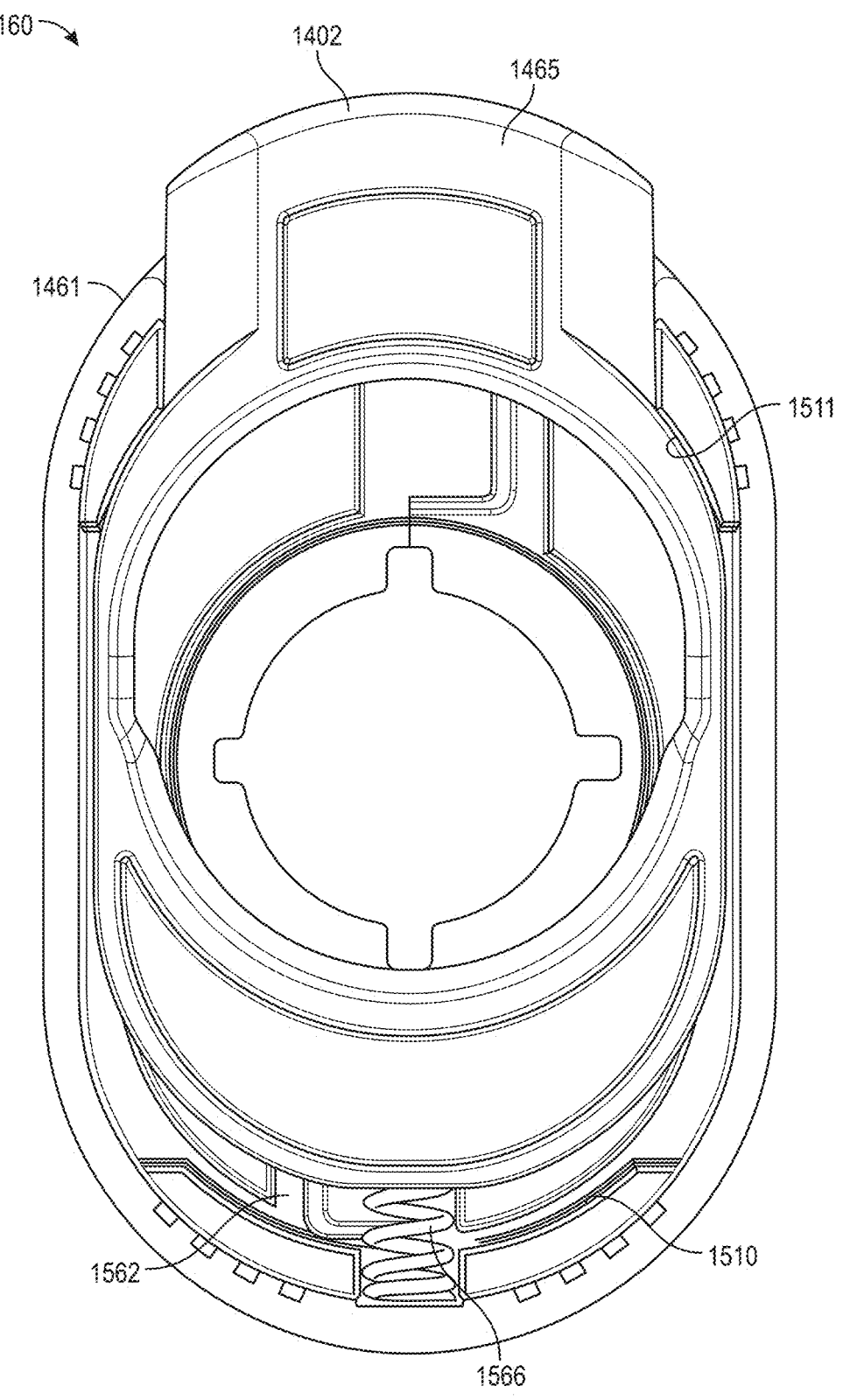
FIG. 15 is a cross-sectional view of a locking assembly of the syringe of FIGS. 11A and 11B in accordance with embodiments of the present technology.

FIG. 15 is a cross-sectional view of the locking assembly 1160 of the syringe 1120 of FIGS. 11A and 11B in accordance with embodiments of the present technology. In the illustrated embodiment, the housing 1461 defines a recess 1562 having a first end portion 1510 and a second end portion 1511 opposite the first end portion 1510. One or more biasing members 1566 can extend between and operably couple the lock plate 1465 to the housing 1461 proximate the first end portion 1510 of the recess 1562. The biasing member 1566 can comprise, for example, a compression spring that biases the lock plate 1465 away from the first end portion 1510 of the recess 1562 toward the second end portion 1511 of the recess 1562. Referring to FIGS. 14A-15 together, in the locked position (FIG. 14B) the biasing member 1566 forces the lock plate 1465 into the locking recess 1205. When vacuum pressure is released within the barrel 1130 the ramped unlock features 1201 engage the lock plate 1465 to move the lock plate 1465 against the biasing force of the biasing member 1566 to drive the lock plate 1465 out of the locking recess 1205 as shown in FIG. 14A. Likewise, actuation of the button portion 1402 can drive the lock plate 1465 against the biasing force of the biasing member 1566 to release the lock plate 1465 from the locking recess 1205 to unlock the plunger assembly 1140 from the locking assembly 1160.

The following examples are illustrative of several embodiments of the present technology:

1. An automatic-locking and automatic-unlocking syringe, comprising:

a barrel;

a plunger assembly slidably positioned within the barrel, wherein the plunger assembly is movable between a first position and a second position; and a locking assembly coupled to the barrel, wherein— the plunger assembly is configured to be withdrawn through the barrel to generate vacuum pressure in the barrel;

the plunger assembly is configured to move from the first position to the second position in response to the vacuum pressure;

the plunger assembly is configured to move from the second position to the first position in response to the vacuum pressure being released;

the plunger assembly is configured to lock to the locking assembly in the second position such that the locking assembly inhibits movement of the plunger assembly through the barrel; and the plunger assembly is configured to unlock from the locking assembly in the first position such that the locking assembly permits movement of the plunger assembly through the barrel.

2. The syringe of example 1 wherein the plunger assembly includes a sealing head, a shaft, and a biasing member operably coupling the sealing head to the shaft.

3. The syringe of example 2 wherein in the first position the biasing member biases the sealing head into engagement within the shaft.

4. The syringe of example 3 wherein in the second position the vacuum pressure moves the sealing head from the shaft, against a biasing force of the biasing member, to define a locking recess therebetween.

5. The syringe of example 4 wherein the locking assembly includes a lock plate configured to be positioned in the locking recess when the plunger assembly is in the second position such that the lock plate inhibits movement of the plunger assembly through the barrel.

6. The syringe of example 5 wherein movement of the plunger assembly from the second position to the first position is configured to drive the lock plate from the locking recess to permit movement of the plunger assembly through the barrel.

7. The syringe of example 5 or example 6 wherein the lock plate includes a button portion configured to be actuated by a user to drive the lock plate out of the locking recess when the plunger assembly is in the second position to permit movement of the plunger assembly through the barrel.

8. The syringe of any one of examples 1-7 wherein the locking assembly includes a housing, a lock plate positioned at least partially within the housing, and a biasing member operably coupling the lock plate to the housing.

9. The syringe of example 8 wherein the biasing member is configured to drive the lock plate into locking engagement with the plunger assembly when the plunger assembly is in the second position, and wherein the plunger assembly is configured to drive the lock plate against a biasing force of the biasing member when the plunger assembly is in the first position.

10. The syringe of any one of examples 1-9 wherein the plunger assembly further comprises a filtering seal assembly configured to separate clot material from blood.

11. A syringe, comprising:
a barrel; and
a plunger assembly slidably positioned within the barrel, wherein the plunger assembly comprises—
a handle assembly including a first shaft having a distal portion;
a seal assembly including a second shaft and a seal head coupled to the second shaft, wherein the seal head includes a sealing member positioned to sealingly engage the barrel; and
a biasing member operably coupling the first shaft to the second shaft, wherein the biasing member has a biasing force, and wherein
the handle assembly is configured to be withdrawn relative to the barrel to withdraw the seal assembly and the sealing member through the barrel to generate vacuum pressure within the barrel; and
the vacuum pressure is configured to generate a vacuum force on the seal assembly greater than the biasing force of the biasing member such that the biasing member compresses and the seal head moves away from the distal portion of the first shaft.

12. The syringe of example 11 wherein the biasing member is a compression spring.

13. The syringe of example 11 or example 12 wherein in the absence of the vacuum pressure the biasing force is configured to drive the seal head to engage the distal portion of the first shaft.

14. The syringe of any one of examples 11-13, further comprising a locking assembly including a lock plate wherein the vacuum pressure is configured to generate the vacuum force on the seal assembly greater than the biasing force of the biasing member such that the seal head moves away from the distal portion of the first shaft to define a locking recess therebetween, and wherein the lock plate is configured to be positioned in the locking recess to inhibit movement of the plunger assembly through the barrel.

15. The syringe of example 14 wherein in the absence of the vacuum pressure the biasing force is configured to drive the seal head to engage the distal portion of the first shaft to drive the lock plate from the locking recess.

16. The syringe of any one of examples 11-15 wherein the second shaft comprises a visual indicator, wherein the first shaft includes an aperture, and wherein the visual indicator is at least partially visible through the aperture when the vacuum force on the seal assembly is greater than the biasing force of the biasing member such that the seal head moves away from the distal portion of the first shaft.

17. A syringe, comprising:
a barrel; and
a plunger assembly slidably positioned within the barrel, wherein the plunger assembly comprises—
a handle assembly including a first shaft having a distal portion and a locking recess formed at the distal portion; and
a seal assembly including a shield member, wherein the seal assembly is movable relative to the handle assembly between (a) a first position in which the shield member radially shields the locking recess and (b) a second position in which the shield member is axially spaced apart from the locking recess.

18. The syringe of example 17 wherein the shield member further comprises a ramped unlocking projection, wherein the first shaft further comprises a locking projection, and wherein the locking projection is configured to mate with the unlocking projection in the first position.

19. The syringe of example 17 or example 18, further comprising a locking assembly including a lock plate configured to engage the locking recess when the seal assembly is in the second position to lock the position of the plunger assembly within the barrel.

20. The syringe of example 19 wherein the shield member includes a ramped unlocking feature, and wherein movement of the seal assembly from the second position to the first position is configured to move the ramped unlocking feature relative to the locking recess to drive the lock plate from the locking recess to permit movement of the plunger assembly through the barrel.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An automatic-locking and automatic-unlocking syringe, comprising:
a barrel;
a plunger assembly slidably positioned within the barrel, wherein the plunger assembly is movable between a first position and a second position; and
a locking assembly coupled to the barrel, wherein—
the plunger assembly is configured to be withdrawn through the barrel to generate vacuum pressure in the barrel;
the plunger assembly is configured to move from the first position to the second position in response to the vacuum pressure;
the plunger assembly is configured to move from the second position to the first position in response to the vacuum pressure being released;
the plunger assembly is configured to lock to the locking assembly in the second position such that the locking assembly inhibits movement of the plunger assembly through the barrel; and
the plunger assembly is configured to unlock from the locking assembly in the first position such that the locking assembly permits movement of the plunger assembly through the barrel.

2. The syringe of claim 1 wherein the plunger assembly includes a sealing head, a shaft, and a biasing member operably coupling the sealing head to the shaft.

3. The syringe of claim 2 wherein in the first position the biasing member biases the sealing head into engagement within the shaft.

4. The syringe of claim 3 wherein in the second position the vacuum pressure moves the sealing head from the shaft, against a biasing force of the biasing member, to define a locking recess therebetween.

5. The syringe of claim 4 wherein the locking assembly includes a lock plate configured to be positioned in the locking recess when the plunger assembly is in the second position such that the lock plate inhibits movement of the plunger assembly through the barrel.

6. The syringe of claim 5 wherein movement of the plunger assembly from the second position to the first position is configured to drive the lock plate from the locking recess to permit movement of the plunger assembly through the barrel.

7. The syringe of claim 5 wherein the lock plate includes a button portion configured to be actuated by a user to drive the lock plate out of the locking recess when the plunger assembly is in the second position to permit movement of the plunger assembly through the barrel.

8. The syringe of claim 1 wherein the locking assembly includes a housing, a lock plate positioned at least partially within the housing, and a biasing member operably coupling the lock plate to the housing.

9. The syringe of claim 8 wherein the biasing member is configured to drive the lock plate into locking engagement with the plunger assembly when the plunger assembly is in the second position, and wherein the plunger assembly is configured to drive the lock plate against a biasing force of the biasing member when the plunger assembly is in the first position.

10. The syringe of claim 1, wherein the plunger assembly comprises—
a handle assembly including a first shaft having a distal portion;
a seal assembly including a second shaft and a seal head coupled to the second shaft, wherein the seal head includes a sealing member positioned to sealingly engage the barrel; and
a biasing member operably coupling the first shaft to the second shaft, wherein the biasing member has a biasing force, and wherein—
the handle assembly is configured to be withdrawn relative to the barrel to withdraw the seal assembly and the sealing member through the barrel to generate the vacuum pressure in the barrel; and
in, the second position, the vacuum pressure is configured to generate a vacuum force on the seal assembly greater than the biasing force of the biasing member such that the biasing member compresses and the seal head moves away from the distal portion of the first shaft.

11. The syringe of claim 10 wherein the biasing member is a compression spring.

12. The syringe of claim 10 wherein, in the first position when the vacuum pressure is released, the biasing force is configured to drive the seal head to engage the distal portion of the first shaft.

13. The syringe of claim 10, wherein the locking assembly includes a lock plate, wherein the vacuum pressure is configured to generate the vacuum force on the seal assembly greater than the biasing force of the biasing member such that the seal head moves away from the distal portion of the first shaft to define a locking recess therebetween in the second position, and wherein the lock plate is configured to be positioned in the locking recess to lock the locking assembly to the plunger assembly to inhibit movement of the plunger assembly through the barrel.

14. The syringe of claim 13 wherein, in the first position when the vacuum pressure is released, the biasing force is configured to drive the seal head to engage the distal portion of the first shaft to drive the lock plate from the locking recess to unlock the locking assembly from the plunger assembly.

15. The syringe of claim 10 wherein the second shaft comprises a visual indicator, wherein the first shaft includes an aperture, and wherein the visual indicator is at least partially visible through the aperture when the vacuum force on the seal assembly is greater than the biasing force of the biasing member such that the seal head moves away from the distal portion of the first shaft.

* * * * *